United States Patent
Iwayama et al.

(10) Patent No.: US 7,713,957 B2
(45) Date of Patent: May 11, 2010

(54) PHARMACEUTICAL COMPOSITION CONTAINING GABAPENTIN OR PREGABALIN AND N-TYPE CALCIUM CHANNEL ANTAGONIST

(75) Inventors: Satoshi Iwayama, Kawasaki (JP); Hajime Koganei, Kawasaki (JP); Shinichi Fujita, Kawasaki (JP); Tomoko Takeda, Kawasaki (JP); Hiroshi Yamamoto, Kawasaki (JP); Seiji Niwa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1561 days.

(21) Appl. No.: 10/911,633

(22) Filed: Aug. 5, 2004

(65) Prior Publication Data

US 2005/0009814 A1    Jan. 13, 2005

Related U.S. Application Data

(63) Continuation of application No. PCT/JP03/01163, filed on Feb. 5, 2003.

(30) Foreign Application Priority Data

| Feb. 5, 2002 | (JP) | ............................. 2002-028208 |
| Apr. 12, 2002 | (JP) | ............................. 2002-111068 |
| Oct. 31, 2002 | (JP) | ............................. 2002-317480 |

(51) Int. Cl.
- *A61K 31/553* (2006.01)
- *A61K 31/554* (2006.01)
- *A01N 43/00* (2006.01)
- *A01N 43/46* (2006.01)
- *A01N 43/62* (2006.01)

(52) U.S. Cl. ................... 514/211.13; 514/217; 514/218

(58) Field of Classification Search ............ 514/211.13, 514/217, 218
See application file for complete search history.

(56) References Cited

U.S. PATENT DOCUMENTS 6,350,762 B1    2/2002    Niwa et al.

(Continued)

FOREIGN PATENT DOCUMENTS

EP    1 090 912    4/2001

(Continued)

OTHER PUBLICATIONS

U.S. Appl. No. 10/013,656, filed Dec. 13, 2001, Uneyama, et al.

(Continued)

*Primary Examiner*—San-ming Hui
(74) *Attorney, Agent, or Firm*—Oblon, Spivak, McClelland, Maier & Neustadt, L.L.P.

(57) ABSTRACT

The present invention relates to a pharmaceutical composition useful for preventing/treating pain, which comprises combination of gabapentin or pregabalin, or pharmaceutically acceptable salts thereof and N-type calcium channel antagonists or pharmaceutically acceptable salts thereof such as a compound having the following structure.

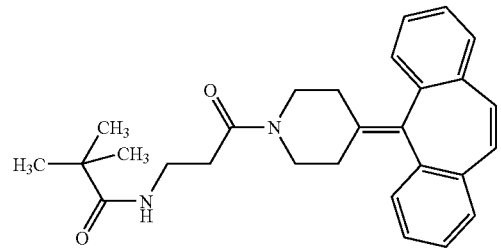

11 Claims, 3 Drawing Sheets

U.S. PATENT DOCUMENTS 6,350,766 B1 2/2002 Uneyama et al.
6,610,717 B2 8/2003 Nakajo et al.

FOREIGN PATENT DOCUMENTS

| EP | 1 099 692 | 5/2001 |
| JP | 2000-169462 | 6/2000 |
| JP | 2002-507988 | 3/2002 |
| JP | 2002-537247 | 11/2002 |
| JP | 2002-538221 | 11/2002 |
| WO | WO 98/54123 | 12/1998 |
| WO | WO 99/01437 | 1/1999 |
| WO | WO 99/07689 | 2/1999 |
| WO | WO 99/12537 | 3/1999 |
| WO | WO 99/55688 | 11/1999 |
| WO | WO 00/05210 | 3/2000 |
| WO | WO 00/00470 | 6/2000 |
| WO | WO 00/48584 | 8/2000 |
| WO | WO 00/53225 | 9/2000 |
| WO | WO 01/01983 A1 | 1/2001 |
| WO | WO 01/45709 | 6/2001 |
| WO | WO 01/76576 | 10/2001 |
| WO | WO 03/018538 | 3/2003 |
| WO | WO 03/076402 | 9/2003 |

OTHER PUBLICATIONS

U.S. Appl. No. 09/839,214, filed Apr. 23, 2001, Kito, et al.
U.S. Appl. No. 10/022,874, filed Dec. 20, 2001, Nakanishi, et al.
U.S. Appl. No. 10/025,589, filed Dec. 26, 2001, Ohno, et al.
U.S. Appl. No. 10/387,543, filed Mar. 14, 2003, Ohno, et al.
U.S. Appl. No. 10/787,175, filed Feb. 27, 2004, Yamamoto, et al.

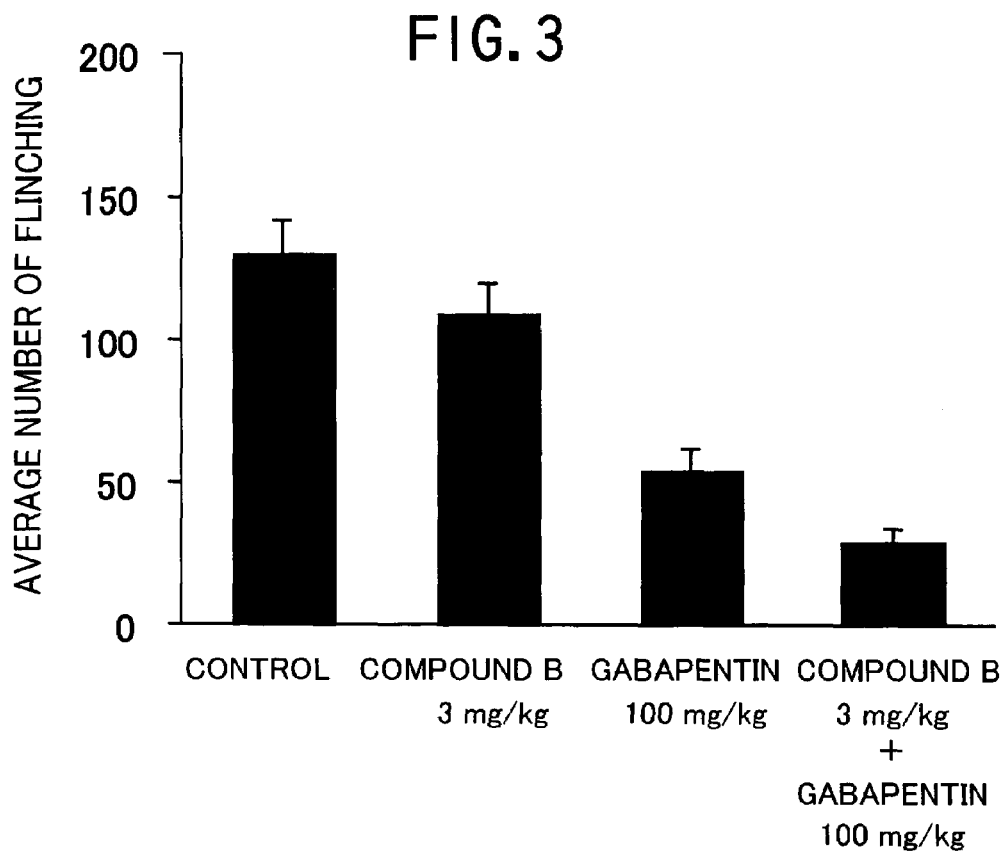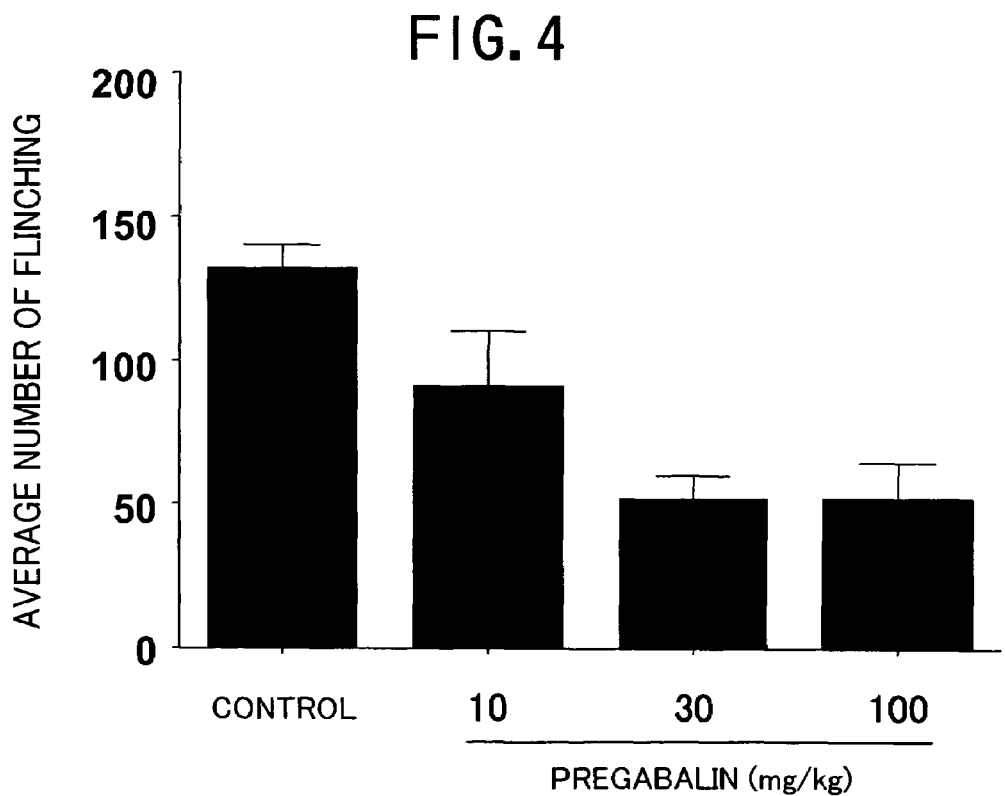

PHARMACEUTICAL COMPOSITION CONTAINING GABAPENTIN OR PREGABALIN AND N-TYPE CALCIUM CHANNEL ANTAGONIST

This application is a continuation application of International application PCT/JP03/01163, filed on Feb. 5, 2003, which claims priority to JP 2002-28208, filed on Feb. 5, 2002, JP 2002-111068, filed on Apr. 12, 2002, and JP 2002-317480, filed on Oct. 31, 2002.

BACKGROUND OF THE INVENTION

The present invention relates to a pharmaceutical composition comprising as active substances (a) gabapentin or pregabalin or pharmaceutically acceptable salts thereof and (b) N-type calcium channel antagonist or pharmaceutically acceptable salts thereof, those pharmaceutical composition is primarily effective for prevention, reduction and treatment of pain.

The present invention also relates to a method for preventing, reducing and treating pain using the above-mentioned active substances, and the use of these active substances.

Gabapentin is known to have a pain relief effect, although its mechanism of action remains elusive. Gabapentin is a derivative of γ-amino butyric acid (GABA), but it is shown not to bind to GABA receptors. Nonetheless, gabapentin can work to increase the concentration of GABA in human brain and the ratio of GABA synthesis. The GABA is an inhibitory neurotransmitter and GABA agonist has been identified as providing outstanding antiallodynia action in animal models, which suggests that gabapentin can exert its analgesic effects through the above-mentioned mode of action associated with GABA (Acta Neurol. Scand. 101:359-371, 2000). In addition, it is suggested that gabapentin can inhibit calcium current because gabapentin is shown to bind to the α2δ subunit of calcium channels. However, it is reported on one hand that gabapentin does not act on voltage-dependent calcium channels including N-type calcium channel (Epilepsy Res. 16:89-98, 1993); and it is reported on the other hand that gabapentin does not act on N-type calcium channel, but acts on P/Q type calcium channel (Br. J. Pharmacol. 130:900-906, 2000). Further, there is also a report concluding that gabapentin acts on all of N-, L- and P/Q type calcium channels (Br. J. Pharmacol. 135:257-265, 2002). As mentioned above, there are still a variety of different suggestions and a reliable theory has not yet been established.

Pregabalin is also a derivative of GABA and is known to share the pain control effectiveness. Although the mechanism of action associated with pregabalin has not yet been clarified, pregabalin is thought to increase the GABA concentration in nervous tissues in a similar manner of gabapentin. In addition, it is known that pregabalin works to liberate gabapentin from its binding site (Epilepsy Res. 34:1-41, 1999).

As is known, the N-type calcium channel antagonist has a pain control effect, too. The N-type calcium channel antagonist acts on the N-type calcium channels specifically positioned in the nerve system to inhibit calcium influx into the nerves. The N-type calcium channels, which are present at high density in presynaptic terminals of the afferent nociceptive nerve serving to transmit pain signals are concerned in transmission of the pain signals to central nervous system (Exp. Opin. Ther. Patents 8:1237-1250, 1998). The N-type calcium channel antagonist can inhibit the influx of calcium into the nerves via the N-type calcium channels to modulate release of the neurotransmitter and inhibit transmission of pain signals to central nervous system. In this way the N-type calcium channel antagonist can exhibit its analgesic action.

There are conventionally known some embodiments where gabapentin or pregabalin is used in combination with different kinds of pharmaceutical drugs, as cited in the following references and patent specifications:

(1) Combination of (a) gabapentin with (b) lamotrigine or carbamazepine (Eur. Neurol., vol. 44, 45-48, 2000)

(2) Combination of (a) gabapentin with (b) a non-NMDA antagonist, 6-cyano-7-nitroquinoxaline-2,3-dione (Anesthesiology, vol. 92, 500-506, 2000)

(3) Combination of (a) gabapentin with (b) a nonsteroidal anti-inflammatory drug, ibuprofen (Anesthesiology, vol. 91, 1006-1013, 1999)

(4) Combination of (a) gabapentin with (b) morphine (Pain, vol. 72, 375-382, 1997)

(5) Combination of (a) gabapentin or pregabalin with (b) any of an analgesic, N-methyl-D-aspartate receptor antagonist or nonsteroidal anti-inflammatory drug (WO 99/12537)

(6) Combination of (a) gabapentin or pregabalin with (b) a sodium channel inhibitor (WO 00/61188)

Nonetheless, there is not known any pharmaceutical composition comprising as active substances (a) gabapentin or pregabalin or pharmaceutically acceptable salts thereof and (b) N-type calcium channel antagonist or pharmaceutically acceptable salts thereof, and there is not recognized any effect as obtained by the use of gabapentin or pregabalin together with N-type calcium channel antagonist.

Further, WO2001/76576 discloses a pharmaceutical composition for treatment of pain and migraine, comprising (a) nicotine receptor partial agonist, (b) analgesic, and (c) pharmaceutically acceptable carrier. According to the disclosure, the component (b) of the above-mentioned pharmaceutical composition, that is, an analgesic drug, includes anticonvulsants, N-type calcium channel inhibitors or the like, wherein as the anticonvulsant gabapentin, pregabalin or the like is used. However, WO2001/76576 discloses a pharmaceutical composition for treatment of pain and migraine, characterized by comprising the three components (a), (b) and (c), and the composition can achieve its efficacy resulting from the combined use of the three components (a), (b) and (c). There is no description about a pharmaceutical composition of the present invention which comprises as active substances (a) gabapentin or pregabalin or pharmaceutically acceptable salts thereof and (b) N-type calcium channel antagonist or pharmaceutically acceptable salts thereof. No description is found that suggests the effects as obtained by the combined use of (a) gabapentin or pregabalin or pharmaceutically acceptable salts thereof with (b) N-type calcium channel antagonist or pharmaceutically acceptable salts thereof.

In the area of prevention and treatment of pain, there is an increasing demand for a significantly improved pharmaceutical drug with potentiated efficacy as compared with the conventional ones, with producing no side effects. For example, evaluation by the patients with post-herpetic neuralgia reported that the treatment effectiveness for gabapentin reached approximately 60% (Acta Neurol. Scand. 101:359-371, 2000). To further potentiate the efficacy is therefore considered to be of great significance in the treatment of pain.

Gabapentin at high doses is needed when gabapentin is used for the treatment of pain. However, it has been proved that gabapentin at high doses produce side effects such as somnolence, dizziness and ataxia (Pharmacol. Ther. 88:163-185, 2000)

Also, a significant depression of motor system has been observed in rats at high doses of pregabalin (Br. J. Pharmacol. 121: 1513-1522, 1997), and in addition, development of side effects associated with pregabalin including somnolence and dizziness has been recognized in clinical tests (Neurology. 54(S3): A421, 2000).

Accordingly, there is an increasing demand for a pain control therapy capable of lowering an incidence of side effects which are recognized in many of the currently available treatments of pain.

SUMMARY OF THE INVENTION

An object of the present invention is to provide a pharmaceutical composition for prevention, reduction and treatment of pain.

The inventors of the present invention have intensively studied to solve the above-mentioned problems, and thereafter found that administration of gabapentin in combination with N-type calcium channel antagonist can potentiate the analgesic action when compared with sole administration of gabapentin. The present invention has been thus accomplished.

In addition, the inventors have found that when pregabalin is administered in combination with N-type calcium channel antagonist, analgesic action becomes stronger as compared with the case where pregabalin is administered alone.

The combined use of drugs can offer a potential advantage over the administration of one kind of pharmaceutical drug at high doses. More specifically, when (a) gabapentin or pregabalin or pharmaceutically acceptable salts thereof is administered in combination with (b) N-type calcium channel antagonist or pharmaceutically acceptable salts thereof, each drug dose required to achieve the efficacy can be decreased, which translates to fewer side effects.

Accordingly, the present invention provides a pharmaceutical composition comprising as active substances (a) gabapentin or pregabalin or pharmaceutically acceptable salts thereof and (b) N-type calcium channel antagonist or pharmaceutically acceptable salts thereof.

The present invention also provides a pharmaceutical composition for prevention, reduction and treatment of pain, comprising as active substances (a) gabapentin or pregabalin or pharmaceutically acceptable salts thereof and (b) N-type calcium channel antagonist or pharmaceutically acceptable salts thereof.

In addition, the present invention provides a method for preventing, reducing and treating pain, comprising the step of administering to mammals both active substances of (a) gabapentin or pregabalin or pharmaceutically acceptable salts thereof in an effective amount so as to achieve efficacy in preventing, reducing and treating pain and (b) N-type calcium channel antagonist or pharmaceutically acceptable salts thereof in an effective amount so as to achieve efficacy in preventing, reducing and treating pain.

Further, the present invention provides use of (a) gabapentin or pregabalin or pharmaceutically acceptable salts thereof and (b) N-type calcium channel antagonist or pharmaceutically acceptable salts thereof for preparation of a pharmaceutical drug for preventing, reducing and treating pain.

BRIEF DESCRIPTION OF THE DRAWINGS

FIG. 3 shows the analgesic effects of each of compound B, gabapentin and "combination of compound B and gabapentin" in the formalin test.

FIG. 4 shows the analgesic effect of pregabalin in the formalin test.

BEST MODE FOR CARRYING OUT THE INVENTION

Figure 1:
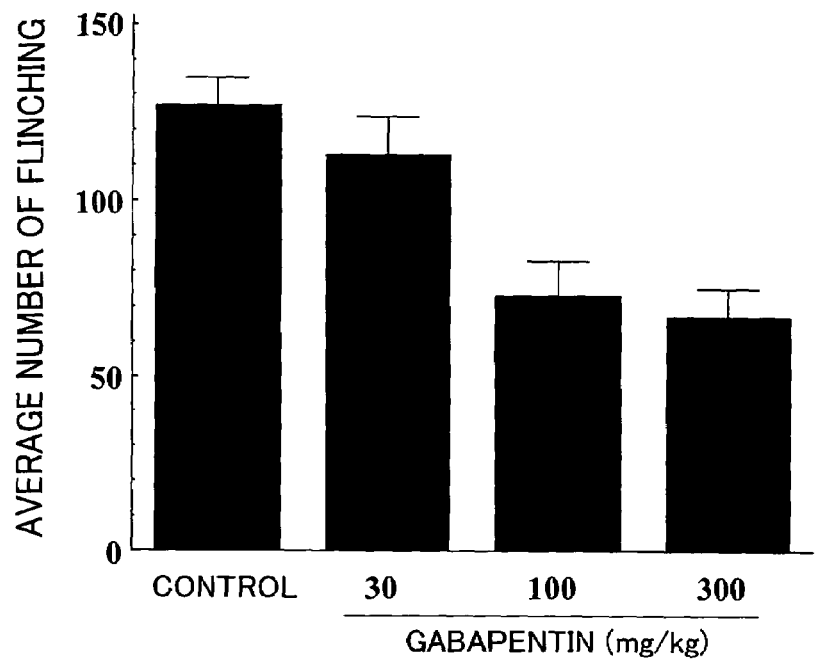
FIG. 1 shows the analgesic effect of gabapentin in the formalin test.

"Gabapentin" and "pregabalin", which are the active ingredients of the present invention, are genetic terms. The chemical names thereof are 1-(aminomethyl)-cyclohexaneacetic acid and (S)-3-(aminomethyl)-5-methylhexanoic acid respectively.

"N-type calcium channel antagonists", which are the active ingredients of the present invention, refer to agents which inhibit influx of calcium into nerves by acting on N-type calcium channel that exists specifically in nerves.

Examples of "N-type calcium channel antagonists" are the following compounds shown in (I) to (X) or pharmaceutically acceptable salts thereof.

The compounds of (I) are new N-type calcium channel antagonists. On the other hand, the compounds of (II) to (X) are known N-type calcium channel antagonists and the chemical structural formulae thereof are shown in Tables 1 and 2. Those compounds are described in the references and patents in the Tables.

TABLE 1

| No. | Chemical Structure | Name of the Compound | References & Patents |
|---|---|---|---|
| II | 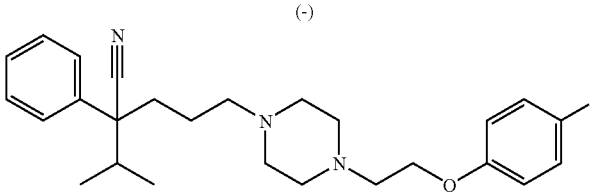 | (−)-1-[(4-cyano-5-methyl-4-phenyl) hexyl]-4-[2-(4-fluorophenoxy)ethyl] piperazine | JP-A-2000-169462 |

TABLE 1-continued

| No. | Chemical Structure | Name of the Compound | References & Patents |
|---|---|---|---|
| III | 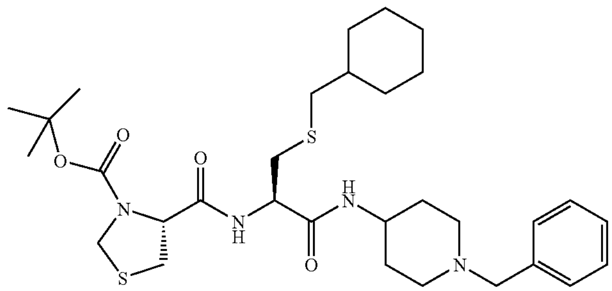 | (2R)-N-(1-benzylpiperidine-4-yl)-3-cyclohexyl methylthio-2-((4R)-3-t-butoxycarbonyl thiazolidine-4-yl carbonylamino) propanamide | WO00/00470 |
| IV | 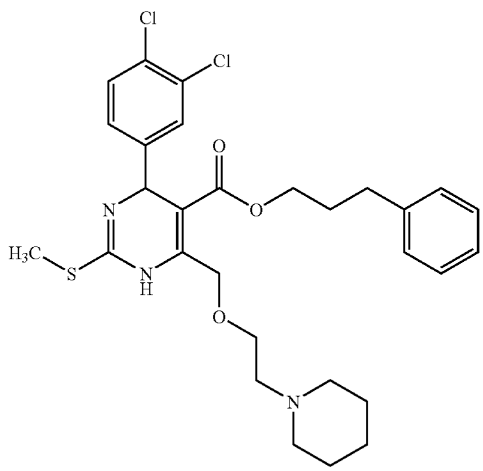 | 3-phenylpropyl 4-(3,4-dichlorophenyl)-2-methylthio-6-[(2-(1-piperidinyl)ethoxy)methyl]-1,4-dihydropyrimidine-5-carboxylate | WO099/01437 |
| V | 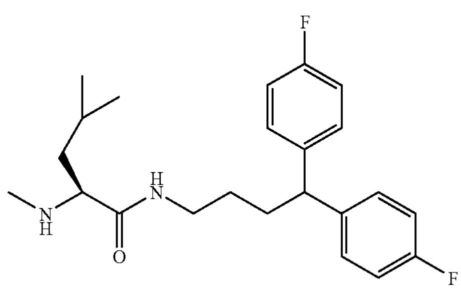 | (S)-4-methyl-2-methyl aminopentanoic acid [4,4-bis(4-fluorophenyl)butyl]amide | WO099/55688 |

TABLE 2

| No. | Chemical Structure | Name of the Compound | Reference & Patents |
|---|---|---|---|
| VI | 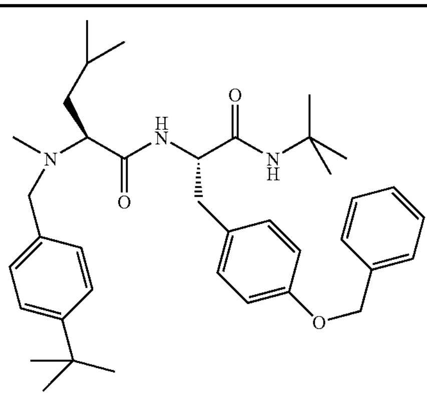 | [S-(R*, R*)]-2-[(4-tert-butylbenzyl)methylamino]-4-methylpentanoic acid [2-(4-benzyloxyphenyl)-1-tert-butylcarbamoylethyl]amide | WO98/54123 |

TABLE 2-continued

| No. | Chemical Structure | Name of the Compound | Reference & Patents |
|---|---|---|---|
| VII | 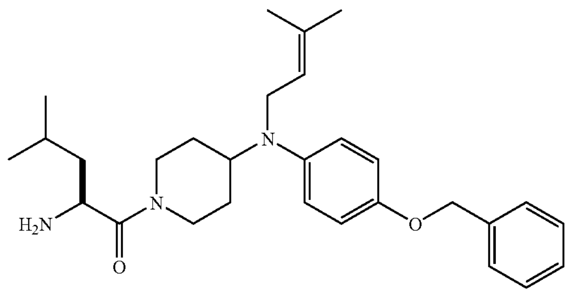 | (S)-2-amino-1-{4-[(4-benzyloxyphenyl)-(3-methyl-2-butene-1-yl)amino]piperidine-1-yl}-4-methylpentane-1-one | JMC, 1999, 42, 4239. WO99/07689 |
| VIII | 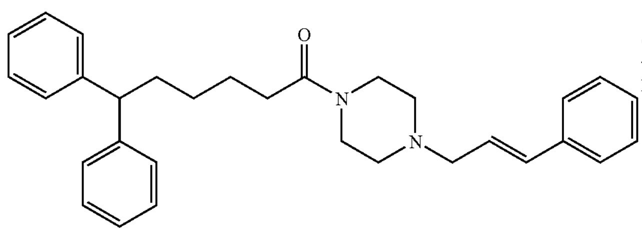 | 1-(6,6-diphenylhexanoyl)-4-[(2E)-3-phenyl-2-propenyl]piperazine | WO00/45709 |
| IX | 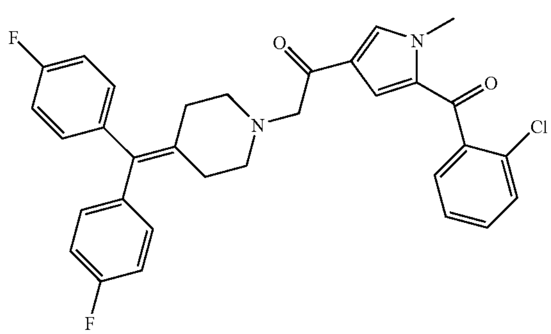 | 2-{4-[bis(4-fluorophenyl)methylene]piperidine-1-yl}-1-[5-(2-chlorobenzoyl)-1-methyl-1H-pyrrole-3-yl]ethanone | WO00/48584 |
| X | 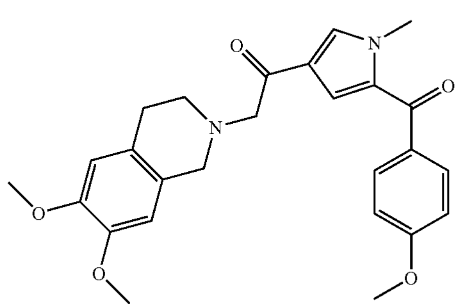 | 2-(6,7-dimethoxy-3,4,dihydro-1H-isoquinoline-2-yl)-1-[5-(4-methoxybenzoyl)-1-methyl-1H-pyrrole-3-yl]ethanone | WO00/48584 |

It is preferable that N-type calcium channel antagonists, as the active ingredients of the present invention, are the compounds of the following (I) or pharmaceutically acceptable salts thereof:

(I): The compounds of the following general formula (1), (2), (3) or (4), or pharmaceutically acceptable salts thereof:

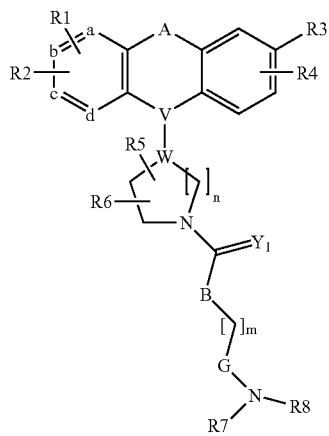
(1)

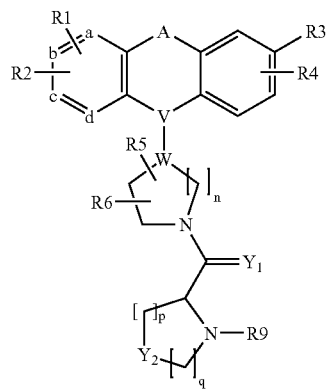
(2)

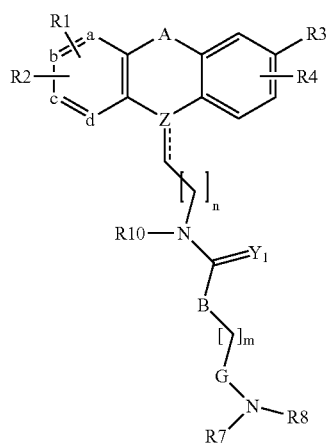
(3)

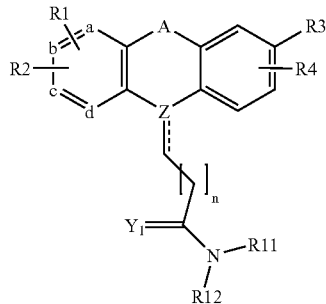
(4)

wherein A represents —CH=CH—, —CH$_2$—CH$_2$—, —S—, —CH$_2$—S—, —S—CH$_2$—, —O—, —CH$_2$—O—, —O—CH$_2$—, —N(R$^{17}$)—CH$_2$—, —CH$_2$—N(R$^{17}$)—, —CH=CH—CH$_2$—, —CH$_2$—CH=CH—, —CH$_2$—CH$_2$—CH$_2$—, —N(R$^{17}$)—(CO)—, —(CO)—N(R$^{17}$)—, —(CO)—, —(SO)— or —C(R$^{18}$R$^{19}$)— wherein R$^{17}$ represents H, a lower alkyl or an aryl, and R$^{18}$ and R$^{19}$ are each independently selected from the group consisting of H, a lower alkyl, an aryl and —C(O)OR$^{15}$ wherein R$^{15}$ represents a lower alkyl or an aryl;

a, b, c and d are each independently selected from the group consisting of CR$^1$ and CR$^2$;

or one of a, b, c and d is N;

R$^1$, R$^2$ and R$^4$ each independently represent H, a halogen, —CF$_3$, —OR$^{14}$, —COR$^{14}$, —SR$^{14}$, —S(O)$_t$R$^{15}$, —N(R$^{14}$)$_2$, —NO$_2$, —OC(O)R$^{14}$, —CO$_2$R$^{14}$, —OCO$_2$R$^{14}$, —CN, —NR$^{14}$COOR$^{15}$, —SR$^{15}$C(O)OR$^{15}$ or —SR$^{15}$N(R$^{16}$)$_2$ wherein R$^{14}$ represents H, a lower alkyl, an aryl or an aryl-lower alkyl group, R$^{15}$ represents a lower alkyl or an aryl group, R$^{16}$ is independently selected from the group consisting of H and —C(O)OR$^{15}$, and t represents 1 or 2;

R$^3$ represents H;

V—W represents C=C, CH—CH, CH—N or N—CH;

Z is selected from the group consisting of C, CH and N (with the proviso that when Z is C, the bond represented by a dotted line represents a double bond and when Z is CH or N, the bond represented by the dotted line represents a single bond;

n represents 0 to 3;

R$^5$ and R$^6$ each independently represent H, a halogen, —CF$_3$, a lower alkyl or an aryl;

or R$^5$ and R$^6$ together form =O or =S;

Y$^1$ represents O or S;

B represents NR$^{17a}$, —NR$^{17a}$(CH$_2$)$_v$CHR$^{21}$—, —(CH$_2$)$_v$CHR$^{21}$— wherein v represents 0 to 3, R$^{17a}$ represents H, a lower alkyl or an aryl, R$^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, —(CH$_2$)$_w$—COOR$^{29}$, —(CH$_2$)$_w$—NR$^{29}$R$^{30}$ wherein R$^{29}$ and R$^{30}$ each independently represent hydrogen atom or a lower alkyl group, and w represents 0 to 4, —(CH)$_3$NHC(NH)=NH, benzyl, 4-hydroxybenzyl, 3-indoylmethyl or 5-imidazoylmethyl;

G represents —(CO)—, —(SO)—, —(SO)— or a covalent bond;

m represents 0 to 6;

Y$^2$ represents C or S;

p and q are each independently selected from the group consisting of 1, 2 and 3;

$R^7$ and $R^8$ each represent H, a lower alkyl, an aryl, —(CO)$R^{18a}$, —(CS)$R^{18a}$, —(CO)$NR^{18a}R^{19a}$, —(CS)$NR^{18a}R^{19a}$ wherein $R^{18a}$ represents H, a lower alkyl, an aryl or a cycloalkyl group which may have a hetero atom in the ring, $R^{19a}$ represents H, a lower alkyl or an aryl; or $R^{18a}$ and $R^{19a}$ together form a cycloalkyl which may have a halogen, —$CF_3$, a lower alkyl or an aryl as a substituent, —(CO)$OR^{20}$—(CS)$OR^{20}$ or wherein $R^{20}$ represents an alkyl group having 1 to 12 carbon atoms, an aryl group or a cycloalkyl group which may have a hetero atom in the ring, or a group of the following general formula (5):

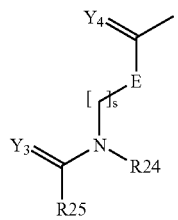

(5)

wherein $Y^4$ and $Y^3$ each represent O or S; s represents 0 to 6; E represents $NR^{22}$ or $CHR^{23}$ wherein $R^{22}$ represents H, a lower alkyl or aryl; and $R^{23}$ represents H, a lower alkyl, an aryl, a hydroxyl-lower alkyl, —$CH_2SH$, —$CH_2CH_2SCH_3$, —$CH_2(CO)NH_2$, —$CH_2CH_2(CO)NH_2$, —$CH_2COOH$, —$CH_2CH_2COOH$, —$(CH_2)_4NH_2$, —$(CH)_3NHC(NH)$=NH, benzyl, 4-hydroxybenzyl, 3-indoylmethyl or 5-imidazoylmethyl;

$R^{24}$ represents H, a lower alkyl or an aryl;

$R^{25}$ represents H, a lower alkyl, an aryl, —$OR^{18a}$, —(CO)$R^{18a}$, —(CS)$R^{18a}$, —(CO)$NR^{18a}R^{19a}$, —(CS)$NR^{18a}R^{19a}$, —(CO)$OR^{20}$ or —(CS)$OR^{20}$ wherein $R^{18a}$, $R^{19a}$ and $R^{20}$ are as defined above, $R^9$ represents H, a lower alkyl, an aryl, —(CO)$R^{18a}$, —(CS)$R^{18a}$, —(CO)$NR^{18a}R^{19a}$, —(CS)$NR^{18a}R^{19a}$, —(CO)$OR^{20}$ or —(CS)$OR^{20}$ wherein $R^{18a}$, $R^{19a}$ and $R^{20}$ are as defined above;

$R^{10}$ represents H, a lower alkyl or an aryl;

$R^{11}$ represents H, a lower alkyl or an aryl;

$R^{12}$ represents H, a lower alkyl, an aryl, —(CO)$R^{18a}$, —(CS)$R^{18a}$, —(CO)$NR^{18a}R^{19a}$, —(CS)$NR^{18a}R^{19a}$, —(CO)$OR^{20}$ or —(CS)$OR^{20}$ wherein $R^{18a}$, $R^{19a}$ and $R^{20}$ are as defined above, or a substituent represented by the following general formula (6):

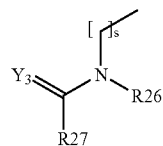

(6)

wherein s represents 1 to 6;

$Y^3$ represents O or S, $R^{26}$ represents H, a lower alkyl or an aryl;

$R^{27}$ represents H, a lower alkyl, an aryl, —$OR^{18a}$, —(CO)$R^{18a}$, —(CS)$R^{18a}$, —(CO)$NR^{18a}R^{19a}$, —(CS)$NR^{18a}R^{19a}$, —(CO)$OR^{20}$ or —(CS)$OR^{20}$ wherein $R^{18a}$, $R^{19a}$ and $R^{20}$ are as defined above;

or $R^{11}$ and $R^{12}$ form a substituent represented by the following general formula (7) together with the nitrogen atom:

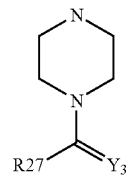

(7)

wherein $Y^3$ represents O or S, and $R^{27}$ is as defined above.

The term "lower" of the present invention indicates that the group has 1 to 6 carbon atoms. Alkyl groups themselves and also alkyl groups in alkenyl groups, alkynyl groups, alkoxyl groups, alkylamino groups, alkylthio groups, alkanoyl groups and the like may be either linear or branched. Examples of these alkyl groups are methyl group, ethyl group, propyl group, isopropyl group, butyl group, pentyl group, hexyl group, and secondary and tertiary butyl groups. In them, those having 1 to 4 carbon atoms are preferred. The aryl-lower alkyl groups include, for example, benzyl groups. The hetero atoms include nitrogen, oxygen, sulfur, etc. The halogen atoms include fluorine, chlorine, bromine and iodine. In the present specification, the aryl groups are both substituted and unsubstituted aryl groups. They are preferably phenyl groups and substituted phenyl groups, and the substituents thereof are preferably halogens, alkyl groups and alkoxyl groups. The cycloalkyl groups include, for example, cyclopentyl group and cyclohexyl group. The cycloalkyl groups which may have a hetero atom in the ring include tetrahydropyranyl group, piperidyl group, pyrrolidinyl group and piperazinyl group.

In the general formulae (1), (2), (3) and (4) of the above (I), groups represented by A are preferably —CH=CH—, —$CH_2$—$CH_2$—, —S—, —$CH_2$—S— and —S—$CH_2$—. They are particularly preferably —CH=CH—.

Each of a, b, c and d is independently preferably CH.

Each of $R^1$ to $R^4$ is preferably hydrogen atom.

The group represented by V—W is preferably selected from the group consisting of C=C, CH—CH, CH—N and N—CH. It is particularly preferably C=C.

The group represented by Z is preferably selected from the group consisting of C, CH and N (with the proviso that when Z is C, the bond represented by a dotted line represents a double bond and when Z is CH or N, the bond represented by the dotted line represents a single bond). Z is particularly preferably C.

n preferably represents 1 or 2. It is particularly preferably 2.

Preferably, $R^5$ and $R^6$ are each hydrogen atom or they together form =O.

$Y^1$ preferably represents oxygen atom.

$R^{17a}$ in $NR^{17a}$ and —$NR^{17a}(CH^2)_v CHR^{21}$— represented by B is preferably hydrogen atom, and $R^{21}$ in —$NR^{17a}(CH_2)_v CHR^{21}$— and —$(CH_2)_v CHR^{21}$— is preferably hydrogen atom or hydroxymethyl group. B is particularly preferably —$(CH_2)_v CHR^{21}$—. "v" is preferably 0 to 3, particularly 2 or 3.

The group represented by G is preferably —(CO)— or a covalent bond.

m represents 0 to 6, preferably 0 to 3.

Preferably p and q each independently represent 1, and $Y^2$ represents carbon atom or sulfur atom.

$R^7$ and $R^8$ are preferably hydrogen atom, a lower alkyl, an aryl, —(CO)$R^{18a}$, —(CO)$NR^{18a}R^{19a}$ or —(CO)$OR^{20}$. $R^{18a}$ is preferably a lower alkyl, particularly preferably methyl group, ethyl group, isopropyl group or secondary or tertiary butyl group. $R^{19a}$ is preferably hydrogen atom or a lower alkyl group. It is also preferred that $R^{18a}$ and $R^{19a}$ together form a cycloalkyl group. $R^{20}$ is preferably a lower alkyl group, particularly preferably methyl group, ethyl group, isopropyl group or secondary or tertiary butyl group.

Further, $R^7$ and $R^8$ are preferably a group represented by the above general formula (5) wherein s is preferably 0 to 2, E is preferably $CHR^{23}$ wherein $R^{23}$ preferably represents H, and $Y^3$ and $Y^4$ each represent O; $R^{24}$ preferably represents H, and $R^{25}$ preferably represents —$OR^{20}$ or —$(CO)OR^{20}$;

$R^9$ preferably represents —$(CO)OR^{20}$;

$R^{10}$ preferably represents H;

$R^{11}$ preferably represents H;

$R^{12}$ preferably represents a substituent represented by the above general formula (6) wherein s preferably represents 2 or 3; $Y^3$ preferably represents O; $R^{26}$ preferably represents H; and $R^{27}$ preferably represents —$OR^{20}$ or —$(CO)OR^{20}$; or $R^{11}$ and $R^{12}$ preferably represent a substituent represented by the above general formula (7) together with nitrogen atom, wherein $Y^3$ preferably represents O and $R^{27}$ preferably represents —$OR^{20}$ or —$(CO)OR^{20}$.

Further, when asymmetric carbon atoms are included, the configuration thereof is preferably R, S or their mixture.

Preferred diarylalkene derivatives, diarylalkyl derivatives and pharmaceutically acceptable salts of them are also those of the above general formulae (1), (2), (3) and (4) wherein the group represented by V—W is preferably C═C, CH—CH or N—CH;

Z is selected from the group consisting of C, CH and N (with the proviso that when Z is C, the bond represented by a dotted line represents a double bond and when Z is CH or N, the bond represented by the dotted line represents a single bond);

B represents $NR^{17a}$, $CHR^{21}$ and $CH_2CHR^{21}$ wherein $R^{17a}$ represents H, a lower alkyl or an aryl, $R^{21}$ represents H, a lower alkyl, an aryl, a hydroxyl-lower alkyl, —$CH_2SH$, —$CH_2CH_2SCH_3$, —$CH_2(CO)NH_2$, —$CH_2CH_2(CO)NH_2$, —$CH_2COOH$, —$CH_2CH_2COOH$, —$(CH_2)_4NH_2$, —$(CH_2)_3NHC(NH_2)$═NH, benzyl, 4-hydroxybenzyl, 3-indoylmethyl or 5-imidazoylmethyl;

$R^{18a}$ represents H, a lower alkyl or an aryl, and $R^{19a}$ represents H, a lower alkyl or aryl; or $R^{18a}$ and $R^{19a}$ together form a cycloalkyl group which may have a halogen, —$CF_3$, a lower alkyl or an aryl as a substituent, and $R^{25}$ and $R^{27}$ each represent H, a lower alkyl, an aryl, —$(CO)R^{18a}$, —$(CS)R^{18a}$, —$(CO)N^{18a}R^{19a}$, —$(CS)NR^{18a}R^{19a}$, —$(CO)OR^{20}$ or —$(CS)OR^{20}$.

Preferred diarylalkene derivatives, diarylalkyl derivatives and pharmaceutically acceptable salts of them are also those of the above general formulae (1), (2), (3) and (4) wherein:

A represents —CH═CH—, —$CH_2$—$CH_2$—, —S—, —$CH_2$—S— or —S—$CH_2$—;

a, b, c and d each represent CH;

$R^3$ and $R^4$ each represent hydrogen atom;

$R^5$ and $R^6$ each represent hydrogen atom;

or $R^5$ and $R^6$ together form ═O;

n represents 1 or 2;

$Y^1$ represents O;

B represents $NR^{17a}$, $CHR^{21}$ or, $CH_2CHR^{21}$ wherein $R^{21}$ represents H, a lower alkyl, an aryl or —$CH_2OH$;

G represents —(CO)— or a covalent bond;

m represents 0 to 6;

p and q are each 1;

$R^7$ and $R^8$ each independently represent H, a lower alkyl, an aryl, —$(CO)R^{18a}$ wherein $R^{18a}$ represents H, a lower alkyl or an aryl, —$(CO)NR^{18a}R^{19a}$ wherein $R^{19a}$ represents H, a lower alkyl or an aryl; or $R^{18a}$ and $R^{19a}$ together form a cycloalkyl which may have a halogen, —$CF_3$, a lower alkyl or an aryl as a substituent, —$(CO)OR^{20}$ wherein $R^{20}$ represents an alkyl group having 1 to 12 carbon atoms, an aryl group or a cycloalkyl group which may contain a hetero atom in the ring, or a group of the following general formula (8):

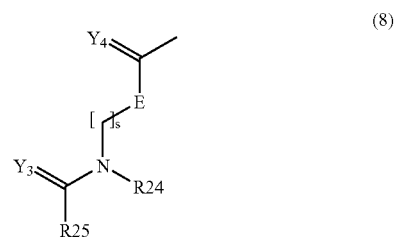

[wherein $Y^4$ and $Y^3$ each represent O;

s represents 1 or 2;

E represents $CHR^{23}$ wherein $R^{23}$ represents H, $R^{24}$ represents H;

$R^{25}$ represents —$(CO)OR^{20}$;]

$R^9$ represents —$(CO)OR^{20}$;

$R^{10}$ represents H;

$R^{11}$ represents H;

$R^{12}$ represents a substituent represented by the following general formula (9);

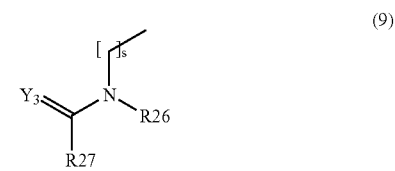

wherein s represents 2 or 3;

$Y^3$ represents O;

$R^{26}$ represents H; and $R^{27}$ represents —$(CO)OR^{20}$, or $R^{11}$ and $R^{12}$ form a substituent represented by the following general formula (10) together with the nitrogen atom:

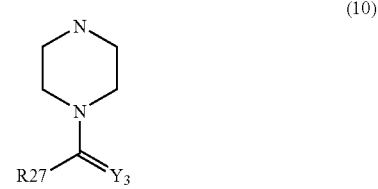

Preferred diarylalkene derivatives, diarylalkyl derivatives and pharmaceutically acceptable salts of them are also those of the general formula (1) wherein A represents —CH═CH— or —$CH_2$—$CH_2$—, a, b, c and d each represent CH;

$R^1$ and $R^2$ each represent H;

$R^3$ and $R^4$ each represent H;

V—W represents C═C;

n represents 2;

$R^5$ and $R^6$ each represent H; and $Y^1$ represents O.

Preferred diarylalkene derivatives, diarylalkyl derivatives and pharmaceutically acceptable salts of them are also those of the above general formulae (1), (2), (3) and (4) wherein:

V—W represents C═C, CH—CH or N—CH;

Z is selected from the group consisting of C, CH and N (with the proviso that when Z is C, the bond represented by a dotted line represents a double bond and when Z is CH or N, the bond represented by the dotted line represents a single bond);

B represents —(CH$_2$)$_v$—CHR$^{21}$ wherein v represents 2 or 3, R$^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, benzyl, 4-hydroxybenzyl, 3-indoylmethyl or 5-imidazoylmethyl;

R$^{18a}$ represents H, a lower alkyl or an aryl, and R$^{19a}$ represents H, a lower alkyl or aryl; or R$^{18a}$ and R$^{19a}$ together form a cycloalkyl group which may have a halogen, —CF$_3$, a lower alkyl or an aryl as a substituent.

Preferred diarylalkene derivatives, diarylalkyl derivatives and pharmaceutically acceptable salts of them are also those of the general formula (1) wherein:

A represents —CH═CH— or —CH$_2$—CH$_2$—, a, b, c and d each represent CH;

R$^1$, R$^2$, R$^3$, R$^4$, R$^5$ and R$^6$ each represent H;

V—W represents C═C;

m represents 0, n represents 2;

Y$^1$ represents O, G represents a covalent bond, and R$^7$ and R$^8$ each independently represent H, a lower alkyl, —(CO)OR$^{18a}$ wherein R$^{18a}$ represents H, a lower alkyl or an aryl, —(CO)OR$^{20}$ wherein R$^{20}$ represents an alkyl group having 1 to 12 carbon atoms or an aryl.

In the present invention, diarylalkene derivatives, diarylalkyl derivatives of the following general formula (11) and pharmaceutically acceptable salts thereof are further preferred:

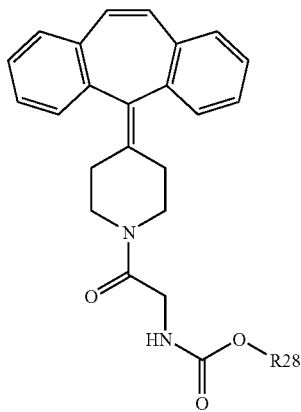

(11)

wherein R$^{28}$ represents an alkyl group having 1 to 12 carbon atoms, a cycloalkyl group having 1 to 12 carbon atoms or a cycloalkyl group which may have a hetero atom in the ring; R$^{28}$ is preferably a branched alkyl group, particularly a branched alkyl group having 3 to 8 carbon atoms.

In the present invention, particularly preferred diarylalkene derivatives, diarylalkyl derivatives and pharmaceutically acceptable salts thereof in those compounds are those of the general formula (1) wherein:

A represents —CH═CH— or —CH$_2$—CH$_2$—;

a, b, c and d each represent CH;

R$^1$, R$^2$, R$^3$, R$^4$, R$^5$ and R$^6$ each represent H;

V—W represents C═C;

Z represents C, and the bond represented by a dotted line represents a double bond;

n represents 2; and

Y$^1$ represents O.

In the compounds of the general formulae (1) to (4) in the present invention, preferred compounds are those of general formula (1) and more preferred compounds are those having the above-described preferred groups.

It is further preferable that N-type calcium channel antagonists, as the active ingredients of the present invention, are the compounds of the following general formula (1-A) or pharmaceutically acceptable salts thereof:

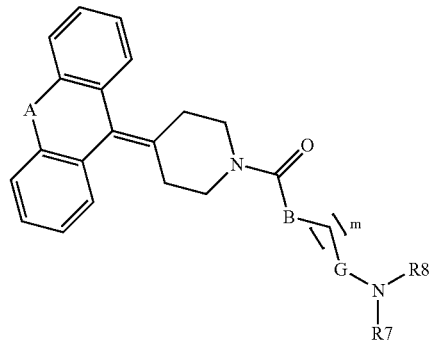

(1-A)

wherein A represents —CH═CH—, —CH$_2$—CH$_2$— or —S—;

B represents —(CH$_2$)$_v$—CHR$^{21}$— wherein v represents 0 to 3, R$^{21}$ represents H, a lower alkyl, an aryl, a hydroxyl-lower alkyl, —(CH$_2$)$_w$—COOR$^{29}$ or —(CH)$_w$—NR$^{29}$R$^{30}$ wherein R$^{29}$ and R$^{30}$ each independently represent hydrogen atom or a lower alkyl group and w represents 0 to 4;

G represents —(CO)— or a covalent bond;

m represents 0 to 6; and

R$^7$ and R$^8$ each independently represent H, a lower alkyl, an aryl, —(CO)R$^{18a}$ wherein R$^{18a}$ represents H, a lower alkyl, an aryl or a cycloalkyl group which may contain a hetero atom in the ring, or —(CO)OR$^{20}$ wherein R$^{20}$ represents an alkyl group having 1 to 12 carbon atoms, an aryl or a cycloalkyl group which may have a hetero atom in the ring.

It is also preferable that N-type calcium channel antagonists, which are the active ingredients of the present invention, or pharmaceutically acceptable salts thereof are the following compounds (1-B) or pharmaceutically acceptable salts thereof:

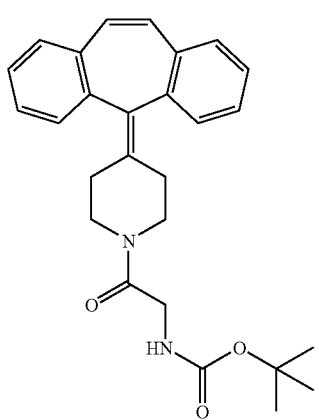

(1-B)

-continued
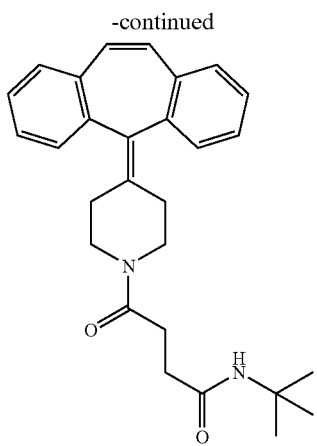
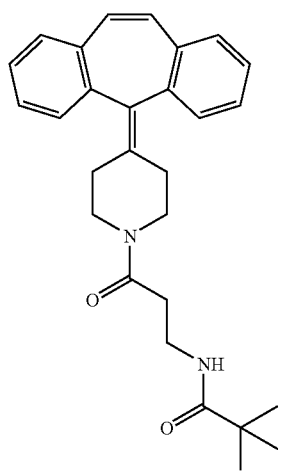
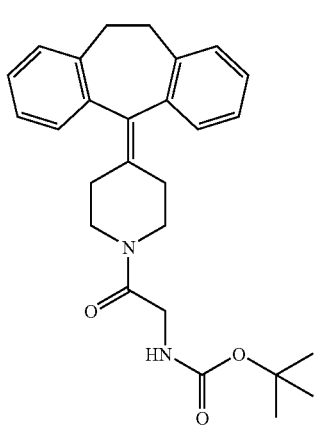
-continued
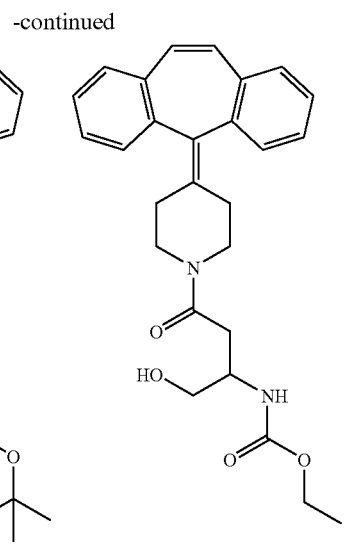
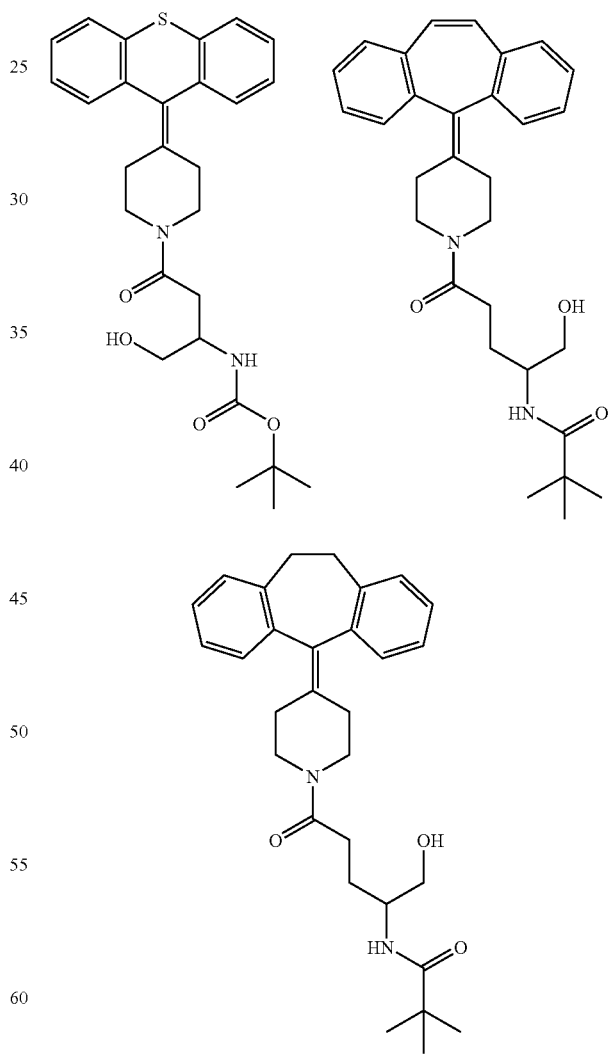
The compounds of the following formulae, analogues of them or pharmaceutically acceptable salts of them are particularly preferred.

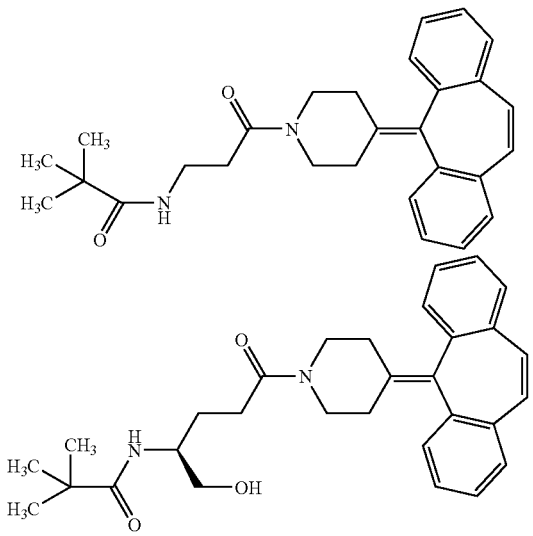

It is also preferable that N-type calcium channel antagonists, as the active ingredients of the present invention, or pharmaceutically acceptable salts thereof are the compounds of the following (II) to (X) shown in Tables 1 and 2 or pharmaceutically acceptable salts thereof:

(II): (−)-1-[(4-cyano-5-methyl-4-phenyl)hexyl]-4-[2-(4-fluorophenoxy)ethyl] piperazine or pharmaceutically acceptable salts thereof:

(III): (2R)-N-(1-benzylpiperidine-4-yl)-3-cylohexyl methylthio-2-((4R)-3-t-butoxycarbonyl thiazolidine-4-ylcarbonylamino) propanamide or pharmaceutically acceptable salts thereof:

(IV): 3-phenylpropyl 4-(3,4-dichlorophenyl)-2-methylthio-6-[(2-(1-piperidinyl)ethoxy)methyl]-1,4-dihydropyrimidine-5-carboxylate or pharmaceutically acceptable salts thereof:

(V): (S)-4-methyl-2-methylaminopentanoic acid [4,4-bis(4-fluorophenyl)butyl]amide or pharmaceutically acceptable salts thereof:

(VI): [S-(R*, R*)]-2-[(4-tert-butylbenzyl)methylamino]-4-methylpentanoic acid [2-(4-benzyloxyphenyl)-1-tert-butylcarbamoylethyl]amide or pharmaceutically acceptable salts thereof:

(VII): (S)-2-amino-1-{4-[(4-benzyloxyphenyl)-(3-methyl-2-butene-1-yl)amino]piperidine-1-yl}-4-methylpentane-1-one or pharmaceutically acceptable salts thereof:

(VIII): 1-(6,6-diphenylhexanoyl)-4-[(2E)-3-phenyl-2-propenyl]piperazine or pharmaceutically acceptable salts thereof:

(IX): 2-{4-[bis(4-fluorophenyl)methylene]piperidine-1-yl}-1-[5-(2-chlorobenzoyl)-1-methyl-1H-pyrrole-3-yl] ethanone or pharmaceutically acceptable salts thereof:

(X): 2-(6,7-dimethoxy-3,4-dihydro-1H-isoquinoline-2-yl)-1-[5-(4-methoxybenzoyl)-1-methyl-1H-pyrrole-3-yl] ethanone or pharmaceutically acceptable salts thereof.

In the pharmaceutical compounds for preventing, redressing or treating pain comprising (a) gabapentin or pregabalin, or pharmaceutically acceptable salts thereof and (b) N-type calcium channel antagonists or pharmaceutically acceptable salts thereof as active ingredients, the N-type calcium channel antagonists are preferably the compounds of the above general formulae (I) to (X), (1-A), the compounds in (1-B) or pharmaceutically acceptable salts thereof. They are particularly preferably the compounds of the general formulae (II) to (X), the compounds in (1-B) or pharmaceutically acceptable salts thereof.

In the methods for preventing, redressing or treating pain comprising administering to mammals (a) effective dosages of gabapentin or pregabalin, or pharmaceutically acceptable salts thereof for preventing, redressing or treating pain and (b) effective dosages of the above compounds or pharmaceutically acceptable salts thereof for preventing, redressing or treating pain as active ingredients, the N-type calcium channel antagonists are preferably the compounds of the above general formulae (I) to (X), (1-A), the compounds in (1-B) or pharmaceutically acceptable salts thereof. They are particularly preferably the compounds of the general formulae (11) to (X), the compounds in (1-B) or pharmaceutically acceptable salts thereof.

In the use of (a) gabapentin or pregabalin, or pharmaceutically acceptable salts thereof and (b) N-type calcium channel antagonists or pharmaceutically acceptable salts thereof for preparing medicine for preventing, redressing or treating pain, the N-type calcium channel antagonists are preferably the compounds of the above general formulae (I) to (X), (1-A), the compounds in (1-B) or pharmaceutically acceptable salts thereof. They are particularly preferably the compounds of the general formulae (II) to (X), the compounds in (1-B) or pharmaceutically acceptable salts thereof.

The pharmaceutical composition of the present invention may be used for preventing, redressing or treating pain.

"Pain" is defined as the feeling or emotional experience of discomfort which is related to a substantive or potential disorder of tissues or is represented by the terms of such disorders. Examples of pain are acute pain such as toothache, operative pain, post-operative pain, obstetric pain and muscle pain; chronic inflammatory pain associated with rheumatoid arthritis and osteoarthritis and the like; neuropathic pain such as trigeminal neuralgia, post-herpetic neuralgia or pain caused by HIV infection, diabetic neuropathy, phantom limb pain and causalgia; cancer pain; visceral pain; psychogenic pain; back pain and reflex sympathetic dystrophy. The pharmaceutical compositions of the present invention may be used as agents for preventing, redressing or treating migraine or chronic headache.

Gabapentin or pregabalin and N-type calcium channel antagonists, which are the active ingredients of the present invention, may form pharmaceutically acceptable salts thereof. For example, they include ammonium salts, salts thereof with alkali metals, e.g. sodium and potassium, salts thereof with alkaline earth metals, e.g. calcium and magnesium, salts thereof with aluminum or zinc, salts thereof with organic amines, e.g. morpholine and piperidine, salts thereof with basic amino acids, e.g. arginine and lysine, salts thereof with inorganic acids, e.g. hydrochloric acid, sulfuric acid, nitric acid, hydrobromic acid and phosphoric acid, salts thereof with organic acids, e.g. oxalic acid, maleic acid, tartaric acid, fumaric acid, and succinic acid, salts thereof with sulfonic acids, e.g. methanesulfonic acid, benzenesulfonic acid and p-toluenesulfonic acid.

The pharmaceutical compositions of the present invention may be obtained by combining (a) gabapentin or pregabalin, or pharmaceutically acceptable salts thereof and (b) N-type calcium channel antagonists or pharmaceutically acceptable salts thereof as active ingredients. These active ingredients may be prepared as drugs separately or at one time by mixing with a pharmaceutically acceptable carrier(s) in accordance with an ordinary method.

The dosage forms of the pharmaceutical compositions of the present invention are, for example, oral agents such as tablets, powders, pills, granules, capsules and syrups; injectable solutions such as subcutaneously-injected solutions, intravenously-injected solutions, intramuscular medication, solutions injected into peridural space and solutions injected into subarachnoidal space; external drugs such as intranasal drugs, percutaneously-administered drugs and ointments; suppositories such as rectal suppositories and vaginal suppositories; and drops. The examples of appropriate pharmaceutical carriers are cellulose derivatives such as carboxymethyl cellulose and ethylcellulose; starches such as potato starch and corn starch; sugars such as lactose and sucrose; vegetable oils such as peanut oil, corn oil and sesame oil; polyethyleneglycol, alginic acids, gelatin and talc.

The pharmaceutical compositions of the present invention could be sufficient to be the ones, when they are administered, combining (a) gabapentin or pregabalin, or pharmaceutically acceptable salts thereof and (b) N-type calcium channel antagonists or pharmaceutically acceptable salts thereof as active ingredients. Namely, (a) gabapentin or pregabalin, or pharmaceutically acceptable salts thereof and (b) N-type calcium channel antagonists or pharmaceutically acceptable salts thereof as active ingredients of the present invention may be administered at the same time or administered sequentially at time intervals. When administered at the same time, each active ingredient of the present invention may be administered in the form of a single drug obtained by preparing the active ingredients all at once. When administered at the same time, it may also be administered through the same administration route or through the different administration routes in the forms of plural drugs obtained by preparing each active ingredient of the present invention separately. When administered sequentially at time intervals, plural drugs obtained by preparing each active ingredient separately may be administered through the same administration route or through the different administration routes. In this case, administration sequence of each active ingredient can be selected arbitrarily.

The pharmaceutical compositions of the present invention are used for mammals. The dose of the pharmaceutical compositions of the present invention can be selected arbitrarily depending on the patient, his or her age and body weight, symptoms, period of the administration, dosage form, administration route and combination of agents. The dose is usually 1 mg to 3600 mg of gabapentin or pregabalin, or pharmaceutically acceptable salts thereof and 0.01 µg to 5 g of N-type calcium channel antagonists a day for adults.

The diarylalkene derivatives and diarylalkyl derivatives (1), (2), (3) and (4) of the present invention can be produced by processes described below.

For example, diarylalkene derivatives and diarylalkyl derivatives (1-1) and (3-1) of the general formulae (1) and (3) wherein $Y_1$ represents oxygen atom, B represents —$(CH_2)_v$—$CHR^{21}$ and $R^5$ and $R^6$ do not together form oxygen atom or sulfur atom and also diarylalkene derivatives and diarylalkyl derivatives (2-1) of the general formula (2) wherein $Y_1$ represents oxygen atom, and $R^5$ and $R^6$ do not together form oxygen atom or sulfur atom can be produced as follows:

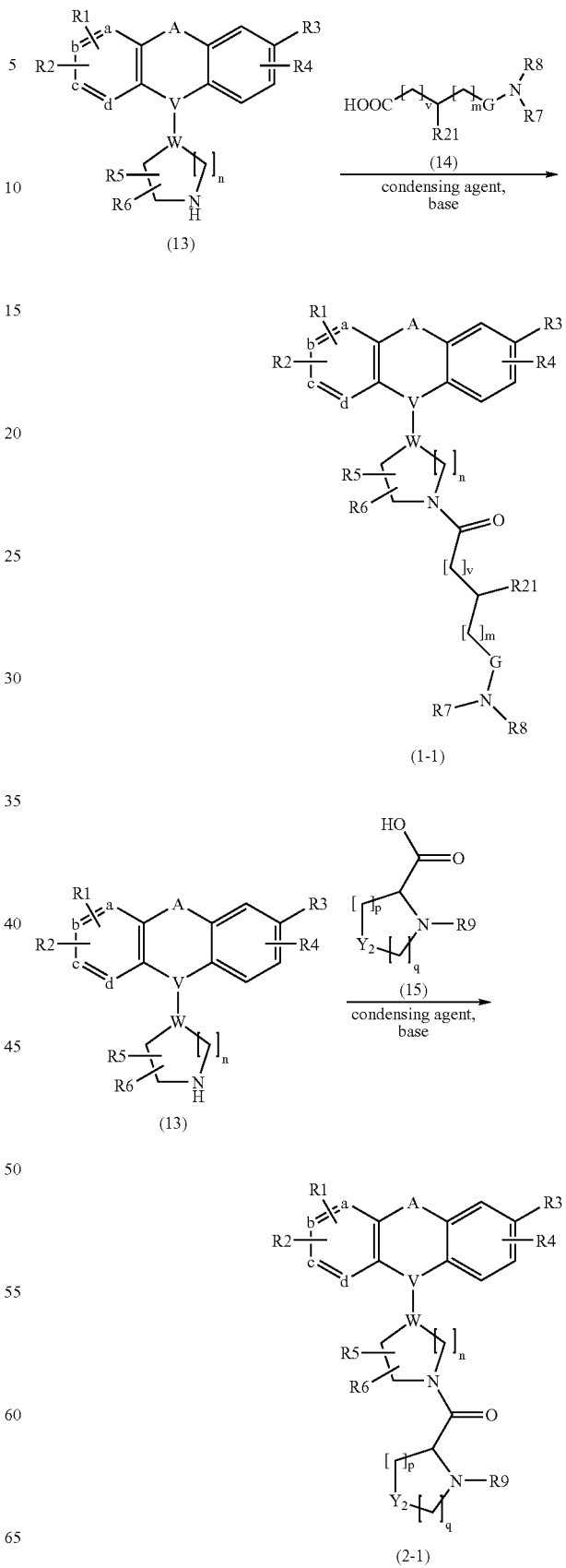

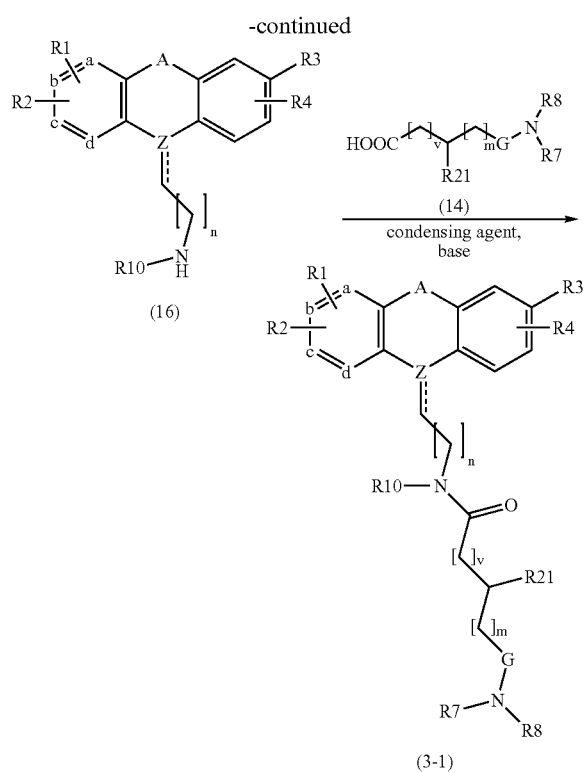

The intended diarylalkene derivatives and diarylalkyl derivatives can be obtained by condensing an amine (13) or (16) with a carboxylic acid (14) or (15) in the presence of a base such as triethylamine and a condensing agent such as 1-ethyl-3-(3'-dimethylaminopropyl)carbodiimide and 1,3-dicyclohexylcarbodiimide. 3-(10,11-Dihydro-5H-dibenzo[a,d][7]-annulen-5-ylidene)pyrrolidine was synthesized according to [Patent: FR1522934]. Compounds (1-1) and (1-3) wherein $R^{21}$ is a hydroxyalkyl group can be obtained by, for example, condensing a compound (14) having an ester corresponding to $R^{21}$ or a compound (14) having protected hydroxyl group and then reducing the ester with a reducing agent such as lithium borohydride or removing the protecting group. Compounds (1-1) and (1-3) having carboxyl group in $R^{21}$ can also be obtained by condensing a compound (14) having a corresponding ester to $R^{21}$ and then hydrolyzing the ester with a base such as sodium hydroxide. Compounds (1-1) and (1-3) having a primary or secondary amino group in $R^{21}$ can be obtained by condensing a compound (14) having an amino group protected with, for example, tert-butoxycarbonyl group and then removing the protecting group with an acid or the like.

Diarylalkene derivatives and diarylalkyl derivatives (1-2), (1-2'), (3-2) and (3-2') of the general formulae (1) and (3) wherein $Y_1$ represents oxygen atom, B represents $NR^{17a}$ or $-NR^{17a}(CH^2)_vCHR^{21}-$ and $R^5$ and $R^6$ do not together form oxygen atom or sulfur atom can be produced as follows:

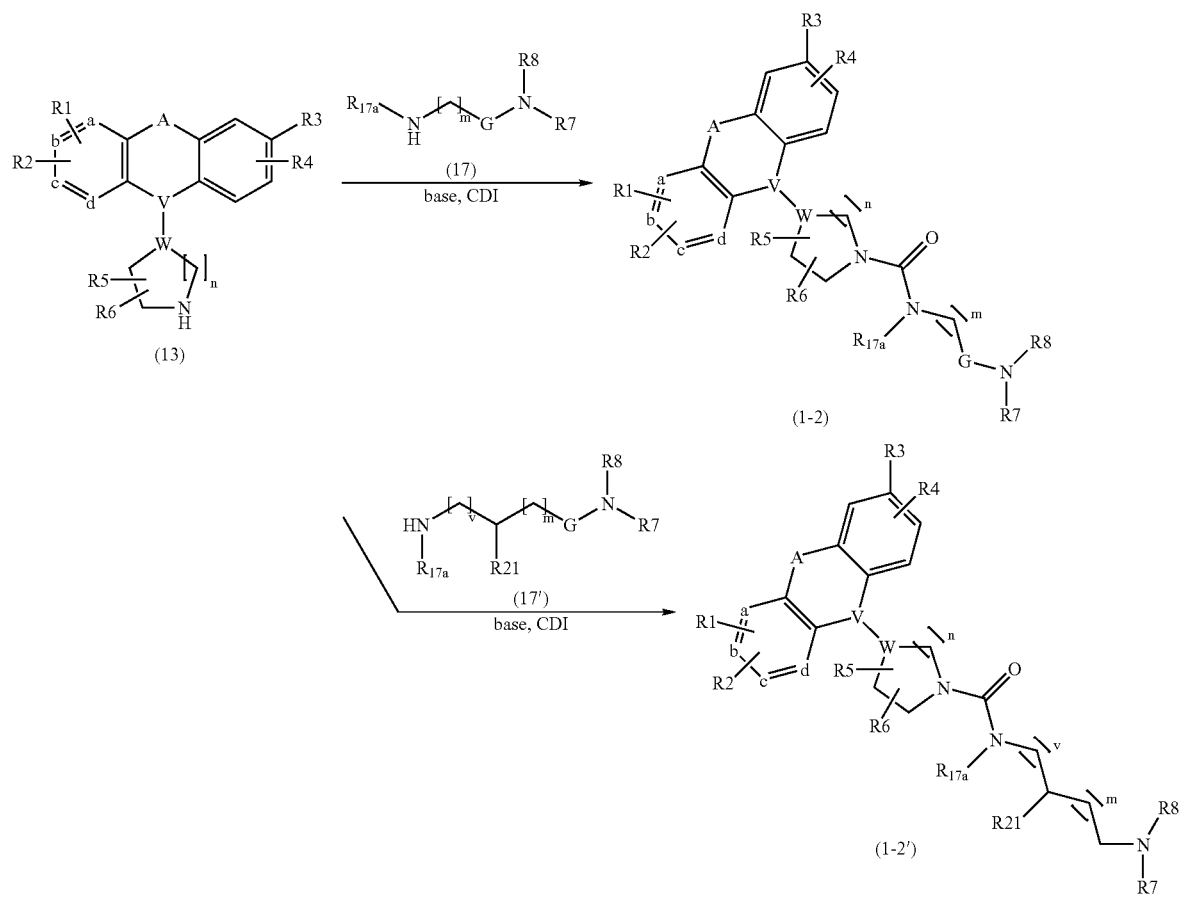

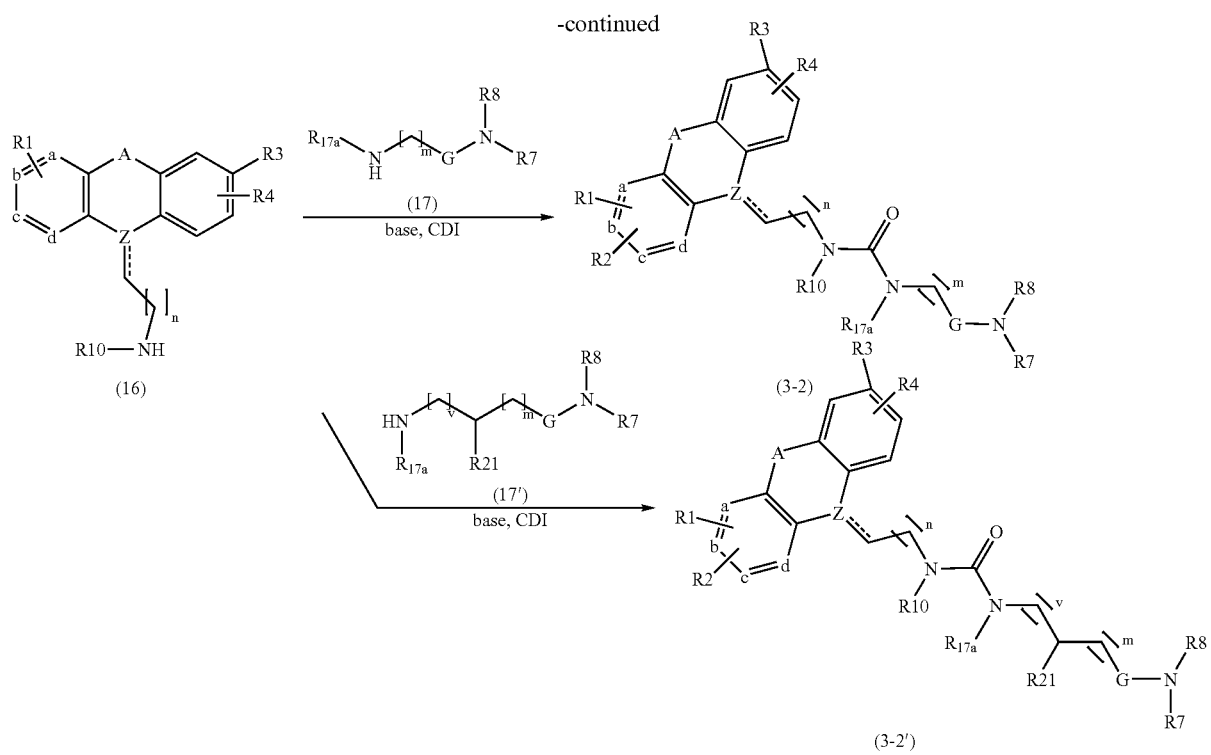

The intended diarylalkene derivatives and diarylalkyl derivatives can be obtained by reacting an amine (13) or (16) and an amine (17) or (17') with 1,1'-carbonylbis-1H-imidazole (CDI) in the presence of a base such as triethylamine. Compounds (1-2') and (3-2') wherein $R^{21}$ is a hydroxyalkyl group can be obtained by condensing a compound (17') having a corresponding ester to $R^{21}$ or a compound (17') having protected hydroxyl group and then reducing the ester with a reducing agent such as lithium borohydride or removing the protecting group.

When compounds (1-3) and (3-3) have t-butoxycarbonyl group (Boc group) as shown below, they can be converted into amines (1-4) and (3-4) by using an acid such as trifluoroacetic acid and hydrochloric acid. Also, they can be acylated with an acylating agent such as an acid chloride, an acid anhydride, a chloroformic ester and carbamoyl chloride in the presence of a base such as triethylamine to obtain diarylalkene derivatives and diarylalkyl derivatives of formulae (1-5) and (3-5):

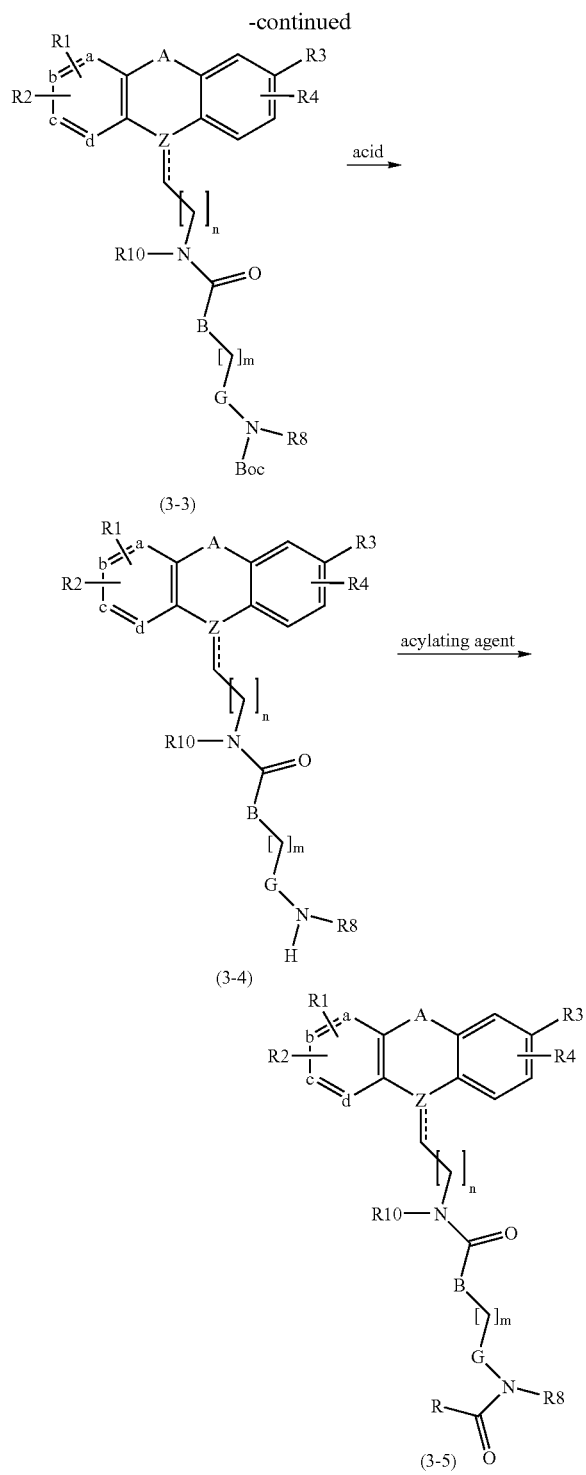
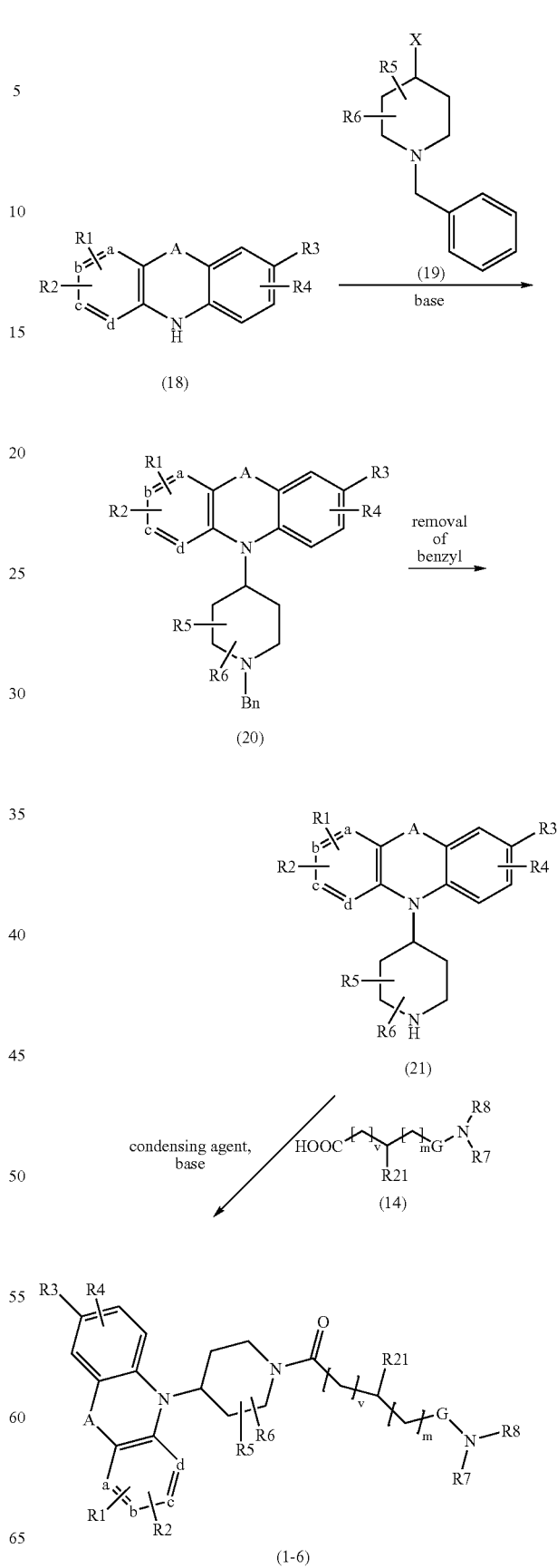

Diarylalkyl derivatives (1-6) of the general formula (1) wherein $Y_1$ represents oxygen atom, B represents —$(CH_2)_v$—$CHR^{21}$—, V=W represents N—C, n represents 2 and $R^5$ and $R^6$ do not together form oxygen atom or sulfur atom can be produced as shown in the following reaction scheme wherein X represents a halogen such as I, Br and Cl, or a sulfonyloxyl group such as methanesulfonyloxyl group, trifluoromethanesulfonyloxyl group and p-toluenesulfonyloxyl group:

Tertiary aniline derivatives such as those represented by formula (20) can be obtained by reacting an aniline derivative (18) with a sulfonic acid ester or a halide (19) in the presence of a base such as sodium hydride and lithium diisopropylamide. Secondary amines (21) can be obtained by removing benzyl from the compounds (20) in the presence of a catalyst such as palladium carbon, palladium hydroxide carbon and Raney nickel. By condensing the secondary amines (21) with a carboxylic acid (14) in the presence of a base such as triethylamine and a condensing agent such as 1-ethyl-3-(3'-dimethylaminopropyl)carbodiimide and 1,3-dicydohexylcarbodiimide, the intended diarylalkene derivatives and diarylalkyl derivatives can be obtained. The compounds (1-6) wherein $R^{21}$ represents a hydroxyalkyl group can be produced by condensing a compound (14) having an ester corresponding to $R^{21}$ or a compound (14) having protected hydroxyl group and then reducing the ester with a reducing agent such as lithium borohydride or removing the protecting group.

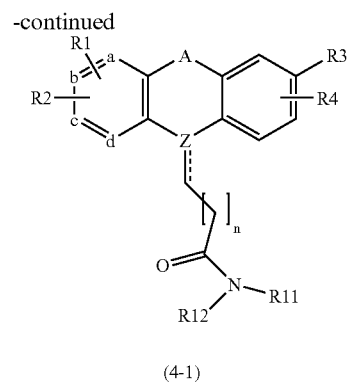

(4-1)

In the compounds (22), those (24) wherein Z is C and n is 0 can be synthesized by, for example, the following reaction scheme:

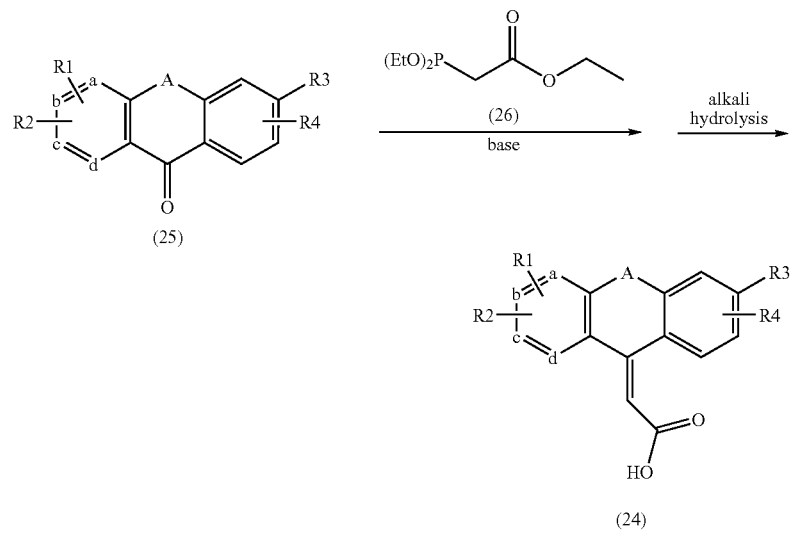

When $Y_1$ in (4) is oxygen atom, the intended diarylalkene derivatives and diarylalkyl derivatives (4-1) can be obtained by, for example, condensing a carboxylic acid (22) with an amine (23) in the presence of a base such as triethylamine and a condensing agent such as 1-ethyl-3-(3'-dimethylaminopropyl)carbodiimide and 1,3-dicyclohexylcarbodiimide.

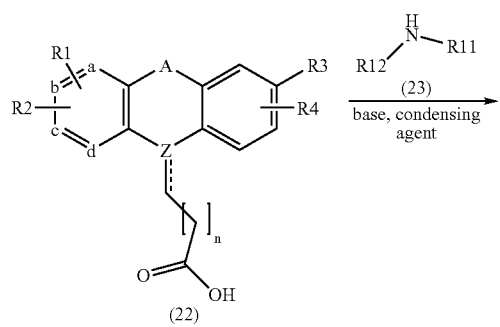

The intended compounds (24) can be obtained by, for example, condensing a ketone (25) with ethyl diethylphosphonoacetate (26) in the presence of a base such as sodium hydride and lithium diisopropylamide.

Further, the compounds of the above (II) to (X) described in the present invention can be produced, for example, in accordance with the methods described in the references shown in Table 1 and 2.

REFERENTIAL EXAMPLES

The following Referential Examples will further illustrate the methods for producing the compounds described in the present invention, which by no means limit the invention.

Referential Example 1

Synthesis of t-butyl 2-[4-(5H-dibenzo[a,d][7]annulen-5-ylidene)-1-piperidinyl]-2-oxoethylcarbamate:

3.00 g (10.9 mmol) of 4-(5H-dibenzo[a,d][7]annulen-5-ylidene)-1-piperidine, 2.29 g (13.2 mmol) of N-t-butoxycarbonylglycine, 3.14 g (16.4 mmol) of 1-ethyl-3-(3'-dimethylaminopropyl)carbodiimide hydrochloride and 122 mg (1.00 mmol) of 4-dimethylaminopyridine were dissolved in 50 ml of dichloromethane. 2.20 g (3.04 mmol) of triethylamine was added to the obtained solution, and they were stirred overnight. Saturated aqueous sodium hydrogencarbonate solution was added to the obtained mixture. After extracting with dichloromethane 3 times, the organic layer was washed with saturated aqueous sodium chloride solution. After drying over anhydrous sodium sulfate, the solvent was evaporated under reduced pressure, and the residue was purified by the silica gel chromatography (hexane:ethyl acetate=4:1 to 2:1) to obtain the title compound.

Yield: 4.29 g (10.2 mmol), 94% MS (ESI, m/z) 431 (M+H)$^{+1}$H-NMR (CDCl$_3$): 1.44 (9H, s), 2.15-2.35 (4H, m), 3.02 (2H, m), 3.42 (1H, m), 3.81-4.01 (3H, m), 5.51 (1H, br s), 6.92 (2H, s), 7.15-7.38 (8H, m).

Referential Example 2

Synthesis of 2-[4-(5H-dibenzo[a,d][7]annulen-5-ylidene)-1-piperidinyl]-2-oxo-ethanamine hydrochloride:

1.40 g (3.25 mmol) of t-butyl 2-[4-(5H-dibenzo[a,d][7] annulen-5-ylidene)-1-piperidinyl]-2-oxoethylcarbamate was dissolved in 20 ml of 1,4-dioxane. 12 ml of 4 N hydrochloric acid/1,4-dioxane solution was added to the obtained solution, and they were stirred overnight. After the neutralization with 4 N aqueous sodium hydroxide solution, the solvent was evaporated under reduced pressure. Saturated aqueous sodium chloride solution was added to the reaction mixture. After the extraction with ethyl acetate 3 times, the extract was dried over anhydrous sodium sulfate and then the solvent was evaporated under reduced pressure. 10 ml of a solution of ethyl acetate:hexane (1:2) and then 2 ml of 4 N hydrochloric acid/1,4-dioxane solution were added to the residue. The resultant precipitates were taken by the filtration, washed with a solution of ethyl acetate:hexane (1:2) and air-dried. After further drying under reduced pressure, the title compound was obtained.

Yield: 1.15 g (3.06 mmol), 94% MS (ESI, m/z) 415 (M+H+DMSO-d$_6$)$^{+1}$H-NMR (CDCl$_3$) (free): 2.12-2.36 (4H, m), 2.36 (2H, s), 2.76-3.12 (2H, m), 3.13-3.50 (3H, m), 3.88-4.00 (1H, m), 6.92 (2H, s), 7.12-7.38 (8H, m).

Referential Example 3

Synthesis of Ethyl 2-[4-(5H-dibenzo[a,d][7]annulen-5-ylidene)-1-piperidinyl]-2-oxoethylcarbamate:

375 mg (1.00 mmol) of 2-[4-(5H-dibenzo[a,d][7]annulen-5-ylidene)-1-piperidinyl-2-oxoethanamine hydrochloride was dissolved in 3 ml of dichloromethane. 303 mg (3.00 mmol) of triethylamine was added to the obtained solution. Then a solution of 130 mg (1.20 mmol) of ethyl chloroformate in 3 ml of dichloromethane was slowly added to the reaction mixture. After stirring overnight, saturated aqueous sodium hydrogencarbonate solution was added thereto. After extracting with ethyl acetate twice followed by drying under anhydrous sodium sulfate, the solvent was evaporated under reduced pressure. The residue was roughly purified by the silica gel chromatography (dichloromethane: methanol=98: 2) and then purified by the silica gel chromatography (hexane: ethyl acetate=1:2) to obtain the title compound.

Yield: 213 mg (0.528 mmol), 53% MS (ESI, m/z) 403(M+H)$^{+1}$H-NMR (CDCl$_3$): 1.24 (3H, t), 2.12-2.36 (4H, m), 2.97-3.10 (2H, m), 3.38-3.50 (2H, m), 3.86-4.02 (3H, m), 4.13 (2H, q), 5.65 (1H, br s), 6.92 (2H, s), 7.14-7.20 (2H, m), 7.23-7.38 (6H, m).

Referential Example 4

Synthesis of t-butyl (1S)-1-{[4-(5H-dibenzo [a, d] annulen-5-ylidene)-1-piperidinyl]carbonyl}-3-methylbutylcarbamate:

100 mg (0.366 mmol) of 4-(5H-dibenzo[a,d]annulen-5-ylidene)-1-piperidine, 109 mg (0.439 mmol) of N-t-butoxycarbonyl-(L)-leucine, 105 mg (0.549 mmol) of 1-ethyl-3-(3'-dimethylaminopropyl)carbodiimide hydrochloride and 5 mg (0.04 mmol) of 4-dimethylaminopyridine were dissolved in 2 ml of dichloromethane. 74 mg (0.73 mmol) of triethylamine was added to the obtained solution, and they were stirred overnight. Saturated aqueous sodium hydrogencarbonate solution was added to the obtained mixture. After extracting with ethyl acetate 3 times, the organic layer was washed with saturated aqueous sodium chloride solution. After drying over anhydrous sodium sulfate, the solvent was evaporated under reduced pressure, and the residue was purified by the silica gel chromatography (hexane:ethyl acetate=84:16 to 75:25) to obtain the title compound.

Yield: 29.5 mg (0.065 mmol), 17% MS (ESI, m/z) 487(M+H)$^{+1}$H-NMR (CDCl$_3$): 0.84-0.99 (6H, m), 1.23-1.31 (2H, m), 1.41 (9H, d), 1.70 (1H, m), 2.10-2.40 (4H, m), 2.90-3.20 (2H, m), 3.61 (1H, m), 3.94 (1H, m), 4.62 (1H, m), 5.28 (1H, d), 6.92 (2H, d), 7.14-7.38 (8H, m).

Referential Example 5

Synthesis of (1R)-N-{2-[4-(5H-dibenzo[a,d][7] annulen-5-ylidene)-1-piperidinyl]-2-oxoethyl}-2,2-dimethylcyclopropane carboxyamide:

200 mg (0.542 mmol) of 2-[4-(5H-dibenzo[a,d][7]annulen-5-ylidene)-1-piperidinyl]-2-oxoethanamine hydrochloride was dissolved in 1.5 ml of dichloromethane. 137 mg (1.36 mmol) of triethylamine was added to the obtained solution. Then a solution of 86.1 mg (0.650 mmol) of (S)-2,2-dimethylcyclopropanecarboxylic acid chloride in 0.5 ml of dichloromethane was slowly added to the obtained mixture. After stirring for 1 hour, the obtained mixture was roughly purified by the silica gel chromatography (dichloromethane: methanol=98: 2) and then purified by the silica gel chromatography (Chromatorex™ NH, Fuji Silysia Chemical LTD., hexane ethyl acetate=92:8 to 1:4) to obtain the title compound.

Yield: 154 mg (0.362 mmol), 67% MS (ESI, m/z) 427 (M+H)$^{+1}$H-NMR (CDCl$_3$): 0.73 (1H, m), 1.04-1.19 (7H, m), 1.36 (1H, m), 2.12-2.36 (4H, m), 2.96-3.12 (2H, m), 3.40-3.52 (1H, m), 3.80-4.16 (3H, m), 6.65 (1H, bs), 6.92 (2H, s), 7.13-7.20 (2H, m), 7.21-7.40 (6H, m).

Referential Example 6

Synthesis of (1R)-N-{2-[4-(10,11-dihydro-5H-dibenzo[a,d][7]annulen-5-ylidene)-1-piperidinyl]-2-oxoethyl}-2,2-dimethylcyclopropane carboxyamide:

72.8 mg of palladium carbon (10% w/v) was added to 72.8 mg (0.171 mmol) of (1R)-N-{2-[4-(5H-dibenzo[a,d] [7]annulen-5-ylidene)-1-piperidinyl]-2-oxoethyl}-2,2-dimethylcyclopropanecarboxyamide in 10 ml of ethanol, and they were stirred at 4.0 MPa in hydrogen gas atmosphere overnight. After the filtration, the solvent was evaporated under reduced pressure to obtain the title compound.

Yield: 67.1 mg (0.157 mmol), 92% MS (ESI, m/z) 429(M+H)$^{+1}$H-NMR (CDCl$_3$): 0.75 (1H, dd), 1.05-1.41 (7H, m), 1.37 (1H, dd), 2.30-2.51 (4H, m), 2.35-2.82 (2H, m), 3.09-3.24

(2H, m), 3.31-3.46 (2H, m), 3.48-3.60 (1H, m), 4.00-4.19 (3H, m), 6.68 (1H, br s), 7.00-7.04 (2H, m), 7.04-7.18 (6H, m).

Referential Example 8

Synthesis of N-{2-[4-(5H-dibenzo [a,d] [7] annulen-5-ylidene)-1-piperidinyl]-2-oxoethyl}-2,2-dimethylpropanamide:

100 mg (0.271 mmol) of 2-[4-(5H-dibenzo[a,d][7]annulen-5-ylidene)-1-piperidinyl]-2-oxoethanamine hydrochloride was dissolved in 1 ml of dichloromethane. 82.3 mg (0.813 mmol) of triethylamine was added to the obtained solution. A solution of 39.2 mg (0.325 mmol) of pivaloyl chloride in 0.5 ml of dichloromethane was slowly added to the obtained mixture. After stirring for 30 minutes, the obtained product was purified by the silica gel chromatography (hexane:ethyl acetate=9:1 to 3:1) to obtain the title compound.

Yield: 62.9 mg (0.152 mmol) (56%) MS (ESI, m/z) 415 $(M+H)^{+1}$H-NMR (CDCl$_3$): 1.21 (9H, s), 2.14-2.35 (4H, m), 2.98-3.12 (2H, m), 3.40-3.53 (1H, m), 3.88-4.09 (3H, m), 6.83 (1H, br s), 6.92 (2H, s), 7.12-7.22 (2H, m), 7.22-7.40 (6H, m).

Referential Example 9

Synthesis of N-(t-butyl)-4-[4-(5H-dibenzo[a,d][7]annulen-5-ylidene)-1-piperidinyl]-4-oxobutanamide:

100 mg (0.268 mmol) of 4-[4-(5H-dibenzo[a,d][7]annulen-5-ylidene)-1-piperidinyl]-4-oxobutanoic acid, 23.5 mg (0.321 mmol) of t-butylamine, 3 mg (0.03 mmol) of 4-dimethylaminopyridine and 77.1 mg (0.402 mmol) of 1-ethyl-3-(3'-dimethylaminopropyl)carbodiimide hydrochloride were dissolved in 1 ml of dichloromethane. 35.2 mg (0.348 mmol) of triethylamine was added to the obtained solution, and they were stirred overnight. The obtained product was purified by the silica gel chromatography (hexane:ethyl acetate=2:1 to 4:6) to obtain the title compound.

Yield: 33.3 mg (0.078 mmol), 29% MS (ESI, m/z) 429 $(M+H)^{+1}$H-NMR (CDCl$_3$): 1.32 (9H, s), 2.08-2.36 (4H, m), 2.41 (2H, t), 2.50-2.71 (2H, m), 2.24-2.96 (2H, m), 3.58 (1H, m), 3.93 (1H, m), 5.77 (1H, br s), 6.92 (2H, s), 7.14-7.38 (8H, m).

Referential Example 10

Synthesis of N-{2-[4-(5H-dibenzo[a,d][7]annulen-5-ylidene)-1-piperidinyl]-2-oxoethyl}-2-methyl-1-propanamine hydrochloride:

128.5 mg (0.264 mmol) of t-butyl 2-[4-(5H-dibenzo[a,d][7]annulen-5-ylidene)-1-piperidinyl]-2-oxoethyl(isobutyl)carbamate was dissolved in 1 ml of 1,4-dioxane. 0.5 ml of 4 N hydrochloric acid/1,4-dioxane solution was added to the obtained solution, and they were stirred overnight. Saturated aqueous sodium hydrogencarbonate solution was added to the reaction mixture. After the extraction with ethyl acetate 3 times, the extract was dried over anhydrous sodium sulfate and then the solvent was evaporated under reduced pressure. The residue was purified by the silica gel chromatography (hexane:ethyl acetate=89:11 to 65:35). The solvent was evaporated under reduced pressure, and the residue was dissolved in 2 ml of diethyl ether. 4 N hydrochloric acid/ethyl acetate solution was added to the obtained solution. The precipitates thus formed were taken by the filtration and then washed with diethyl ether. After drying under reduced pressure, the title compound was obtained.

Yield: 102.6 mg (0.242 mmol) 92% MS (ESI, m/z) 387 $(M+H)^{+1}$H-NMR (CDCl$_3$): 1.08 (6H, d), 2.10-2.40 (5h, m), 2.70-3.10 (4H, m), 3.41 (1H, br s), 3.69-4.10 (3H, m), 6.92 (2H, s), 7.10-7.21 (2H, m), 7.23-7.39 (6H, m), 9.03 (1H, br s), 9.68 (1H, br s).

Referential Example 11

Synthesis of N-{3-[4-(5H-dibenzo[a, d] [7] annulen-5-ylidene)-1-piperidinyl]-3-oxopropyl}-2,2-dimethylpropanamide:

Step 1

Synthesis of N-(2,2-dimethylpropanoyl)-β-alanine:

558 mg (4.03 mmol) of methyl 3-aminopropionate hydrochloride was dissolved in 20 ml of 1 N aqueous sodium hydroxide solution. 362 mg (3.00 mmol) of pivaloyl chloride was immediately added to the obtained solution, and they were stirred for 4 hours. 15 ml of 2 N aqueous hydrochloric acid solution was added to the reaction mixture. After extracting with ethyl acetate 3 times followed by drying under anhydrous sodium sulfate, the solvent was evaporated under reduced pressure to obtain the title compound.

Yield: 173 mg (0.929 mmol), 23% $^1$H-NMR (CDCl$_3$): 1.18 (9H, s), 2.60 (2H, t), 3.51 (2H, q), 6.34 (1H, br s).

Step 2

Synthesis of N-{3-[4-(5H-dibenzo[a,d][7]annulen-5-ylidene)-1-piperidinyl]-3-oxopropyl}-2,2-dimethylpropanamide:

275 mg (1.01 mmol) of 4-(5H-dibenzo[a,d][7]annulen-5-ylidene)-1-piperidine, 90.0 mg (0.480 mmol) of N-(2,2-dimethylpropanoyl)-β-alanine, 193 mg (1.01 mmol) of 1-ethyl-3-(3'-dimethylaminopropyl)carbodiimide hydrochloride and 6 mg (0.05 mmol) of 4-dimethylaminopyridine were dissolved in 3 ml of dichloromethane. 152 mg (1.50 mmol) of triethylamine was added to the obtained solution. After stirring for 3 hours, the obtained mixture was roughly purified by the silica gel chromatography (Chromatorex™ NH, Fuji Silysia Chemical LTD., hexane:ethyl acetate=89:11 to 7:3) and then purified by the silica gel chromatography (hexane ethyl acetate=2:3 to 1:4) to obtain the title compound.

Yield: 147 mg (0.343 mmol), 72% MS (ESI, m/z) 429 $(M+H)^{+1}$H-NMR (CDCl$_3$): 1.16 (9H, s), 2.11-2.36 (4H, m), 2.48 (2H, q), 2.94-3.12 (2H, m), 3.52 (3H, q), 3.84-4.00 (1H, m), 6.62 (1H, t), 6.92 (2H, s), 7.13-7.20 (2H, m), 7.22-7.38 (6H, m).

Referential Example 12

Synthesis of N-{2-[4-(5H-dibenzo[a,d][7]annulen-5-ylidene)-1-piperidinyl]-2-oxoethyl}-3,3-dimethylbutanamide:

80.0 mg (0.217 mmol) of 2-[4-(5H-dibenzo[a,d][7]annulen-5-ylidene)-1-piperidinyl]-2-oxoethanamine hydrochloride was dissolved in 1 ml of dichloromethane. 75.9 mg (0.750 mmol) of triethylamine was added to the obtained solution. Then a solution of 35.1 mg (0.260 mmol) of 3,3-dimethylbutanoyl chloride in 0.5 ml of dichloromethane was slowly added to the obtained mixture. After stirring for 30 minutes, the product was purified by the silica gel chromatography (hexane:ethyl acetate=93:7 to 3:1) to obtain the title compound.

Yield: 80.1 mg (0.187 mmol), 86% MS (ESI, m/z) 429 $(M+H)^{+1}$H-NMR (CDCl$_3$): 1.03 (9H, s), 2.12 (2H, s), 2.15-

2.39 (4H, m), 2.96-3.11 (2H, m), 3.40-3.54 (1H, m), 3.88-4.13 (3H, m), 6.49 (1H, br s), 6.92 (2H, s), 7.14-7.21 (2H, m), 7.21-7.41 (6H, m).

Referential Example 13

Synthesis of isopropyl 2-[4-(5H1-dibenzo[a,d][7]annulen-5-ylidene)-1-piperidinyl]-2-oxoethylcarbamate:

80.0 mg (0.217 mmol) of 2-[4-(5H-dibenzo[a,d][7]annulen-5-ylidene)-1-piperidinyl]-2-oxoethanamine hydrochloride was dissolved in 1 ml of dichloromethane. 75.9 mg (0.750 mmol) of triethylamine was added to the obtained solution. Then a solution of 31.9 mg (0.260 mmol) of isopropyl chloroformate in 0.5 ml of dichloromethane was slowly added to the obtained mixture. After stirring for 30 minutes, the obtained product was purified by the silica gel chromatography (hexane:ethyl acetate=93:7 to 3:1) to obtain the title compound.

Yield: 38.6 mg (0.093 mmol), 43% MS (ESI, m/z) 417 (M+H)$^{+1}$H-NMR (CDCl$_3$): 1.23 (6H, d), 2.12-2.48 (4H, m), 2.92-3.11 (2H, m), 3.36-3.53 (1H, m), 3.83-4.09 (3H, m), 4.90 (1H, m), 5.59 (1H, br s), 6.92 (2H, s), 7.14-7.20 (2H, m), 7.23-7.38 (6H, m).

Referential Example 14

Synthesis of N-{3-[4-(5H-dibenzo[a,d][7]annulen-5-ylidene)-1-piperidinyl]-3-oxopropyl}-2,2-dimethyl-1-propanamine Hydrochloride:

5 ml of 4 N hydrochloric acid/1,4-dioxane solution was added to 184.1 mg (0.357 mmol) of t-butyl 3-[4-(5H-dibenzo[a,d][7]annulen-5-ylidene)-1-piperidinyl]-3-oxopropyl(neopentyl)carbamate, and they were stirred for 1 hour. The solvent was evaporated under reduced pressure. 5 ml of diethyl ether was added to the residue, and then 1 ml of 4 N hydrochloric acid/ethyl acetate solution was added thereto. The precipitates thus formed were taken by the filtration, washed with diethyl ether and dried under reduced pressure to obtain the title compound.

Yield: 149 mg (0.357 mmol), 100% MS (ESI, m/z) 415 (M+H)$^{+1}$H-NMR (CDCl$_3$): 1.24 (9H, s), 2.14-2.43 (4H, m), 2.52 (2H, s), 2.62-3.37 (6H, m), 3.52 (1H, m), 3.95 (1H, m), 6.92 (2H, s), 7.12-7.24 (2H, m), 7.26-7.40 (6H, m), 9.05 (1H, br s), 9.55 (1H, br s).

Referential Example 15

Synthesis of N-((1S)-1-{[4-(5H-dibenzo[a,d]annulen-5-ylidene)-1-piperidinyl]-carbonyl}-3-methylbutyl)-1-azepanecarboxyarmide:

100 mg (0.366 mmol) of 4-(5H-dibenzo[a,d][7]annulen-5-ylidene)-1-piperidine, 124 mg (0.439 mmol) of N-t-azepanecarboxyamido-CL)-leucine, 105 g (0.549 mmol) of 1-ethyl-3-(3'-dimethylaminopropyl)carbodiimide hydrochloride and 5 mg (0.04 mmol) of 4-dimethylaminopyridine were dissolved in 2 ml of dichloromethane. 74 mg (0.73 mmol) of triethylamine was added to the obtained solution, and they were stirred overnight. Saturated aqueous sodium hydrogencarbonate solution was added to the obtained mixture. After extracting with ethyl acetate 3 times, the organic layer was washed with saturated aqueous sodium chloride solution. After drying over anhydrous sodium sulfate, the solvent was evaporated under reduced pressure, and the residue was roughly purified by the silica gel chromatography (hexane:ethyl acetate=4:1 to 65:35) and then purified by the silica gel chromatography (hexane:ethyl acetate=3:1) to obtain the title compound.

Yield: 98.9 mg (0.194 mmol), 53% MS (ESI, m/z) 512 (M+H)$^{+1}$H-NMR (CDCl$_3$): 0.54-1.02 (6H, m), 1.23-1.82 (1H, m), 2.10-2.25 (4H, m), 3.00 (1H, m), 3.16 (1H, m), 3.39 (4H, m), 3.65 (1H, m), 3.3 (1H, m), 4.90 (1H, m), 5.21 (1H, m), 6.92 (2H, s), 7.15-7.39 (8H, m).

Referential Example 16

Synthesis of t-butyl 2-[4-(10,11-dihydro-5H-dibenzo[a,d][7]annulen-5-ylidene)-1-piperidinyl]-2-oxoethyl Carbamate:

400 mg of palladium carbon (10% w/v) was added to 400 mg (0.930 mmol) of t-butyl 2-[4-(5H-dibenzo[a,d][7]annulen-5-ylidene)-1-piperidinyl]-2-oxoethylcarbamate in 5 ml of ethanol, and they were stirred at 3.9 MPa in hydrogen gas atmosphere overnight. After the filtration, the solvent was evaporated under reduced pressure to obtain the title compound.

Yield: 397 g (0.918 mmol), 99% MS (ESI, m/z) 433 (M+H)$^{+1}$H-NMR (CDCl$_3$): 1.46 (9H, s), 2.29-2.50 (4H, m), 2.77-2.92 (2H, m), 3.08-3.21 (2H, m), 3.31-3.45 (2H, m), 3.45-3.56 (1H, m), 3.87-4.10 (3H, m), 5.56 (1H, br s), 7.00-7.07 (2H, m), 7.09-7.20 (6H, m).

Referential Example 17

Synthesis of t-butyl 2-oxo-2-[4-(9H-thioxanthen-9-ylidene)-1-piperidinyl]ethylcarbamate:

500 mg (1.79 mmol) of 4-(9H-thioxanthen-9-ylidene)-1-piperidine and 515 mg (2.69 mmol) of 1-ethyl-3-(3'-dimethylaminopropyl)carbodiimide hydrochloride were suspended in 5 ml of dichloromethane. 415 mg (2.15 mmol) of N-t-butoxycarbonylglycine, 362 mg (3.58 mmol) of triethylamine and 22 mg (0.18 mmol) of 4-dimethylaminopyridine were added to the obtained suspension, and they were stirred overnight. Saturated aqueous sodium hydrogencarbonate solution was added to the obtained mixture. After extracting with ethyl acetate twice and drying over anhydrous sodium sulfate, the solvent was evaporated under reduced pressure, and the residue was roughly purified by the silica gel chromatography (dichloromethane: methanol=98:2) and then purified by the thin-layer silica gel chromatography (dichloromethane: methanol=15:1) to obtain the title compound.

Yield: 43.1 mg (0.100 mmol), 5.6% MS (ESI, m/z) 437 (M+H)$^{+1}$H-NMR (CDCl$_3$): 1.45 (9H, s), 2.50-2.64 (2H, m), 2.68-2.81 (2H, m), 2.92-3.14 (2H, m), 3.52-3.62 (1H, m), 3.85-4.10 (2H, m), 4.13-4.24 (1H, m), 5.53 (1H, br s), 7.16-7.32 (6H, m), 7.48-7.54 (2H, d).

Referential Example 18

Synthesis of Ethyl 2-[4-(10,11-dihydro-5H-dibenzo[a,d][7]annulen-5-ylidene)-1-piperidinyl]-2-oxoethylcarbamate:

100 mg of palladium carbon (10% w/v) was added to 105 mg (0.261 mmol) of ethyl 2-[4-(5H-dibenzo[a,d][7]annulen-5-ylidene)-1-piperidinyl]-2-oxoethylcarbamate in 3 ml of ethanol, and they were stirred at 3.6 MPa in hydrogen gas atmosphere overnight. After the filtration, the solvent was evaporated under reduced pressure to obtain the title compound.

Yield: 101.8 mg (0.252 mmol), 97% MS (ESI, m/z) 405 (M+H)$^{+1}$H-NMR (CDCl$_3$): 1.26 (3H, t), 2.30-2.52 (4H, m), 2.75-2.92 (2H, m), 3.08-3.23 (2H, m), 3.30-3.45 (2H, m), 3.45-3.58 (1H, m), 3.90-4.20 (5 h, m), 5.68(1H, br s), 6.98-7.07 (2H, m), 7.07-7.21 (6H, m).

Referential Example 19

Synthesis of Ethyl 2-oxo-2-[4-(9H-thioxanthen-9-ylidene)-1-piperidinyl]ethylcarbamate:

Step 1

Synthesis of 2-[4-(9H-thioxanthen-9-ylidene)-1-piperidinyl]-2-oxoethanamine hydrochloride:

135 mg (0.297 mmol) of t-butyl 2-oxo-2-[4-(9H-thioxanthen-9-ylidene)-1-piperidinyl]ethylcarbamate was dissolved in 2 ml of dioxane. After adding 2 ml of 4 N hydrochloric acid/1,4-dioxane solution, they were stirred overnight. The obtained mixture was neutralized with saturated aqueous sodium hydrogencarbonate solution. After extracting with ethyl acetate twice and drying over anhydrous sodium sulfate, the solvent was evaporated under reduced pressure. 2 ml of dichloromethane and then 2 ml of 4 N hydrochloric acid/1,4-dioxane solution were added to the residue. The resultant precipitates were taken by the filtration, washed with dichloromethane and air-dried. After further drying under reduced pressure, the title compound was obtained.

Yield: 72.4 mg (0.195 mmol), 66% $^1$H-NMR (DMSO-$d_6$): 2.40-2.54 (2H, m), 2.57-2.80 (2H, m), 3.20 (2H, m), 3.34-3.75 (1H, m), 3.80-3.96 (3H, m), 7.22-7.48 (6H, m), 7.57 (2H, d), 8.16 (3H, br s).

Step 2

Synthesis of ethyl 2-oxo-2-[4-(9H-thioxanthen-9-ylidene)-1-piperidinyl]ethylcarbamate:

50 mg (0.134 mmol) of 2-[4-(9H-thioxanthen-9-ylidene)-1-piperidinyl]-2-oxoethanamine hydrochloride was dissolved in dichloromethane. 41 mg (0.405 mmol) of triethylamine was added to the obtained solution. A solution of 17.5 mg (0.161 mmol) of ethyl chloroformate in 0.5 ml of dichloromethane was added to the resultant mixture. After stirring for 15 minutes, the product was purified by the thin-layer silica gel chromatography (hexane: ethyl acetate=85:100) to obtain the title compound.

Yield: 36.7 mg (0.0897 mmol), 67% MS (ESI, m/z) 409 $(M+H)^{+1}$H-NMR (CDCl$_3$): 1.26 (3H, t), 2.48-2.64 (2H, m), 2.68-2.82 (2H, m), 2.92-3.16 (2H, m), 3.51-3.64 (1H, m), 3.90-4.24 (5h, m), 5.67 (1H, br s), 7.22-7.33 (6H, m), 7.51 (2H, d).

Referential Example 20

Synthesis of t-butyl 3-[4-(5H-dibenzo[a,d][7] annulen-5-ylidene)-1-piperidinyl]-3-oxopropylcarbamate:

50 mg (0.183 mmol) of 4-(5H-dibenzo[a,d][7]annulen-5-ylidene)-1-piperidine was dissolved in 1 ml of dichloromethane. 41.5 mg (0.219 mmol) of N-t-butoxycarbonyl-3-aminopropionic acid, 2 mg (0.018 mmol) of 4-dimethylaminopyridine, 37 mg (0.366 mmol) of triethylamine and 52.6 mg (0.274 mmol) of 1-ethyl-3-(3'-dimethylaminopropyl)carbodiimide hydrochloride were added to the obtained solution, and they were stirred overnight. After the purification by the thin-layer silica gel chromatography (hexane:ethyl acetate=2:3), the title compound was obtained.

Yield: 72.3 mg (0.163 mmol), 89% MS (ESI, m/z) 445 $(M+H)^{+1}$H-NMR (CDCl$_3$): 1,49 (3H, s), 2.12-2.36 (4H, m), 3.86-3.36 (4H, m), 3.52-3.28 (1H, m), 3.85-4.08 (1H, m), 4.40-4.58 (1H, d), 4.69-4.83 (1H, d), 5.16 (1H, br s), 6.92 (2H, s), 7.13-7.22 (2H, m), 7.22-7.39 (6H, m).

Referential Example 21

Synthesis of t-butyl (4S)-4-{[4-(5H-dibenzo[a,d][7]annulen-5-ylidene)-1-piperidinyl]carbonyl}-1,3-thiazolidine-3-carboxylate:

The reaction and the purification were conducted in the same manner as that of Referential Example 20 except that N-t-butoxycarbonyl-3-aminopropionic acid was replaced with 3-(t-butoxycarbonyl)-1,3-thiazolidine-4-carboxyilc acid.

Yield: 70.8 mg (0.145 mmol), 79% MS (ESI, m/z) 489 $(M+H)^{+1}$H-NMR (CDCl$_3$): 1.29-1.52 (9H, m), 2.10-2.50 (4H, m), 2.70-3.45 (4H, m), 3.51-3.76 (1H, m), 3.82-4.07 (1H, m), 4.47 (1H, d), 4.75 (1H, d), 4.82-5.23 (1H, m), 6.92 (2H, s), 7.17 (2H, d), 7.20-7.40 (6H, m).

Referential Example 22

Synthesis of t-butyl (2R)-2-{[4-(5H-dibenzo[a,d][7]annulen-5-ylidene)-1-piperidinyl]carbonyl}-1-pyrrolidinecarboxylate:

100 mg (0.366 mmol) of 4-(5H-dibenzo[a,d][7]annulen-5-ylidene)-1-piperidine, 94.0 mg (0.439 mmol) of N-t-butoxycarbonyl-(L)-proline, 4 mg (0.036 mmol) of 4-dimethylaminopyridine and 105.2 mg (0.548 mmol) of 1-ethyl-3-(3'-dimethylaminopropyl)carbodiimide hydrochloride were dissolved in 1 ml of dichloromethane. 74 mg (0.731 mmol) of triethylamine was added to the obtained solution, and they were stirred for 3 hours. After the purification by the silica gel chromatography (hexane:ethyl acetate=1:1), the title compound was obtained.

Yield: 155.8 mg (0.331 mmol), 91% MS (ESI, m/z) 471 $(M+H)^{+1}$H-NMR (CDCl$_3$): 1.26-1.52 (9H, m), 1.60-2.53 (8H, m), 2.80-3.26 (2H, m), 3.28-3.71 (3H, m), 3.77-4.10 (1H, m), 4.46-4.72 (1H, m), 6.92 (2H, s), 7.11-7.40 (8H, m).

Referential Example 23

Synthesis of t-butyl 2-[3-(10,11-dihydro-5H-dibenzo[a, d][7]annulen-5-ylidene)-1-pyrrolidinyl]-2-oxoethylcarbamate:

94.0 mg (0.36 mmol) of 3-(10,11-dihydro-5H-dibenzo[a, d][7]annulen-5-ylidene)-1-pyrrolidine, 83.7 ml (0.44 mmol) of N-t-butoxycarbonylglycine, 103.8 mg (0.54 mmol) of 1-ethyl-3-(3'-dimethylaminopropyl)carbodiimide hydrochloride and 4.4 mg (0.04 mmol) of 4-dimethylaminopyridine were dissolved in 1 ml of dichloromethane. 72.8 mg (0.72 mmol) of triethylamine was added to the obtained solution. They were stirred overnight and then purified by the silica gel chromatography (hexane:ethyl acetate=88:12 to 5:1) to obtain the title compound.

Yield: 97.9 g (0.217 mmol), 72% MS (ESI, m/z) 419 $(M+H)+^1$H-NMR (CDCl$_3$): 1.43 (9H, s), 2.48-2.67 (1H, m), 2.70-3.00 (3H, m), 3.20-3.39 (3H, m), 3.58-4.00 (4H, m), 4.30 (1H, t), 5.45 (1H, br s), 7.00-7.24 (8H, m).

Referential Example 24

Synthesis of t-butyl 2-(4-dibenzo[b,e]thiepin-11(6H)-ylidene-1-piperidinyl)-2-oxoethylcarboxylate:

88.0 mg (0.30 mmol) of 4-dibenzo[b,e]thiepin-11(6H)-ylidene-1 -piperidine, 69.6 mg (0.36 mmol) of N-t-butoxycarbonylglycine, 86.3 g (0.45 mmol) of 1-ethyl-3-(3'-dimethylaminopropyl)carbodiimide hydrochloride and 3.7 mg (0.03 mmol) of 4-dimethylaminopyridine were dissolved in 1 ml of dichloromethane. 60.7 mg (0.60 mmol) of triethylamine was added to the obtained solution. They were stirred overnight and then purified by the silica gel chromatography (hexane:ethyl acetate=88:12 to 5:1) to obtain the title compound.

Yield: 115.8 g (0.257 mmol), 86% MS (ESI, m/z) 451 (M+H)$^{+1}$H-NMR (CDCl$_3$): 1.45 (9H, s), 2.09-2.20 (2H, m), 2.38-2.61 (2H, m), 3.10-3.52 (4H, m), 3.34-4.08 (3H, m), 4.86 (1H, d), 5.52 (1H, br s), 6.96-7.16 (5 h, m), 7.20-7.35 (3H, m).

Referential Example 25

Synthesis of 2-[4-(5H-dibenzo[a,d][7]annulen-5-ylidene)-1-piperidinyl]-2-oxoethylformamide:

150 mg (0.406 mmol) of 2-[4-(5H-dibenzo[a,d][7]annulen-5-ylidene)-1-piperidinyl]-2-oxoethanamine hydrochloride, 80.5 mg (0.406 mmol) of 2,2-dimethyl-1-iodopropane and 84.3 mg (0.610 mmol) of potassium carbonate were dissolved in 1 ml of N,N-dimethylformamide, and the obtained solution was stirred at 120° C. overnight. The product was purified by the silica gel chromatography (hexane:ethyl acetate=9:1 to 2:3) to obtain the title compound.

Yield: 18.8 mg (0.052 mmol), 13% MS (ESI, m/z) 359 (M+H)$^{+1}$H-NMR (CDCl$_3$): 2.14-2.38 (4H, m), 2.96-3.12 (2H, m), 3.40-3.52 (1H, m), 3.88-4.18 (3H, m), 6.76 (1H, br s), 6.93 (2H, s), 7.10-7.42 (8H, m), 8.25 (1H, s).

Referential Example 26

Synthesis of t-butyl 2-[4-(5H-dibenzo[a,d] [7] annulen-5-ylidene)-1-piperidinyl]-2-oxoethyl(isobutyl)carbamate:

Step 1:

Synthesis of N-(t-butoxycarbonyl)-N-isobutylglycine:

366 mg (5.01 mmol) of isobutylamine and 1.52 g (15.0 mmol) of triethylamine were dissolved in 10 ml of water. 695 mg (5.00 mmol) of bromoacetic acid was added to the obtained solution, and they were stirred for 1 hour. A solution of 1.63 g (7.50 mmol) of di(t-butyl) dicarbonate in 5 ml of 1,4-dioxane was added to the resultant mixture, and they were stirred for additional 1 hour. 10 ml of 1 N aqueous sodium hydroxide solution was added to the reaction mixture. After extracting with dichloromethane twice, 11 ml of 1 N aqueous hydrochloric acid solution was added to the aqueous layer. After extracting with dichloromethane 3 times, the obtained organic layer was dried over anhydrous sodium sulfate and then the solvent was evaporated under reduced pressure to obtain the title compound.

Yield: 829.1 mg (3.58 mmol), 72% $^1$H-NMR (CDCl$_3$): 0.89 (6H, d), 1.45 (9H, d), 1.83 (1H, m), 3.09 (2H, t), 3.93 (2H, d).

Step 2:

Synthesis of t-butyl 2-[4-(5H-dibenzo[a,d] [7] annulen-5-ylidene)-1-piperidinyl]-2-oxoethyl(isobutyl)carbamate:

178 mg (0.768 mmol) of N-(t-butoxycarbonyl)-N-isobutylglycine, 150 mg (0.549 mmol) of 4-(5H-dibenzo[a,d]annulen-5-ylidene)-1-piperidine, 210 mg (1.10 mmol) of 1-ethyl-3-(3'-dimethylaminopropyl)carbodiimide hydrochloride and 6 mg (0.05 mmol) of 4-dimethylaminopyridine were dissolved in 2 ml of dichloromethane. 139 mg (1.37 mmol) of triethylamine was added to the resultant solution and they were stirred for 1 hour. After the purification by the silica gel chromatography (hexane:ethyl acetate=95:5 to 4:1), the title compound was obtained.

Yield: 222.1 mg (0.456 mmol) (83%) MS (ESI, m/z) 487 (M+H)$^{+1}$H-NMR (CDCl$_3$): 0.87 (6H, d), 1.44 (9H, d), 1.85 (1H, m), 2.10-2.48 (4H, m), 3.42-3.40 (4H, m), 3.49 (1H, br s), 3.72-4.34 (3H, m), 6.92 (2H, s), 7.12-7.38 (8H, m).

Referential Example 27

Synthesis of t-butyl 2-[4-(5H-dibenzo[a,d] [7] annulen-5-ylidene)-1-piperidinyl]-2-oxoethyl(methyl)carbamate:

83.1 mg (0.439 mmol) of N-(t-butoxycarbonyl)-N-methylglycine, 100 mg (0.366 mmol) of 4-(5H-dibeno[a,d]annulen-5-ylidene)-1-piperidine, 105 mg (0.549 mmol) of 1-ethyl-3-(3'-dimethylaminopropyl)carbodiimide hydrochloride and 5 mg (0.04 mmol) of 4-dimethylaminopyridine were dissolved in 1.5 ml of dichloromethane. 74.0 mg (0.732 mmol) of triethylamine was added to the resultant solution and they were stirred for 1 hour. After the purification by the silica gel chromatography (hexane:ethyl acetate=89:11 to 65:35), the title compound was obtained.

Yield: 102 mg (0.229 mmol) (63%) MS (ESI, m/z) 445 (M+H)$^{+1}$H-NMR (CDCl$_3$): 1.45 (9H, d), 2.12-2.37 (4H, m), 2.91 (3H, s), 2.95-3.12 (2H, m), 3.49 (1H, br s), 3.82-4.18 (3H, m), 6.93 (2H, s), 7.14-7.36 (8H, m).

Referential Example 28

Synthesis of N-(t-butyl)-N'-{2-[4-(5H-dibenzo[a,d][7]annulen-5-ylidene)-1-piperidinyl]-2-oxoethyl}urea:

89.2 mg (0.55 mmol) of 1,1'-carbonylbis-1H-imidazole and 25.3 mg (0.25 mmol) of triethylamine were dissolved in 2.5 ml of tetrahydrofuran. A solution of 36.6 mg (0.50 mmol) of t-butylamine in 1 ml of tetrahydrofuran was slowly added to the resultant solution at 0° C. in argon stream. After stirring for 1 hour, a solution of 110.7 mg (0.30 mmol) of 2-[4-(5H-dibenzo [a,d][7] annulen-5-ylidene)-1-piperidinyl]-2-oxoethanamine hydrochloride and 30.3 mg (0.30 mmol) of triethylamine in 1 ml of tetrahydrofuran was slowly added thereto. After stirring for 2 hours, the solvent was evaporated and the product was purified by the silica gel chromatography (hexane:ethyl acetate=85:15 to 3:2) to obtain the title compound.

Yield: 70.7 mg (0.165 mmol), 66% MS (ESI, m/z) 430(M+H)$^{+1}$H-NMR (CDCl$_3$): 1.31 (9H, s), 2.10-2.35 (4H, m), 2.03-3.10 (2H, m), 3.40-3.52 (1H, m), 3.84-4.10 (3H, m), 4.56 (1H, br s), 5.30 (1H, s), 6.92 (2H, s), 7.14-7.24 (2H, m), 7.27-7.7.27 (6H, m).

Referential Example 29

Synthesis of t-butyl 2-({2-[4-(5H-dibenzo[a,d][7]annulen-5-ylidene)-1-piperidinyl]-2-oxoethyl}amino)-2-oxoethylcarbamate:

35.0 mg (0.095 mmol) of 2-[4-(5H-dibenzo[a,d][7]annulen-5-ylidene)-1-piperidinyl]-2-oxoethanamine hydrochloride, 19.7 mg (0.114 mmol) of N-t-butoxycarbonylglycine, 27.2 mg (0.142 mmol) of 1-ethyl-3-(3'-dimethylaminopropyl)carbodiimide hydrochloride and 1 mg (0.01 mmol) of 4-dimethylaminopyridine were dissolved in 1 ml of dichloromethane. 19.2 mg (0.190 mmol) of triethylamine was added to the obtained solution, and they were stirred for 1 hour. The product was purified by the silica gel chromatography (hexane:ethyl acetate=7:3 to 3:7) to obtain the title compound.

Yield: 31.8 mg (0.065 mmol), 69% MS (ESI, m/z) 488 (M+H)$^{+1}$H-NMR (CDCl$_3$): 1.45 (9H, s), 2.12-2.38 (4H, m), 2.94-3.11 (2H, m), 3.38-3.52 (2H, m), 3.85 (2H, d), 3.91-4.10

(3H, m), 5.06 (1H, br s), 6.92 (2H, s), 7.00 (1H, br s), 7.13-7.22 (2H, m), 7.22-7.39 (6H, m).

Referential Example 30

Synthesis of t-butyl 3-({2-[4-(5H-dibenzo[a,d][7]annulen-5-ylidene)-1-piperidinyl]-2-oxoethyl}amino)-3-oxopropylcarbamate:

35.0 mg (0.095 mmol) of 2-[4-(5H-dibenzo[a,d][7]annulen-5-ylidene)-1-piperidinyl]-2-oxoethanamine hydrochloride, 21.5 mg (0.114 mmol) of N-t-butoxycarbonylalanine, 27.2 mg (0.142 mmol) of 1-ethyl-3-(3'-dimethylaminopropyl)carbodiimide hydrochloride and 1 mg (0.01 mmol) of 4-dimethylaminopyridine were dissolved in 1 ml of dichloromethane. 19.2 mg (0.190 mmol) of triethylamine was added to the obtained solution, and they were stirred for 1 hour. The product was purified by the silica gel chromatography (hexane:ethyl acetate=7:3 to 3:7) to obtain the title compound.

Yield: 32.5 mg (0.065 mmol), 68% MS (ESI, m/z) 502 (M+H)$^{+1}$H-NMR (CDCl$_3$): 1.42 (9H, s), 2.12-2.38 (4H, m), 2.45 (2H, t), 3.04 (2H, m), 3.32-3.51 (3H, m), 3.87-4.10 (3H, m), 5.14 (1H, br s), 6.59 (1H, br s), 6.92 (2H, s), 7.13-7.40 (8H, m).

Referential Example 31

Synthesis of t-butyl 3-[4-(5H-dibenzo[a,d][7]annulen-5-ylidene)-1-piperidinyl]-3-oxopropyl(neopentyl)carbamate:

872 mg (10.0 mmol) of 2,2-dimethylpropylamine was dissolved in 10 ml of ethanol. 34.0 mg (0.50 mmol) of sodium ethoxide and 1.00 g (10.0 mmol) of ethylacrylic acid were added to the obtained solution, and they were stirred overnight. 1 ml of water was added to the reaction mixture and the organic solvent was evaporated under reduced pressure. 2.62 g (12.0 mmol) of di(t-butyl) dicarbonate and 25 ml of 1 N aqueous sodium hydroxide solution were added to the residue, and they were stirred for 3.5 hours. After extracting with dichloromethane twice, the aqueous layer was neutralized with 1 N aqueous hydrochloric acid solution. After extracting with dichloromethane 3 times, the extract was dried over anhydrous sodium sulfate and then the solvent was evaporated under reduced pressure. The obtained product was dissolved in 2 ml of dichloromethane. 145 mg (0.531 mmol) of 4-(5H-dibenzo[a,d][7]annulen-5-ylidene)-1-piperidine, 122 mg (0.637 mmol) of 1-ethyl-3-(3'-dimethylaminopropyl)carbodiimide hydrochloride and 6 mg (0.05 mmol) of 4-dimethylaminopyridine were added to the obtained solution. 107.5 mg (1.06 mmol) of triethylamine was further added to the reaction mixture, and they were stirred for 2 hour. The product was purified by the silica gel chromatography (hexane:ethyl acetate=89:11 to 4:1) to obtain the title compound.

Yield: 233 mg (0.452 mmol), 85% MS (ESI, m/z) 515 (M+H)$^{+1}$H-NMR (CDCl$_3$): 0.91 (9H, s), 1.43 (9H, s), 2.10-2.40 (4H, m), 2.48-2.71 (2H, m), 2.94-3.21 (4H, m), 3,49 (2H, t), 3.62 (1H, m), 3.85-3.98 (1H, m), 6.92 (2H, s), 7.14-7.23 (2H, m), 7.23-7.38 (6H, m).

Referential Example 32

Synthesis of t-butyl 2-[4-(10,11-dihydro-5H-dibenzo[b,f]azepin-5-yl)-1-piperidinyl]-2-oxoethylcarbamate:

60.0 mg (0.216 mmol) of 5-(4-piperidinyl)-10,11-dihydro-5H-dibenzo[b,f]azepine, 50.0 mg (0.258 mmol) of N-t-butoxycarbonylglycine, 62.1 mg (0.324 mmol) of 1-ethyl-3-(3'-dimethylaminopropyl)carbodiimide hydrochloride and 3 mg (0.03 mmol) of 4-dimethylaminopyridine were dissolved in 1 ml of dichloromethane. 43.7 mg (0.432 mmol) of triethylamine was added to the obtained solution, and they were stirred for 1 hour. The product was purified by the silica gel chromatography (hexane:ethyl acetate=89:11 to 65:35) to obtain the title compound.

Yield: 81.1 mg (0.186 mmol), 86% MS (ESI, m/z) 436 (M+H)$^{+1}$H-NMR (CDCl$_3$): 1.43 (9H, s), 1.60-1.77 (2H, m), 1.98-2.10 (2H, m), 2.77 (2H, br s), 3.15 (1H, m), 3.28 (1H, m), 3.38-3.60 (3H, m), 3.80-4.02 (3H, m), 4.20 (1H, m), 5.50(1H, br s), 6.93-7.00 (2H, m), 7.05-7.15 (6H, m).

Referential Example 33

Synthesis of t-butyl (1S)-1-{[4-(5H-dibenzo[a,d][7]annulen-5-ylidene)-1-piperidinyl]carbonyl}-3-methylbutyl(methyl)carbamate:

389 mg (1.59 mmol) of t-butoxycarbonyl-N-methyl-L-leucine, 311 mg (1.62 mmol) of 1-ethyl-3-(3'-dimethylaminopropyl)carbodiimide hydrochloride, 416 mg (1.52 mmol) of 4-(5H-dibenzo[a,d][7]annulen-5-ylidene)-1-piperidine and 0.22 ml (1.59 mmol) of triethylamine were stirred in 10 ml of dichloromethane at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=3:1) to obtain the title compound.

Yield: 368 mg (0.74 mmol), 48% MS (ESI, m/z) 501 (M+H)$^{+1}$H-NMR (CDCl$_3$): 0.86-0.98 (6H, dd), 1.34-1.65 (10H, m), 2.03-2.38 (4H, m), 2.64-2.84 (3H, m), 2.88-4.18 (6H, m), 4.78-5.12 (1H, m), 6.90-6.94 (2H, m), 7.11-7.38 (8H, m).

Referential Example 34

Synthesis of N-((1S)-1-{[4-(5H-dibenzo[a,d][7]annulen-5-ylidene)-1-piperidinyl]carbonyl}-3-methylbutyl)-N-methylamine hydrochloride:

344 mg (0.69 mmol) of t-butyl (1S)-1-{[4-(5H-dibenzo[a,d][7]annulen-5 -ylidene)-1-piperidinyl]carbonyl}-3-methylbutyl (methyl)carbamate was dissolved in 2 ml of 1,4-dioxane. 4 ml of 4 N hydrochloric acid/1,4-dioxane solution was added to the obtained solution, and they were stirred at room temperature for 5 hours and then concentrated under reduced pressure to obtain the title compound.

Yield: 301 mg (0.69 mmol), 100% MS (ESI, m/z) 401 (M+H)$^{+1}$H-NMR (CDCl$_3$): 0.86-1.04 (6H, m), 1.66-2.01 (5H, m), 2.16-2.56 (4H, m), 2.72 (3H, d), 2.94-3.26 (2H, m), 3.54-3.72 (1H, m), 3.94-4.08 (1H, m), 4.24-4.35 (1H, m), 6.89-6.93 (2H, m), 7.14-7.20 (2H, m), 7.22-7.38 (6H, m).

Referential Example 35

Synthesis of t-butyl 2-[[3-(5H-dibenzo[a,d][7]annulen-5-yl)propyl](methyl)amino]-2-oxoethylcarbamate:

134 mg (0.70 mmol) of 1-ethyl-3-(3'-dimethylaminopropyl)carbodiimide hydrochloride, 176 mg (0.59 mmol) of protriptyline hydrochloride and 0.176 ml (1.26 mmol) of triethylamine were added to 129 mg (0.74 mmol) of t-butoxycarbonylglydine in 5 ml of dichloromethane in the ice bath, and they were stirred at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=3:1) to obtain the title compound.

Yield: 228 mg (0.54 mmol), 92% MS (ESI, m/z) 421 (M+H)$^{+1}$H-NMR (CDCl$_3$): 1.13-1.30 (2H, m), 1.44 (9H, s), 1.64-1.76 (2H, m), 2.73 (3H, d), 3.27-3.42 (1H, m), 4.36 (1H, s), 5.31 (1H, s), 5.98 (1H, s), 6.49 (2H, s), 7.29-7.50 (8H, m).

Referential Example 36

Synthesis of t-butyl 2-[[3-(5H-dibenzo[a,d][7]annulen-5-ylidene)propyl](methyl)amino]-2-oxoethylcarbamate:

Step 1

Synthesis of 3-(5H-dibenzo[a,d][7]annulen-5-ylidene)-N-methyl-1-propanamine:

20 ml of saturated aqueous sodium hydrogencarbonate solution was added to 2.467 g (7.91 mmol) of cyclobenzaprine hydrochloride in 20 ml of chloroform, and they were stirred at room temperature for 10 minutes. After extracting with chloroform, the organic layer was dried over anhydrous sodium sulfate and then concentrated under reduced pressure. 15 ml of toluene was added to the residue, and they were heated at 80° C. 4.0 ml (41.8 mmol) of ethyl chloroformate was added thereto, and they were stirred at 80° C. overnight. 4.0 ml (41.8 mmol) of ethyl chloroformate was added to the reaction mixture, and they were stirred under heating for 2 days. Water was added to the reaction mixture. After extracting with ethyl acetate, the organic layer was dried over anhydrous sodium sulfate and then concentrated under reduced pressure. The residue was purified by the silica gel chromatography (hexane:ethyl acetate=1:1). 11.4 ml of 1-butanol and 1.97 g (35.1 mmol) of powdery potassium hydroxide were added to the obtained product, and they were stirred under heating at 120° C. for 4 hours. The reaction mixture was poured in water at room temperature. After the extraction with chloroform, the organic layer was dried over anhydrous sodium sulfate and then concentrated under reduce pressure to obtain the title compound.

Yield: 1.725 g (6.60 mmol), 83% MS (ESI, m/z) 262 (M+H)$^{+1}$H-NMR (CDCl$_3$): 2.26-2.35 (2H, m), 2.30 (3H, s), 2.53-2.66 (2H, m), 5.53 (1H, t), 6.86 (2H, d), 7.21-7.37 (8H, m).

Step 2

Synthesis of t-butyl 2-[[3-(5H-dibenzo[a,d][7]annulen-5-ylidene)propyl](methyl)amino]-2-oxoethylcarbamate:

105 mg (0.60 mmol) of t-butoxycarbonylglycine, 111 mg (0.58 mmol) of 1-ethyl-3-(3'-dimethylaminopropyl)carbodiimide hydrochloride, 133 mg (0.51 mmol) of 3-(5H-dibenzo[a,d][7]annulen-5-ylidene)-N-methyl-1-propanamine and 0.08 ml (0.57 mmol) of triethylamine were stirred in 5 ml of dichloromethane at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=2:1) to obtain the title compound.

Yield: 130 mg (0.31 mmol), 61% MS (ESI, m/z) 419 (M+H)$^{+1}$H-NMR (CDCl$_3$): 1.45 (9H, d), 2.23-2.52 (2H, m), 2.68 (3H, d), 3.10-3.58 (2H, m), 3.72-3.88 (2H, m), 5.40-5.53 (2H, m), 6.84-6.88 (2H, m), 7.15-7.40 (8H, m).

Referential Example 37

Synthesis of t-butyl (1S)-1-{[[3-(5H-dibenzo[a,d][7]annulen-5-ylidene)propyl] (methyl) amino]carbonyl}-3-methylbutyl (methyl) carbamate:

280 mg (1.14 mmol) of t-butoxycarbonyl-N-methyl-L-leucine, 204 mg (1.06 mmol) of 1-ethyl-3-(3'-dimethylaminopropyl)carbodiimide hydrochloride, 271 mg (1.04 mmol) of 3-(5H-dibenzo[a,d][7]annulen-5-ylidene)-N-methyl-1-propanamine and 0.15 ml (1.08 mmol) of triethylamine were stirred in 10 ml of dichloromethane at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=82:18) to obtain the title compound.

Yield: 178 mg (0.37 mmol), 35% MS (ESI, m/z) 489 (M+H)$^{+1}$H-NMR (CDCl$_3$): 0.63-0.96 (6H, m), 1.24-1.62 (11H, m), 2.22-2.91 (9H, m), 3.10-3.70 (2H, m), 4.66-5.08 (1H, m), 5.41-5.58 (1H, m), 6.79-6.91 (2H, m), 7.16-7.38 (8H, m).

Referential Example 38

Synthesis of (2S)-N-[3-(5H-dibenzo[a,d][7]annulen-5-ylidene)propyl]-N,4-dimethyl-2-(methylamino)pentanamide hydrochloride:

5 ml of dichloromethane and 2.5 ml of trifluoroacetic acid were added to 169 mg (0.35 mmol) of t-butyl (1S)-1-{[[3-(5H-dibenzo[a,d][7]annulen-5-ylidene)propyl] (methyl) amino]carbonyl}-3-methylbutyl(methyl)carbamate, and they were stirred at room temperature for 2 hours. The reaction mixture was concentrated under reduced pressure. 1 N aqueous sodium hydroxide solution was added thereto to make it basic. After extracting with ethyl acetate, the organic layer was dried over anhydrous sodium sulfate and then concentrated under reduced pressure. The residue was dissolved in 5 ml of 1,4-dioxane. 4 N hydrochloric acid/1,4-dioxane solution was added to the obtained solution. The resultant mixture was concentrated under reduced pressure to obtain the title compound.

Yield: 145 mg (0.34 mmol) 99% MS (ESI, m/z) 389 (M+H)$^{+1}$H-NMR (CDCl$_3$): 0.74-0.94 (6H, m), 1.40-1.75 (2H, m), 2.06-2.83 (9H, m), 3.08-3.60 (2H, m), 3.75-4.11 (1H, m), 5.40-5.51 (1H, m), 6.77-6.92 (2H, m), 7.16-7.41 (8H, m).

Referential Example 39

Synthesis of t-butyl 2-[[3-(10,11-dihydro-5H-dibenzo[a,d][7]annulen-5-ylidene)propyl](methyl)amino]-2-oxoethylcarbamate:

281 mg (1.47 mmol) of 1-ethyl-3-(3'-dimethylaminopropyl)carbodiimide hydrochloride, 281 mg (1.47 mmol) of nortriptyline hydrochloride and 0.40 ml (2.87 mmol) of triethylamine were added to 251 mg (1.44 mmol) of t-butoxycarbonylglycine in 10 ml of dichloromethane in the ice bath, and they were stirred at room temperature overnight. Saturated aqueous sodium hydrogencarbonate solution was added to the reaction mixture. After extracting with dichloromethane, the organic layer was dried over anhydrous sodium sulfate and then concentrated under reduced pressure. The residue was purified by the silica gel chromatography (hexane:ethyl acetate=4:1) to obtain the title compound.

Yield: 203 mg (0.48 mmol), 33% MS (ESI, m/z) 421 (M+H)$^{+1}$H-NMR (CDCl$_3$): 1.44 (9H, s), 1.64-1.76 (2H, m), 2.30-2.48 (2H, m), 2.77 (3H, d), 2.85-3.56 (6H, m), 3.83-3.95 (2H, m), 5.43-5.75 (1H, brd), 5.79 (1H, dt), 7.00-7.28 (8H, m).

Referential Example 40

Synthesis of t-butyl 2-[(5H-dibenzo[a,d][7]annulen-5-ylidenacetyl)amino]ethylcarbamate:

Step 1

Synthesis of 5H-dibenzo[a,d][7]annulen-5-ylidenacetic Acid:

890 mg (22.3 mmol) of sodium hydride (60% oily) was added to 4.99 g (22.3 mmol) of ethyl diethylphosphonoacetate in 55 ml of dimethyl sulfoxide, and they were stirred at room temperature overnight. 4.58 g (22.2 mmol) of 5H-dibenzo[a,d]-5-cycloheptenone was added to the reaction mixture, and they were stirred at room temperature for 1 hour 15 minutes and then stirred under heating at 100° C. for 2 days. Dimethyl sulfoxide was evaporated under reduced pressure. 20 ml of ethanol and 20 ml of 6 N aqueous sodium hydroxide solution were added to the residue, and they were stirred under heating at 100° C. for 3 days. The reaction mixture was concentrated under reduced pressure and then acidified with 1 N hydrochloric acid. After extracting with ethyl acetate, the organic layer was dried over anhydrous sodium sulfate and then concentrated under reduced pressure. The residue was purified by the silica gel chromatography (hexane:ethyl acetate=1:1) to obtain the title compound.

Yield: 1.552 g (6.25 mmol), 28% MS (ESI, m/z) 247 (M−H)$^{-1}$H-NMR (CDCl$_3$): 5.90 (1H, s), 6.94 (2H, q), 7.30-7.46 (8H, m).

Step 2

Synthesis of t-butyl 2-[(5H-dibenzo[a,d][7]annulen-5-ylidenacetyl)amino]ethylcarbamate:

173 mg (0.70 mmol) of 5H-dibenzo[a,d][7]annulen-5-ylidenacetic acid, 124 mg (0.77 mmol) of t-butyl N-(2-aminoethyl)carbamate, 143 mg (0.75 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with saturated aqueous sodium hydrogencarbonate solution and the organic layer was dried over anhydrous sodium sulfate and then concentrated under reduced pressure. The residue was purified by the silica gel chromatography (hexane:ethyl acetate=7:3) to obtain the title compound.

Yield: 185 mg (0.47 mmol), 68% MS (ESI, m/z) 391 (M+H)$^{+1}$H-NMR (CDCl$_3$): 1.44 (9H, s), 2.78-3.08 (3H, m), 3.27-3.42 (1H, m), 4.36 (1H, s), 5.31 (1H, s), 5.98 (1H, s), 6.49 (2H, s), 7.29-7.50 (8H, m).

Referential Example 41

Synthesis of t-butyl 3-[(5H-dibenzo[a,d][7]annulen-5-ylidenacetyl)amino]propylcarbamate:

173 mg (0.70 mmol) of 5H-dibenzo[a,d][7]annulen-5-ylidenacetic acid, 130 mg (0.75 mmol) of t-butyl N-(3-aminopropyl)carbamate, 149 mg (0.78 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with 0.5 N aqueous sodium hydroxide solution and the organic layer was dried over anhydrous sodium sulfate and then concentrated under reduced pressure. The residue was purified by the silica gel chromatography (hexane:ethyl acetate=7:3) to obtain the title compound.

Yield: 232 mg (0.57 mmol), 82% MS (ESI, m/z) 403 (M−H)$^{-1}$H-NMR (CDCl$_3$): 1.24-1.37 (2H, m), 1.42 (9H, s), 2.82 (2H, q), 2.90-3.04 (1H, m), 3.15-3.30 (1H, m), 4.77 (1H, s), 5.48 (1H, s), 5.98 (1H, s), 6.93 (2H, d), 7.29-7.50 (8H, m).

Referential Example 42

Synthesis of t-butyl 4-(5H-dibenzo[a,d][7]annulen-5-ylidenacetyl)-1-piperazine carboxylate:

172 mg (0.69 mmol) of 5H-dibenzo[a,d][7]annulen-5-ylideneacetic acid, 144 mg (0.78 mmol) of t-butyl 1-piperazinecarboxylate, 148 mg (0.77 mmol) of 1-ethyl-3-(3'-dimethylaminopropyl)carbodiimide hydrochloride and 0.11 ml (0.79 mmol) of triethylamine were stirred in 5 ml of dichloromethane at room temperature overnight. The reaction mixture was washed with 0.5 N aqueous sodium hydroxide solution and the organic layer was dried over anhydrous sodium sulfate and then concentrated under reduced pressure. The residue was purified by the silica gel chromatography (hexane:ethyl acetate=2:1) to obtain the title compound.

Yield: 273 mg (0.66 mmol), 95% MS (ESI, m/z) 417 (M+H)$^{+1}$H-NMR (CDCl$_3$): 1.42 (9H, s), 2.01-2.12 (1H, m), 2.71-2.84 (1H, m), 2.96-3.10 (2H, m), 3.11-3.26 (2H, m), 3.35-3.49 (1H, m), 3.55-3.69 (1H, m), 5.94 (1H, s), 6.83-6.96 (2H, m), 7.28-7.57 (8H, m).

Referential Example 43

Synthesis of 1-ethyl-1-methylpropyl 2-[4-[(5H-dibenzo[a,d][7]annulen-5-ylidene)-1-piperidinyl]-2-oxoethylcarbamate:

Step 1

Synthesis of ethyl {[(1-ethyl-1-methylpropoxy)carbonyl]amino}acetate:

0.500 ml (4.01 mmol) of ethyl isocyanatoacetate was dissolved in dichloromethane. 0.05 ml of 4 N hydrochloric acid/1,4-dioxane solution was added to the obtained solution, and they were stirred at room temperature for 5 minutes. 0.547 ml (4.41 mmol) of 3-methyl-3-pentanol was added to the reaction mixture, and they were stirred overnight. After the concentration under reduced pressure, ethyl acetate was added to the reaction mixture, and they were washed with saturated aqueous sodium hydrogencarbonate solution, dried over anhydrous magnesium sulfate and then concentrated under reduced pressure. The residue was washed with diethyl ether. The filtrate was concentrated under reduced pressure to obtain the title compound.

Yield: 622 mg (2.69 mmol), 67% $^1$H-NMR (CDCl$_3$): 0.85 (6H, t), 1.26 (3H, t), 1.35 (3H, s), 1.66-1.91 (4H, m), 3.87 (2H, d), 4.19 (2H, q), 5.04 (1H, br s).

Step 2

Synthesis of {[(1-ethyl-1-methylpropoxy)carbonyl]amino}acetic Acid:

300 mg (1.30 mmol) of ethyl {[(1-ethyl-1-methylpropoxy)carbonyl]-amino}acetate was dissolved in 2.5 ml of a solvent mixture of methanol:water (2.3:1). 1.56 ml of 1 N aqueous lithium hydroxide solution was added to the obtained solution. After stirring at room temperature for 2 hours, "DOWEX" (50W-X2 100 to 200 mesh H form) (an exchange resin of The Dow Chemical Company) was added to the reaction mixture under gentle stirring until pH of the mixture had become 5. The resin was obtained by the filtration under suction and then the filtrate was concentrated under reduced pressure and then dried to obtain the title compound.

Yield: 284 mg (1.40 mmol), 100% MS (ESI, m/z) 202 (M–H)$^{-1}$H-NMR (CDCl$_3$): 0.82 (6H, br t), 1.33 (3H, s), 1.67-1.84 (4H, m), 3.69 (2H, br s), 5.86 (1H, br s).

Step 3

Synthesis of 1-ethyl-1-methylpropyl 2-[4-(5H-dibenzo[a,d][7]annulen-5-ylidene)-1-piperidinyl]-2-oxoethylcarbamate:

284 mg (1.40 mmol) of {[(1-ethyl-1-methylpropoxy)carbonyl]amino}acetic acid, 320 mg (1.17 mmol) of 4-(5H-dibenzo[a,d][7]annulen-5-ylidene)-piperidine and 322 mg (1.68 mmol) of 1-ethyl-3-(3'-dimethylaminopropyl)carbodiimide hydrochloride were dissolved in a mixed solvent of 15 ml of dichloromethane and 5 ml of dimethylformamide. 0.23 ml (1.68 mmol) of triethylamine and 14.7 mg (0.12 mmol) of dimethylaminopyridine were added to the obtained solution, and they were stirred at room temperature overnight. After the concentration under reduced pressure, ethyl acetate was added to the reaction mixture. The resultant mixture was washed with saturated aqueous sodium chloride solution. The organic layer was dried over anhydrous magnesium sulfate and then concentrated under reduced pressure. The obtained residue was purified by the silica gel chromatography (hexane: dichloromethane=95:5 to 2:3) to obtain the title compound.

Yield: 204 mg (0.445 mmol) (38%) MS (ESI, m/z) 459 (M+H)$^{+1}$H-NMR (CDCl$_3$): 0.85 (6H, t), 1.35 (3H, s), 1.66-1.91 (4H, m), 2.14-2.33 (4H, m), 2.97-3.06 (2H, m), 3.39-3.46 (1H, m), 3.84-4.00 (3H, m), 5.54 (1H, br s), 6.92 (2H, s), 7.15-7.18 (2H, m), 7.23-7.28 (2H, m), 7.31-7.37 (4H, m).

Referential Example 44

Synthesis of N-(t-butyl)-4-[4-(10,11-dihydro-5H-dibenzo[b,f]azepin-5-yl)-1-piperidinyl]-4-oxobutanamide:

Step 1

Synthesis of 4-(t-butylamino)-4-oxobutanoic Acid:

3.07 g (30.6 mmol) of succinic anhydride was suspended in 30 ml of dichloromethane. 4.1 ml (34.5 mmol) of t-butylamine was dropped into the suspension, and the resultant mixture was stirred at room temperature for 1 hour. White crystals thus formed were washed with ethyl acetate and then dissolved in 40 ml of 1 N aqueous sodium hydroxide solution. The resultant solution was stirred at room temperature for 2 hours and then acidified with 1 N aqueous hydrochloric acid solution under cooling with ice. After extracting with ethyl acetate, the organic layer was dried over anhydrous sodium sulfate and then concentrated under reduced pressure to obtain the title compound.

Yield: 2.75 g (15.9 mmol), 52% MS (ESI, m/z) 172 (M–H)$^{-1}$H-NMR (DMSO-d$_6$): 1.20 (9H, s), 2.21-2.26 (2H, m), 2.32-2.37 (2H, m), 7.39 (1H, br s).

Step 2

Synthesis of N-(t-butyl)-4-[4-(10,11-dihydro-5H-dibenzo[b,f]azepin-5-yl)-1-piperidinyl]-4-oxobutanamide:

83.2 mg (0.299 mmol) of 5-(4-piperidinyl)-10,11-dihydro-5H-dibenzo[b,f]azepine, 62.2 mg (0.359 mmol) of 4-(t-butylamino)-4-oxobutanoic acid and 82.6 mg (0.431 mmol) of 1-ethyl-3-(3'-dimethylaminopropyl)carbodiimide hydrochloride were dissolved in 5 ml of dichloromethane. 0.06 ml (0.431 mmol) of triethylamine and 3.67 mg (0.03 mmol) of 4-dimethylaminopyridine were added to the obtained solution, and they were stirred at room temperature overnight. The reaction mixture was concentrated under reduced pressure. Ethyl acetate was added thereto. After washing with 1 N aqueous hydrochloric acid solution, the organic layer was dried over anhydrous magnesium sulfate and then concentrated under reduced pressure. The residue was purified by the silica gel chromatography (dichloromethane: methanol=9:1) to obtain the title compound.

Yield: 102 mg (0.236 mmol), 79% MS (ESI, m/z) 434 (M+H)$^{+1}$H-NMR (CDCl$_3$): 1.31 (9H, s), 1.58-1.70 (2H, m), 1.96-2.11 (2H, m), 2.37-2.42 (2H, m), 2.50-2.82 (4H, m), 3.14-3.26 (2H, m), 3.49 (2H, br s), 3.62-3.69 (1H, m), 3.92-4.00 (1H, m), 4.14-4.21 (1H, m), 5.78 (1H, br s), 6.92-6.99 (2H, m), 7.08-7.10 (6H, m).

Referential Example 45

Synthesis of N-{2-[4-(5H-dibenzo[a,d][7]annulen-5-ylidene)-1-piperidinyl]-2-oxoethyl}-N,N-dimethylurea:

200 mg (0.545 mmol) of 2-[4-(5H-dibenzo[a,d][7]annulen-5-ylidene)-1-piperidinyl]-2-oxoethanamine hydrochloride was suspended in 2 ml of dichloromethane. 0.19 ml of triethylamine was added to the obtained suspension. A solution of 70.3 mg (0.654 mmol) of N,N-dimethylcarbamoyl chloride in 3 ml of dichloromethane was added dropwise to the resultant mixture under cooling with ice, and they were stirred at room temperature for 30 minutes. Dichloromethane was concentrated under reduced pressure. Ethyl acetate was added to the residue. The resultant mixture was washed with saturated aqueous sodium hydrogencarbonate solution. White crystals precipitated in the organic layer was taken by the filtration to obtain the title compound.

Yield: 158 mg (0.394 mmol), 72% MS (ESI, m/z) 430 (M+H)$^{+1}$H-NMR (CDCl$_3$): 2.20-2.33 (4H, m), 2.93 (6H, s), 3.01-3.10 (2H, m), 3.44-3.54 (1H, m), 3.92-4.05 (3H, m), 5.51 (1H, br s), 6.92 (2H, s), 7.15-7.19 (2H, m), 7.23-7.28 (2H, m), 7.32-7.36 (4H, m).

Referential Example 46

Synthesis of N-{2-[4-(5H-dibenzo[a,d][7]annulen-5-ylidene)-1-piperidinyl]-2-oxoethyl}-1-piperidinecarboxamide:

200 mg (0.545 mmol) of 2-[4-(5H-dibenzo[a,d][7]annulen-5-ylidene)-1-piperidinyl]-2-oxoethanamine hydrochloride was suspended in 2 ml of dichloromethane. 0.19 ml of triethylamine was added to the obtained suspension. A solution of 96.5 mg (0.654 mmol) of 1-piperidinecarbonyl chloride in 3 ml of dichloromethane was added dropwise to the resultant mixture under cooling with ice, and they were stirred at room temperature for 30 minutes. Dichloromethane was concentrated under reduced pressure. Ethyl acetate was added to the residue. The resultant mixture was washed with saturated aqueous sodium hydrogencarbonate solution. The organic layer was dried over anhydrous magnesium sulfate and then concentrated under reduced pressure. The residue was purified by the basic silica gel chromatography (hexane: ethyl acetate=4:1 to 1:4) to obtain the title compound.

Yield: 201 mg (0.455 mmol), 84% MS (ESI, m/z) 442 (M+H)$^{+1}$H-NMR (CDCl$_3$): 1.49-1.62 (6H, m), 2.15-2.33 (4H, m), 3.02-3.08 (2H, m), 3.34-3.37 (4H, m), 3.45-3.51 (1H, m), 3.90-4.11 (3H, m), 5.58 (1H, br s), 6.92 (2H, s), 7.16-7.18 (2H, m), 7.28-7.35 (6H, m).

Referential Example 47

Synthesis of N-[2-(t-butylamino)-2-oxoethyl]-4-(5H-dibenzo[a,d][7]annulen-5-ylidene)-1-piperidinecarboxamide:

Step 1

Synthesis of t-butyl ({[4-(5H-dibenzo[a,d][7]annulen-5-ylidene)-1-piperidinyl]carbonyl}amino)acetate:

475 mg (2.93 mmol) of N,N'-carbonyldiimidazole was dissolved in 10 ml of anhydrous tetrahydrofuran. 0.45 ml (3.29 mmol) of triethylamine was added to the obtained solution, and they were stirred at room temperature for 10 minutes. The reaction mixture was cooled with ice, and 460 mg (2.74 mmol) of glycine t-butyl hydrochloride was added dropwise to the mixture during a period of about 10 minutes, and they were stirred at room temperature for 1 hour. After cooling with ice, 500 mg (1.83 mmol) of 4-(5H-dibenzo[a,d][7]annulen-5-ylidene)piperidine was added to the resultant mixture, and they were stirred at room temperature overnight. Water was added to the reaction mixture. After extracting with ethyl acetate followed by drying over anhydrous magnesium sulfate, the product was concentrated under reduced pressure. The residue thus obtained was purified by the silica gel chromatography (dichloromethane: methanol=95:5 to 2:3) to obtain the title compound.

Yield: 752 mg (1.75 mmol), 95% MS (ESI, m/z) 431 (M+H)$^{+1}$H-NMR (CDCl$_3$): 1.46 (9H, s), 2.12-2.20 (2H, m), 2.28-2.33 (2H, m), 3.01-3.09 (2H, m), 3.52-3.59 (2H, m), 3.90 (2H, d), 4.91 (1H, br t).

Step 2

Synthesis of ({[4-(5H-dibenzo[a,d][7]annulen-5-ylidene)-1-piperidinyl]carbonyl}amino)acetic Acid:

752 mg (1.75 mmol) of t-butyl ({[4-(5H-dibenzo[a,d][7]annulen-5-ylidene)-1-pipieidinyl]carbonyl}amino)acetate was dissolved in 8 ml of dichloromethane. 2 ml of trifluoroacetic acid was added to the obtained solution under cooling with ice, and they were stirred at room temperature for 1 hour. After the concentration under reduced pressure, the reaction mixture was dissolved in ethyl acetate. Water was added thereto and white crystals thus precipitated were taken by the filtration to obtain the title compound.

Yield: 498 mg (1.33 mmol), 76% MS (ESI, m/z) 373 (M−H)$^{-1}$H-NMR (DMSO-d$_6$): 1.85-1.93 (2H, m), 2.16-2.25 (2H, m), 3.03-3.11 (2H, m), 3.39-3.47 (2H, m), 3.62 (2H, d), 6.82 (1H, br t), 6.96 (2H, s), 7.19-7.30 (4H, m), 7.35-7.40 (4H, m), 12.28 (1H, br s).

Step 3

Synthesis of N-[2-(t-butylamino)-2-oxoethyl]-4-(5H-dibenzo[a,d][7]annulen-5-ylidene)-1-piperidinecarboxamide:

300 mg (0.801 mmol) of ({[4-(5H-dibenzo[a,d][7]annulen-5-ylidene)-1-piperidinyl]carbonyl}amino)acetic acid, 1.0 ml (0.961 mmol) of t-butylamine and 230 mg (1.20 mmol) of 1-ethyl-3-(3'-dimethylaminopropyl)carbodiimide hydrochloride were dissolved in 10 ml of dichloromethane. The obtained solution was stirred at room temperature for 1 hour. Water was added to the reaction mixture. After extracting with dichloromethane, the dichloromethane layer was dried over anhydrous magnesium sulfate and then concentrated under reduced pressure. The residue thus obtained was purified by the silica gel chromatography (dichloromethane: methanol=4:1 to 1:9) to obtain the title compound.

Yield: 198 mg (0.476 mmol), 60% MS (ESI, m/z) 430 (M+H)$^{+1}$H-NMR (CDCl$_3$): 1.34 (9H, s), 2.11-2.18 (2H, m), 2.27-2.36 (2H, m), 3.00-3.09 (2H, m), 3.52-.3.59 (2H, m), 3.79 (2H, d), 5.28 (1H, br s), 6.01 (1H, br s), 6.91 (2H, s), 7.15-7.18 (2H, m), 7.22-7.27 (2H, m), 7.30-7.35 (4H, m).

Referential Example 48

Synthesis of N-[2-[4-(5H-dibenzo[a,d][7]annulen-5-ylidene)-1-piperidinyl]-1-(hydroxymethyl)-2-oxoethyl]-1-piperidinecarboxamide:

Step 1

Synthesis of methyl 3-hydroxy-2-[(1-piperidinylcarbonyl)amino]propionate:

1.00 g (6.43 mmol) of serine methyl ester hydrochloride and 960 mg (14.1 mmol) of imidazole were dissolved in 10 ml of dichloromethane. 10 ml of a solution of 1.07 g (7.07 mmol) of t-butyldimethylchlorosilane in dichloromethane was added dropwise to the obtained solution under cooling with ice, and they were stirred at room temperature for 1 hour. After concentrating under reduced pressure, ethyl acetate was added to the residue. The reaction mixture was washed with saturated aqueous ammonium chloride solution, then dried over anhydrous magnesium sulfate and concentrated under reduced pressure. The residue was dissolved in 10 ml of dichloromethane. 1.35 ml (9.65 mmol) of triethylamine and 0.97 ml (7.72 mmol) of 1-piperidinecarbonyl chloride were added dropwise to the obtained solution under cooling with ice, and they were stirred at room temperature overnight. 20 ml of chloroform was added to the reaction mixture, and they were stirred at 50° C. for 3 hours and then concentrated under reduced pressure. The residue was dissolved in 15 ml of methanol. 10 ml of 2 N hydrochloric acid was added dropwise to the obtained solution under cooling with ice, and they were stirred at room temperature for 2 hours. After the concentration under reduced pressure, ethyl acetate was added to the residue. The product was washed with 1 N aqueous hydrochloric acid solution, dried over anhydrous magnesium sulfate and concentrated under reduced pressure. The residue thus obtained was purified by the silica gel chromatography (dichloromethane:methanol=1:0 to 9:1) to obtain the title compound.

Yield: 428 mg (1.86 mmol), 29% MS (ESI, m/z) 231 (M+H)$^{+1}$H-NMR (CDCl$_3$): 1.57-1.59 (6H, m), 2.98 (1H, br s), 3.36-3.39 (4H, m), 3.79 (3H, s), 3.87-3.99 (2H, m), 4.58-4.63 (1H, m), 5.43 (1H, br d).

Step 2

Synthesis of 3-hydroxy-2-[(1-piperidinylcarbonyl)amino]propionic Acid:

200 mg (0.869 mmol) of methyl 3-hydroxy-2-[(1-piperidinylcarbonyl) amino]propionate was dissolved in 6 ml of a solvent mixture of methanol tetrahydrofuran (1:1). 1.04 ml (1.04 mmol) of 1 N aqueous lithium hydroxide solution was added to the obtained solution, and they were stirred at room temperature for 30 minutes. The reaction mixture was concentrated under reduced pressure, and the concentrate was acidified with 1 N aqueous hydrochloric acid solution. After extracting with ethyl acetate, the organic layer was dried over anhydrous magnesium sulfate and then concentrated under reduced pressure to obtain the title compound.

Yield: 64 mg (0.296 mmol) (34%) MS (ESI, m/z) 215 (M−H)$^{-1}$H-NMR (CD$_3$OD): 1.51-1.69 (6H, m), 3.17-3.20 (1H, m), 3.38-3.42 (4H, m), 3.80-3.94 (2H, m), 4.36 (1H, t).

Step 3

Synthesis of N-[2-[4-(5H-dibenzo[a,d] [7]annulen-5-ylidene)-1-piperidinyl]-1-(hydroxymethyl)-2-oxoethyl]-1-piperidinecarboxamide:

64.0 mg (0.296 mmol) of 3-hydroxy-2-[(1-piperidinylcarbonyl)amino]propionic acid, 80.9 mg (0.296 mmol) of 4-(5H-dibenzo[a,d][7]annulen-5-ylidene)piperidine and 85.1 mg (0.444 mmol) of 1-ethyl-3-(3'-dimethylaminopropyl)carbodiimide hydrochloride were dissolved in 10 ml of dichloromethane. 0.091 ml (0.651 mmol) of triethylamine was added to the obtained solution, and they were stirred at room temperature overnight. The reaction mixture was concentrated under reduced pressure. Ethyl acetate was added to the residue. After washing with saturated aqueous sodium chloride solution, the reaction product was dried over anhydrous magnesium sulfate and then concentrated under reduced pressure. The resultant product was purified by the silica gel chromatography (dichloromethane: methanol=9:1) to obtain the title compound.

Yield: 100 mg (0.213 mmol) (72%) MS (ESI, m/z) 472 (M+H)$^+$ $^1$H-NMR (CDCl$_3$): 1.49-1.62 (6H, m), 2.26-2.35 (4H, m), 2.92-3.37 (6H, m), 3.65-3.76 (3H, m), 3.83-4.01 (1H, m), 4.08-4.31 (1H, m), 4.76-4.82 (1H, m), 5.87-5.92 (1H, m), 6.92 (2H, d), 7.14-7.18 (2H, m), 7.23-7.28 (2H, m), 7.32-7.37 (4H, m).

Referential Example 49

Synthesis of N-[2-(t-butylamino)-1-(hydroxymethyl)-2-oxoethyl]-4-(5H-dibenzo[a,d][7]annulen-5-ylidene)-1-piperidinecarboxamide:

Step 1

Synthesis of 2-{[(benzyloxy)carbonyl]amino}-3-{[t-butyl(dimethyl)silyl]oxy}propionic Acid:

1.50 g (6.27 mmol) of N-[(benzyloxy)carbonyl]-(DL)-serine was dissolved in 10 ml of N,N-dimethylformamide. 885 mg (13.2 mmol) of imidazole and 1.98 g (13.2 mmol) of t-butyldimethylchlorosilane were added to the obtained solution at 0° C., and they were stirred overnight. Water was added to the reaction mixture and they were stirred for 10 minutes. After extracting with ethyl acetate 3 times followed by the drying over anhydrous sodium sulfate, the solvent was evaporated under reduced pressure to obtain the title compound.

Yield: 2.21 g (6.27 mmol), 100% $^1$H-NMR (CDCl$_3$): −0.01-0.10 (6H, m), 0.62-0.94 (9H, m), 3.60-3.80 (1H, m), 4.05-4.15 (1H, m), 4.32-4.48 (1H, m), 5.05-5.20 (2H, m), 5.59 (1H, s), 7.28-7.40 (5H, m).

Step 2

Synthesis of 2-{[(benzyloxy)carbonyl]amino}-N-(t-butyl)-3-{[t-butyl(dimethyl)silyl]oxy}propylamide:

2.21 g (6.27 mmol) of 2-{[(benzyloxy)carbonyl]amino}-3-{[t-butyl(dimethyl)silyl]oxy}propionic acid, 1.44 g (7.52 mmol) of 1-ethyl-3-(3'-dimethylaminopropyl)carbodiimide hydrochloride, 79.0 mg (0.63 mmol) of 4-dimethylaminopyridine and 952 mg (9.41 mmol) of triethylamine were dissolved in 10 ml of dichloromethane. 504 mg (6.90 mmol) of t-butylamine was added to the obtained solution, and they were stirred overnight. Saturated aqueous ammonium chloride solution was added to the reaction mixture. After extracting with ethyl acetate 3 times followed by the drying over anhydrous sodium sulfate, the solvent was evaporated under reduced pressure. The residue was purified by the silica gel chromatography (hexane:ethyl acetate=97:3 to 88:12) to obtain the title compound.

Yield: 1.07 g (2.62 mmol), 42% $^1$H-NMR (CDCl$_3$): 0.10 (6H, m), 0.90 (9H, s), 1.33 (9H, s), 3.56 (1H, t), 3.94-4.09 (2H, m), 5.12 (2H, m), 5.67 (1H, s), 6.30 (1H, m), 7.28-7.39 (5H, m).

Step 3

Synthesis of 2-amino-N-(t-butyl)-3-{[t-butyl(dimethyl)silyl]oxy}propylamide:

500 mg of palladium carbon (10% w/v) in 5 ml of ethanol was added to 990 mg (2.42 mmol) of 2-{[(benzyloxy)carbonyl]amino}-N-(t-butyl)-3-{[t-butyl(dimethyl)silyl]oxy}propylamide, and they were stirred in hydrogen gas atmosphere overnight. The reaction mixture was filtered, and the solvent was evaporated under reduced pressure to obtain the title compound. After drying on anhydrous sodium sulfate, the solvent was evaporated under reduced pressure to obtain the title compound.

Yield: 620 mg (2.26 mmol), 93% $^1$H-NMR (CDCl$_3$): 0.06 (6H, s), 0.89 (9H, s), 1.24 (9H, s), 1.63 (2H, s), 3.30 (1H, t), 3.76 (2H, d), 7.10 (1H, br s).

Step 4

Synthesis of N-[2-(t-butylamino)-1-({[t-butyl(dimethyl)silyl]oxy}methyl)-2-oxoethyl]-4-(5H-dibenzo[a,d] [7]annulen-5-ylidene)-1-piperidinecarboxamide:

59.1 mg (0.364 mmol) of 1,1'-carbonylbis-1H-imidazole and 36.9 mg (0.364 mmol) of triethylamine were dissolved in 4 ml of dichloromethane. A solution of 100 mg (0.364 mmol) of 2-amino-N-(t-butyl)-3-{[t-butyl(dimethyl)silyl]oxy}propylamide in 2 ml of dichloromethane was slowly added to the obtained solution. After stirring for 2 hours, a solution of 99.6 mg (0.364 mmol) of 2-[4-(5H-dibenzo[a,d][7]annulen-5-ylidene)-1-piperidinyl]ethylamine and 36.9 mg (0.364 mmol) of triethylamine in 2 ml of dichloromethane was slowly added to the reaction mixture. After stirring them overnight, the solvent was evaporated under reduced pressure and the residue was purified by the silica gel chromatography (hexane:ethyl acetate=9:1 to 7:3) to obtain the title compound.

Yield: 113 mg (0.197 mmol), 54% $^1$H-NMR (CDCl$_3$): 0.11 (6H, d), 0.90 (9H, s), 1.24 (9H, s), 2.10-2.20 (2H, m), 2.25-2.40 (2H, m), 3.30-3.12 (2H, m), 3.46 (1H, t), 3.50-3.61 (2H, m), 3.97 (1H, dd), 4.10-4.18 (1H, m), 5.57 (1H, d), 6.60 (1H, s), 6.91 (2H, s), 7.13-7.36 (8H, m).

Step 5

Synthesis of N-[2-(t-butylamino)-1-(hydroxymethyl)-2-oxoethyl]-4-(5H-dibenzo[a,d][7]annulen-5-ylidene)-1-piperidinecarboxamide:

113 mg (0.197 mmol) of N-[2-(t-butylamino)-1-({[t-butyl(dimethyl)silyl]oxy}methyl)-2-oxoethyl]-4-(5H-dibenzo[a,d] [7] annulen-5-ylidene)-1-piperidinecarboxamide was dissolved in 3 ml of tetrahydrofuran. 0.22 ml of 1 M tetrabutylammonium fluoride/tetrahydrofuran solution was added to the obtained solution, and they were stirred for 30 minutes. After the purification by the silica gel chromatography (hexane:ethyl acetate=9:1 to 3:2), the title compound was obtained.

Yield: 66.9 mg (0.146 mmol), 74% MS (ESI, m/z) 460(M+H)$^+$ $^1$H-NMR (CDCl$_3$): 1.35 (9H, s), 2.13-2.26 (2H, m), 2.28-2.42 (2H, m), 3.01-3.15 (2H, m), 3.50-3.64 (3H, m), 4.03-4.26 (2H, m), 5.64 (1H, d), 6.77 (1H, br s), 6.94 (2H, s), 7.16-7.40 (8H, m).

Referential Example 50

Synthesis of N-[3-[4-(5H-dibenzo[a,d] [7] annulen-5-ylidene)-1-piperidinyl]-1-(hydroxymethyl)-3-oxopropyl]-2,2-dimethylpropanamide:

Step 1

Synthesis of 3-[(t-butoxycarbonyl)amino]-4-methoxy-4-oxobutanoic Acid:

2.0 g (6.18 mmol) of 4-(benzyloxy)-2-[(t-butoxycarbonyl)amino]-4-oxobutanoic acid was dissolved in a solvent mixture of 6 ml of methanol and 12 ml of toluene. 3.7 ml of 2 M trimethylsilyldiazomethane/hexane solution was added to the obtained solution and they were stirred for 3 hours. Additional 0.5 ml of 2 M trimethylsilyldiazomethane/hexane solution was added to the reaction mixture and they were stirred for 1 hour. The solvent was evaporated under reduced pressure. The residue was dissolved in 20 ml of ethanol. 2.0 g of palladium carbon (10% w/v) was added to the obtained solution, and they were stirred in hydrogen gas atmosphere for 19 hours. After the filtration, the solvent was evaporated under reduced pressure to obtain the title compound.

Yield: 1.50 g (6.07 mmol), 98% $^1$H-NMR (DMSO-$d_6$): 1.38 (9H, s), 2.49-2.70 (2H, m), 3.62 (3H, s), 4.32 (1H, m), 7.23 (1H, d).

Step 2

Synthesis of methyl 2-[(t-butoxycarbonyl)amino]-4-[4-(5H-dibenzo[a,d][7]annulen-5-ylidene)-1-piperidinyl]-4-oxobutanoate:

1.10 g (4.04 mmol) of 4-(5H-dibenzo[a,d][7]annulen-5-ylidene)-1-piperidine, 1.00 g (4.04 mmol) of 3-[(t-butoxycarbonyl)amino]-4-methoxy-4-oxobutanoic acid, 930 mg (4.85 mmol) of 1-ethyl-3-(3'-dimethylaminopropyl)carbodiimide hydrochloride and 48.9 mg (0.40 mmol) of 4-dimethylaminopyridine were dissolved in 10 ml of dichloromethane. 532 mg (5.25 mmol) of triethylamine was added to the obtained solution, and they were stirred overnight. Saturated aqueous ammonium chloride solution was added to the reaction mixture. After extracting with ethyl acetate 3 times, the organic layer was washed with saturated sodium hydrogencarbonate solution and then dried over anhydrous sodium sulfate. The solvent was evaporated under reduced pressure, and the residue was purified by the silica gel chromatography (hexane:ethyl acetate=89:11) to obtain the title compound.

Yield: 1.17 g (2.32 mmol), 58% MS (ESI, m/z) 503 (M+H)$^+$ $^1$H-NMR (CDCl$_3$): 1.43 (9H, d), 2.10-2.38 (4H, m), 2.73 (1H, m), 2.90-3.18 (3H, m), 3.48-3.54 (1H, m), 3.73 (3H, d), 3.83-3.95 (1H, m), 4.49-4.58 (1H, m), 5.77 (1H, t), 6.91 (2H, s), 7.16-7.36 (8H, m).

Step 3

Synthesis of methyl 4-[4-(5H-dibenzo[a,d][7]annulen-5-ylidene)-1-piperidinyl]-2-[(2,2-dimethylpropanoyl)amino]-4-oxobutanoate:

600 mg (1.19 mmol) of methyl 2-[(t-butoxycarbonyl)amino]-4-[4-(5H-dibenzo [a, d] [7] annulen-5-ylidene)-1-piperidinyl]-4-oxobutanoate was dissolved in 5 ml of ethyl acetate. 0.5 ml of 4 N hydrochloric acid/ethyl acetate solution was added to the obtained solution, and they were stirred at 0° C. for 3 hours. After stirring at room temperature overnight, the solvent was evaporated under reduced pressure. The residue was dissolved in 10 ml of dichloromethane. 602 mg (5.95 mmol) of triethylamine and 158 mg (1.31 mmol) of pivaloyl chloride were added to the obtained solution, and they were stirred for 10 minutes. Saturated aqueous sodium hydrogencarbonate solution and water were added to the reaction mixture. After extracting with ethyl acetate 3 times followed by the drying over anhydrous sodium sulfate, the solvent was evaporated under reduced pressure, and the residue was purified by the silica gel chromatography (hexane:ethyl acetate=89:11 to 65:35) to obtain the title compound.

Yield: 468 mg (0.962 mmol), 81% MS (ESI, m/z) 487 (M+H)$^{+1}$H-NMR (CDCl$_3$): 1.20 (9H, d), 2.10-2.38 (4H, m), 2.60-2.81 (1H, m), 2.85-3.20 (3H, m), 3.42-3.57 (1H, m), 3.74 (3H, d), 3.80-3.98 (1H, m), 4.85 (1H, m), 6.92 (2H, s), 7.03 (1H, d), 7.11-7.38 (8H, m).

Step 4

Synthesis of N-[3-[4-(5H-dibenzo[a,d][7]annulen-5-ylidene)-1-piperidinyl]-1-(hydroxymethyl)-3-oxopropyl]-2,2-dimethylpropanamide:

106 mg (0.218 mmol) of methyl 4-[4-(5H-dibenzo[a,d][7]annulen-5-ylidene)-1-piperidinyl]-2-[(2,2-dimethylpropanoyl)amino]-4-oxobutanoate was dissolved in 3 ml of tetrahydrofuran. 5.7 mg (0.261 mmol) of lithium borohydride was added to the obtained solution at 0° C. The reaction mixture was stirred for 1.5 hours and then saturated aqueous ammonium chloride solution was added thereto. After extracting with ethyl acetate 3 times, the extract was dried over anhydrous sodium sulfate. The solvent was evaporated under reduced pressure to obtain the title compound.

Yield: 72.3 mg (0.158 mmol), 72% MS (ESI, m/z) 459 (M+H)$^{+1}$H-NMR (CDCl$_3$): 1.18 (9H, d), 2.11-2.35 (4H, m), 2.58-2.71 (2H, m), 2.88-3.21 (2H, m), 3.56-3.79 (3H, m), 3.85-4.15 (3H, m), 6.95-7.00 (3H, m), 7.11-7.33 (8H, m).

Referential Example 51

Synthesis of cyclohexyl 2-[4-(5H-dibenzo[a,d][7]annulen-5-ylidene)-1-piperidinyl]-2-oxoethylcarbamate:

Step 1

Synthesis of {[(cyclohexyloxy)carbonyl]amino}acetic acid:

620 mg (4.80 mmol) of ethyl isocyanatoacetate was dissolved in 5 ml of dichloromethane. 10 ml of a solution of 0.56 ml (5.28 mmol) of cyclohexanol in dichloromethane was added to the obtained solution under cooling with ice, and they were stirred at room temperature for 15 minutes. The reaction mixture was concentrated under reduced pressure. 5.8 ml of 1 N aqueous lithium hydroxide solution was added to the concentrate, and the obtained mixture was stirred in a solvent mixture of methanol: water=2:1 at room temperature for 2 hours. The reaction mixture was concentrated under reduced pressure. Water was added to the concentrate and the resultant aqueous layer was washed with ethyl acetate. 0.1 N aqueous hydrochloric acid solution was added to the aqueous layer to control pH at 2 to 3. After extracting with ethyl acetate, the organic layer was dried over anhydrous magnesium sulfate and then concentrated under reduced pressure to obtain the title compound.

Yield: 86.1 mg (0.428 mmol), 8.9% MS (ESI, m/z) 200 (M−H)$^{−1}$H-NMR (CDCl$_3$): 1.22-1.56 (6H, m), 1.65-1.76 (2H, m), 1.80-1.92 (2H, m), 3.95-4.02 (2H, m), 4.65 (1H, br s), 5.15 (1H, br s).

Step 2

Synthesis of cyclohexyl 2-[4-(5H-dibenzo[a,d][7]annulen-5-ylidene)-1-piperidinyl]-2-oxoethylcarbamate:

86.1 mg (0.428 mmol) of {[(cyclohexyloxy)carbonyl]amino}acetic acid, 176 mg (0.642 mmol) of 4-(5H-dibenzo[a,d][7]annulen-5-ylidene)piperidine and 98.5 mg (0.514 mmol) of 1-ethyl-3-(3'-dimethylaminopropyl)carbodiimide hydrochloride were suspended in 10 ml of dichloromethane. 0.086 ml (0.617 mmol) of triethylamine was added to the obtained suspension, and they were stirred at room temperature for 3 hours. The resultant mixture was concentrated under reduced pressure and then ethyl acetate was added to the residue. The resultant mixture was washed with saturated aqueous sodium hydrogencarbonate solution, dried over anhydrous magnesium sulfate and then concentrated under reduced pressure. The obtained residue was purified by the silica gel chromatography (hexane:ethyl acetate=95:5 to 1:4) to obtain the title compound.

Yield: 82.9 mg (0.182 mmol), 43% MS (ESI, m/z) 457 $(M+H)^{+1}$H-NMR (CDCl$_3$): 1.32-1.42 (4H, m), 1.45-1.57 (3H, m), 1.64-1.75 (2H, m), 1.80-1.90 (2H, m), 2.15-2.34 (4H, m), 2.99-3.08 (2H, m), 3.41-3.47 (1H, m), 3.88-3.99 (2H, m), 4.58-4.67 (1H, m), 5.62 (1H, br s), 6.92 (2H, s), 7.15-7.18 (2H, m), 7.23-7.24 (1H, m), 7.28-7.29 (1H, m), 7.32-7.37 (4H, m).

Referential Example 52

Synthesis of 1-methylcyclopentyl 2-[4-(5H-dibenzo[a,d][7] annulen-5-ylidene)-1-piperidinyl]-2-oxoethylcarbamate:

Step 1

Synthesis of ({[(1-methylcyclopentyl)oxy]carbonyl}amino) acetic Acid:

500 mg (3.87 mmol) of ethyl isocyanatoacetate was dissolved in 5 ml of dichloromethane. 0.05 ml of 4 N hydrochloric acid/1,4-dioxane solution was added to the obtained solution. 465 mg (4.64 mmol) of 1-methylcyclopentanol was added to the resultant mixture, and they were stirred for 3 hours 30 minutes. 10 ml of methanol and 12 ml of 1 N aqueous sodium hydroxide solution were added thereto and they were stirred for 15 minutes. The organic solvent was evaporated under reduced pressure. After extracting with dichloromethane twice, the aqueous layer was neutralized with 1 N aqueous hydrochloric acid solution. The product was extracted with dichloromethane 3 times and then dried over anhydrous sodium sulfate. The solvent was evaporated under reduced pressure to obtain the title compound. The product was subjected to the next reaction without any purification.

Yield: 43.0 mg (0.214 mmol), 5.5% $^1$H-NMR (CDCl$_3$): (Only the main peaks are shown because the product contained impurities) 1.56 (3H, s), 5.22 (1H, d).

Step 2

Synthesis of 1-methylcyclopentyl 2-[4-(5H-dibenzo[a,d][7] annulen-5-ylidene)-1-piperidinyl]-2-oxoethylcarbamate:

70.2 mg (0.257 mmol) of 4-(5H-dibenzo[a,d][7]annulen-5-ylidene)-1-piperidine, 43.0 mg (0.214 mmol) of ({[(1-methylcyclopentyl)oxy]carbonyl}amino)acetic acid, 49.3 mg (0.257 mmol) of 1-ethyl-3-(3'-dimethylaminopropyl)carbodiimide hydrochloride and 3.6 mg (0.03 mmol) of 4-dimethylaminopyridine were dissolved in 1 ml of dichloromethane. 26.0 mg (0.257 mmol) of triethylamine was added to the obtained solution, and they were stirred overnight. After the purification by the silica gel chromatography (hexane:ethyl acetate=9:1 to 3:2), the title compound was obtained.

Yield: 56.7 mg (0.124 mmol), 58% MS (ESI, m/z) 457 $(M+H)^{+1}$H-NMR (CDCl$_3$): 1.48-1.76 (9H, m), 2.00-2.36 (6H, m), 3.02 (2H, m), 3.37-3.50 (1H, m), 3.80-4.05 (3H, m), 5.53 (1H, s), 6.92 (2H, s), 7.13-7.20 (2H, m), 7.22-7.37 (6H, m).

Referential Example 53

Synthesis of tetrahydro-2H-pyran-4-yl 2-[4-(5H-dibenzo[a, d] [7]annulen-5-ylidene)-1-piperidinyl]-2-oxoethylcarbamate:

Step 1

Synthesis of ethyl {[(tetrahydro-2H-pyran-4-yloxy)carbonyl]amino}acetate:

0.600 ml (4.80 mmol) of ethyl isocyanatoacetate was dissolved in dichloromethane. 0.06 ml of 4 N hydrochloric acid/1,4-dioxane solution was added to the obtained solution, and they were stirred at room temperature for 5 minutes. 0.503 ml (5.28 mmol) of tetrahydro-4H-4-pyranol was added to the reaction mixture, and they were stirred at room temperature overnight. After concentrating the reaction mixture under reduced pressure, the residue was purified by the silica gel chromatography (hexane:ethyl acetate=9:1 to 1:4), the title compound was obtained.

Yield: 584 mg (2.53 mmol), 53% $^1$H-NMR (CDCl$_3$): 1.29 (3H, t), 1.61-1.73 (2H, m), 1.89-1.97 (2H, m), 3.49-3.56 (2H, m), 3.87-3.96 (4H, m), 4.22 (2H, q), 4.81-4.90 (1H, m), 5.13-5.20 (1H, br s).

Step 2

Synthesis of {[(tetrahydro-2H-pyran-4-yloxy)carbonyl] amino}acetic acid:

The title compound was obtained from 287 mg (1.24 mmol) of ethyl {[(tetrahydro-2H-pyran-4-yloxy)carbonyl] amino}acetate and 1.49 ml of 1 N aqueous lithium hydroxide solution in the same manner as that in Step 2 in Referential Example 43.

Yield: 269 mg (1.32 mmol), 100% MS (ESI, m/z) 202 $(M-H)^{-1}$H-NMR (DMSO-d$_6$): 1.40-1.52 (2H, m), 1.77-1.83 (2H, m), 3.28-3.43 (4H, m), 3.73-3.80 (2H, m), 4.63 (1H, sept), 6.31 (1H, br s).

Step 3

Synthesis of tetrahydro-2H-pyran-4-yl 2-[4-(5H-dibenzo[a, d][7]annulen-5-ylidene)-1-piperidinyl]-2-oxoethylcarbamate:

{[(Tetrahydro-2H-pyran-4-yloxy)carbonyl]amino}acetic acid, 563 mg (2.06 mmol) of 4-(5H-dibenzo[a,d][7]annulen-5-ylidene)piperidine and 563 mg (1.65 mmol) of 1-ethyl-3-(3'-dimethylaminopropyl)carbodiimide hydrochloride were suspended in 10 ml of dichloromethane. 0.23 ml (1.65 mmol) of triethylamine was added to the obtained suspension, and they were stirred at room temperature overnight. 20 ml of dimethylformamide was added to the reaction mixture, and they were stirred at 50° C. for 3 hours. 263 mg (1.37 mmol) of 1-ethyl-3-(3'-dimethylaminopropyl)carbodiimide hydrochloride, 50 mg (0.41 mmol) of 4-dimethylaminopyridine and 0.19 ml (1.37 mmol) of triethylamine were added to the reaction mixture, and they were stirred at 50° C. overnight. The resultant mixture was concentrated under reduced pressure and then ethyl acetate was added to the residue. The resultant mixture was washed with saturated aqueous sodium hydrogencarbonate solution and saturated aqueous sodium chloride solution. The organic layer was dried over anhydrous magnesium sulfate and then concentrated under reduced pressure. The obtained residue was purified by the silica gel chromatography (hexane:ethyl acetate=3:1 to 1:2) to obtain the title compound.

Yield: 32.1 mg (0.0700 mmol), 5.1% MS (ESI, m/z) 459 $(M+H)^{+1}$H-NMR (CDCl$_3$): 1.62-1.72 (2H, m), 1.87-1.96 (2H, m), 2.15-2.33 (4H, m), 2.99-3.08 (2H, m), 3.42-3.56

(3H, m), 3.86-4.13 (5H, m), 4.81-4.86 (1H, m), 5.70 (1H, br t), 6.92 (2H, s), 7.15-7.18 (2H, m), 7.23-7.29 (2H, m), 7.32-7.37 (4H, m).

Referential Example 54

Synthesis of methyl 4-[4-(5H-dibenzo[a,d][7]annulen-5-ylidene)-1-piperidinyl]-2-[(2,2-dimethylpropanoyl)amino]-4-oxobutanoate:

The compound synthesized in Step 3 in Referential Example 50.

Referential Example 55

Synthesis of methyl 2-[(t-butoxycarbonyl)amino]-4-[4-(5H-dibenzo[a,d][7]-annulen-5-ylidene)-1-piperidinyl]-4-oxobutanoate:

The compound synthesized in Step 2 in Referential Example 50.

Referential Example 56

Synthesis of 2-[(t-butoxycarbonyl)amino]-4-[4-(5H-dibenzo[a,d][7]annulen-5-ylidene)-1-piperidinyl]-4-oxobutanoic Acid:

150 mg (0.298 mmol) of the compound of Referential Example 55 was dissolved in 2 ml of a solvent mixture of methanol: tetrahydrofuran=1:1.

0.36 ml of 1 N aqueous lithium hydroxide solution was added to the obtained solution at room temperature. After stirring for 3.5 hours, the solvent was evaporated under reduced pressure. Saturated aqueous sodium hydrogencarbonate solution was added to the residue, and the obtained mixture was washed with diethyl ether. The aqueous layer was adjusted to pH 4 with 1 N hydrochloric acid. After extracting with ethyl acetate, the organic layer was dried over anhydrous magnesium sulfate. The solvent was evaporated under reduced pressure to obtain the title compound.

Yield: 150 mg (0.307 mmol), quantitative. MS (ESI, m/z) 172 (M+H)$^+$ $^1$H-NMR (CDCl$_3$): 1.43 (9H, d), 2.16-2.44 (4H, m), 2.58-2.71 (1H, m), 2.93-3.24 (3H, m), 3.52-3.58 (1H, m), 3.91-4.04 (1H, m), 4.46-4.54 (1H, m), 5.78 (1H, br d), 6.92 (2H, d), 7.14-7.19 (2H, m), 7.23-7.29 (2H, m), 7.30-7.37 (4H, m).

Referential Example 57

Synthesis of 4-[4-(5H-dibenzo[a,d][7]annulen-5-ylidene)-1-piperidinyl]-2-[(2,2-dimethylpropanoyl)amino]-4-oxobutanoic Acid:

The title compound was obtained from the compound synthesized in Referential Example 54 in the same manner as that of Referential Example 56.

Yield: 133 mg (0.281 mmol), quantitative. MS (ESI, m/z) 471 (M−H)$^-$ $^1$H-NMR (CDCl$_3$): 1.20 (9H, d), 2.21-2.34 (3H, m), 2.42-2.61 (2H, m), 2.98-3.30 (3H, m), 3.54-3.63 (1H, m), 3.97-4.13 (1H, m), 4.59-4.67 (1H, m), 6.92 (2H, d), 7.07 (1H, br d), 7.13-7.19 (2H, m), 7.23-7.30 (2H, m), 7.32-7.37 (4H, m).

Referential Example 58

Synthesis of (S)-N-[3-[4-(5H-dibenzo[a,d][7]annulen-5-ylidene)-1-piperidinyl]-1-(hydroxymethyl)-3-oxopropyl]-2,2-dimethylpropanamide:

The title compound was obtained from (S)-4-(benzyloxy)-2-[(t-butoxycarbonyl)amino]-4-oxobutanoic acid in the same manner as that of Referential Example 50.

MS (ESI, m/z) 459 (M+H)$^+$ $^1$H-NMR (CDCl$_3$): 1.18 (9H, d), 2.11-2.37 (4H, m), 2.57-2.82 (2H, m), 2.89-3.22 (2H, m), 3.58-3.80 (3H, m), 3.87-4.13 (3H, m), 6.92 (2H, s), 6.89-6.99 (1H, m), 7.13-7.20 (2H, m), 7.23-7.38 (6H, m).

Referential Example 59

Synthesis of (R)-N-[3-[4-(5H-dibenzo[a,d][7]annulen-5-ylidene)-1-piperidinyl]-1-(hydroxymethyl)-3-oxopropyl]-2,2-dimethylpropanamide:

The title compound was obtained from (R)-4-(benzyloxy)-2-[(t-butoxycarbonyl)amino]-4-oxobutanoic acid in the same manner as that in Referential Example 50.

MS (ESI, m/z) 459 (M+H)$^+$ $^1$H-NMR (CDCl$_3$): 1.18 (9H, d), 2.12-2.37 (4H, m), 2.59-2.82 (2H, m), 2.91-3.22 (2H, m), 3.57-3.82 (3H, m), 3.86-4.13 (3H, m), 6.92 (2H, s), 6.89-6.97 (1H, m), 7.14-7.19 (2H, m), 7.22-7.37 (6H, m).

Referential Example 60

Synthesis of t-butyl 3-[4-(5H-dibenzo[a,d][7]annulen-5-ylidene)-1-piperidinyl]-1-(hydroxymethyl)-3-oxopropylcarbamate:

The title compound was obtained from the compound in step 2 in Referential Example 50 in the same manner as that in Step 4 in Referential Example 50.

Yield: 56.3 mg (0.119 mmol), 55% MS (ESI, m/z) 475 (M+H)$^+$ $^1$H-NMR (CDCl$_3$): 1.42 (9H, d), 2.16-2.35 (4H, m), 2.62-2.80 (2H, m), 2.93-3.02 (1H, m), 3.07-3.16 (1H, m), 3.58-3.75 (4H, m), 3.88-3.98 (2H, m), 5.49 (1H, br s), 6.92 (2H, s), 7.14-7.19 (2H, m), 7.23-7.28 (2H, m), 7.31-7.37 (4H, m).

Referential Example 61

Synthesis of t-butyl 3-[4-(5H-dibenzo[a,d][7]annulen-5-yl)-1-piperazinyl]-3-oxopropylcarbamate:

Step 1

Synthesis of 5H-dibenzo[a,d][7]annulen-5-ol:

4 ml of water, 0.45 ml of 1 N aqueous sodium hydroxide solution and 20 ml of a suspension of 1.50 g (7.27 mmol) of dibenzosuberenone in methanol were added to 200 mg (5.29 mmol) of sodium borohydride, and they were stirred overnight. Crystals thus precipitated were taken by the filtration, washed with water and dissolved in ethyl acetate. After drying over anhydrous magnesium sulfate, the solvent was evaporated under reduced pressure to obtain the title compound.

Yield: 1.48 g (7.11 mmol), 98% $^1$H-NMR (CDCl$_3$): 2.41 (1H, d), 5.43 (1H, d), 7.11 (2H, s), 7.25-7.31 (2H, m), 7.36-7.44 (4H, m), 7.66 (2H, d).

Step 2

Synthesis of t-butyl 4-(5H-dibenzo[a,d][7]annulen-5-yl)-1-piperazinecarboxylate:

750 mg (3.60 mmol) of the compound obtained in step 1 described above was dissolved in 8 ml of benzene. 0.02 ml of pyridine was added to the obtained solution, and 3.5 ml (48.2 mmol) of thionyl chloride was added to the obtained mixture under cooling with ice. After stirring the reaction mixture at 0° C. for 1 hour and then at room temperature for 2 hours, the solvent was evaporated under reduced pressure. 10 ml of tetrahydrofuran was added to the residue. 2.5 ml (18 mmol) of triethylamine and 805 mg (4.32 mmol) of t-butyl piperazinecarboxylate were added to reaction mixture under cooling with ice. The temperature of the mixture was slowly elevated to room temperature, and it was stirred overnight. The solvent was evaporated under reduced pressure. Dichloromethane was added to the residue. After washing with water and saturated aqueous sodium chloride solution, the organic layer was dried over anhydrous magnesium sulfate. The solvent was evaporated under reduce pressure, and the residue was purified by the basic silica gel chromatography (hexane: dichloromethane=9:1) to obtain the title compound.

Yield: 1.25 g (3.31 mmol), 92% MS (ESI, m/z) 377 (M+H)$^{+1}$H-NMR (CDCl$_3$): 1.39 (9H, s), 1.92 (4H, br t), 3.13 (4H, br t), 4.26 (1H, s), 6.96 (2H, s), 7.27-7.39 (8H, m).

Step 3

Synthesis of t-butyl 3-[4-(5H-dibenzo[a,d][7]annulen-5-yl)-1-piperazinyl]-3-oxopropylcarbamate:

300 mg (0.797 mmol) of the compound obtained in the above-described step 2 was dissolved in 5 ml of 1,4-dioxane. 1 ml of 4 N hydrochloric acid/1,4-dioxane was added to the obtained solution under cooling with ice, and they were stirred at room temperature for 7.5 hours. The solvent was evaporated under reduced pressure. Ethyl acetate was added to the residue. After washing with 1 N aqueous sodium hydroxide solution, the organic layer was dried over anhydrous sodium sulfate. The solvent was evaporated under reduced pressure. 175 mg (0.925 mmol) of 3-[(t-butoxycarbonyl)amino]propanoic acid and 191 mg (0.925 mmol) of 1-ethyl-3-(3'-dimethylaminopropyl)carbodiimide hydrochloride were added to the residue, and the resultant mixture was dissolved in 15 ml of dichloromethane. Then 0.13 ml (0.925 mmol) of triethylamine and 10 mg (0.08 mmol) of dimethylaminopyridine were added to the obtained solution, and they were stirred at room temperature overnight. The solvent was evaporated under reduced pressure. Ethyl acetate was added to the residue. After washing with saturated aqueous sodium hydrogencarbonate solution and saturated aqueous sodium chloride solution, the organic layer was dried over anhydrous magnesium sulfate. The solvent was evaporated under reduced pressure. The residue was purified by the silica gel chromatography (hexane:ethyl acetate=19:1 to 1:4) to obtain the title compound.

Yield: 181 mg (0.404 mmol), 52% MS (ESI, m/z) 448 (M+H)$^{+1}$H-NMR (CDCl$_3$): 1.41 (9H, s), 1.95 (4H, br t), 2.38 (2H, br t), 3.13 (2H, br t), 3.30-3.38 (4H, m), 4.27 (1H, s), 5.26 (1H, br s), 6.96 (2H, s), 7.28-7.40 (8H, m).

Referential Example 62

Synthesis of (S)-N-{2-amino-3-[4-(5H-dibenzo[a,d][7]annulen-5-ylidene)-1-piperidinyl]-3-oxopropyl}-2,2-dimethylpropanamide Hydrochloride:

Step 1

Synthesis of t-butyl (S)-2-[4-(5H-dibenzo[a,d] [7]annulen-5-ylidene)-1-piperidinyl]-1-{[(2,2-dimethylpropanoyl) amino]methyl}-2-oxoethylcarbamate:

1.70 g (8.09 mmol) of (S)-3-amino-2-[(t-butoxycarbonyl)amino]propanoic acid 0.3 hydrate was dissolved in 40 ml of dichloromethane. 2.74 ml (19.6 mmol) of triethylamine and 1.20 ml (9.71 mmol) of pivaloyl chloride were added to the obtained solution under cooling with ice, and they were stirred for 4 hours while the temperature was elevated to room temperature. An aqueous ammonium chloride solution was added to the reaction mixture under cooling with ice, and the solvent was evaporated under reduced pressure. Ethyl acetate was added to the residue. After washing with 0.1 N hydrochloric acid, the organic layer was dried over anhydrous magnesium sulfate and then the solvent was evaporated under reduced pressure. 2.03 g (10.6 mmol) of 1-ethyl-3-(3'-dimethylaminopropyl)carbodiimide hydrochloride was added to the residue, and the resultant mixture was dissolved in 70 ml of dichloromethane. 1.48 ml (10.6 mmol) of triethylamine, 2.00 g (7.33 mmol) of 4-(5H-dibenzo[a,d][7]annulen-5-ylidene)-1-piperidine and 86 mg (0.7 mmol) of dimethylaminopyridine were added to the obtained solution under cooling with ice, and they were stirred at room temperature overnight. The solvent was evaporated under reduced pressure, and ethyl acetate was added to the residue. After washing with saturated sodium hydrogencarbonate solution, the organic layer was dried over anhydrous magnesium sulfate. The solvent was evaporated under reduced pressure, and the residue was purified by the silica gel chromatography (hexane:ethyl acetate=9:1 to 1:3) to obtain the title compound.

Yield: 1.40 g (2.57 mmol), 32% MS (ESI, m/z) 544 (M+H)$^{+1}$H-NMR (CDCl$_3$): 1.17 (9H, d), 1.42 (9H, d), 2.15-2.46 (4H, m), 2.90-3.25 (3H, m), 3.52-4.00 (3H, m), 4.68-4.78 (1H, m), 5.72 (1H, br t), 6.38 (1H, br d), 6.91 (2H, s), 7.13-7.19 (2H, m), 7.23-7.28 (2H, m), 7.32-7.37 (4H, m).

Step 2

Synthesis of (S)-N-{2-amino-3-[4-(5H-dibenzo[a,d][7]annulen-5-ylidene)-1-piperidinyl]-3-oxopropyl}-2,2-dimethylpropanamide hydrochloride:

1.40 g (2.57 mmol) of the compound obtained in step 1 described above was dissolved in 12 ml of ethyl acetate. 10 ml of 4 N hydrochloric acid/ethyl acetate was added to the obtained solution under cooling with ice. The temperature was gradually elevated to room temperature. After stirring for 3.5 hours, the solvent was evaporated under reduced pressure to obtain the title compound.

Yield: 1.08 g (2.26 mmol), 88% MS (ESI, m/z) 444 (M+H)$^{+1}$H-NMR (CDCl$_3$): 1.14 (9H, d), 2.04-2.46 (4H, m), 2.81-3.02 (1H, m), 3.20-3.43 (2H, m), 3.58-3.89 (3H, m), 4.41 (1H, br s), 6.88 (2H, d), 7.07-7.16 (2H, m), 7.22-7.34 (6H, m), 7.70 (1H, br s), 8.42 (2H, br s).

Referential Example 63

Synthesis of (R)-N-{2-amino-3-[4-(5H-dibenzo[a,d][7]annulen-5-ylidene)-1-piperidinyl]-3-oxopropyl}-2,2-dimethylpropanamide Hydrochloride:

The title compound was obtained in the same manner as that in Referential Example 62.

MS (ESI, m/z) 444 (M+H)$^{+1}$H-NMR (CDCl$_3$): 1.14 (9H, d), 1.82-2.50 (4H, m), 2.80-3.04 (1H, m), 3.16-3.94 (5H, m), 4.41 (1H, br s), 6.88 (2H, d), 7.05-7.17 (2H, m), 7.21-7.36 (6H, m), 7.72 (1H, br s), 8.40 (2H, br s).

Referential Example 64

Synthesis of N-[3-[4-(5H-dibenzo[a,d] [7] annulen-5-yl)-1-piperazinyl]-1-(hydroxymethyl)-3-oxopropyl]-2,2-dimethylpropanamide Hydrochloride:

Step 1

Synthesis of methyl 2-[(t-butoxycarbonyl)amino]-4-[4-(5H-dibenzo[a,d][7]annulen-5-yl)-1-piperazinyl]-4-oxobutanoate:

442 mg (1.17 mmol) of the compound obtained in Step 2 in Referential Example 61 was dissolved in 10 ml of 1,4-dioxane. 1.5 ml of 4 N hydrochloric acid/1,4-dioxane was added to the obtained solution under cooling with ice, and they were stirred at room temperature overnight. 0.1 ml of 4 N hydrochloric acid/1,4-dioxane was added to the resultant mixture under cooling with ice, and they were stirred at room temperature for 3 hours. The solvent was evaporated under reduced pressure. Ethyl acetate was added to the residue. After washing with 1 N aqueous sodium hydroxide solution, the organic layer was dried over anhydrous sodium sulfate and then the solvent was evaporated under reduced pressure. 347 mg (1.40 mmol) of 3-[(t-butoxycarbonyl)amino]-4-methoxy-4-butanoic acid and 314 mg (1.64 mmol) of 1-ethyl-3-(3'-dimethylaminopropyl)carbodiimide hydrochloride were added to the residue, and the resultant mixture was dissolved in 10 ml of dichloromethane. 0.20 ml (1.64 mmol) of triethylamine and 17 mg (0.12 mmol) of dimethylaminopyridine were added to the obtained solution, and they were stirred at room temperature overnight. The solvent was evaporated under reduced pressure, and ethyl acetate was added to the residue. After washing with saturated sodium hydrogencarbonate solution, the organic layer was dried over anhydrous magnesium sulfate. The solvent was evaporated under reduced pressure, and the residue was purified by the silica gel column chromatography (hexane:ethyl acetate=100:1 to 65:35) to obtain the title compound.

Yield: 524 mg (1.04 mmol), 89% MS (ESI, m/z) 506 (M+H)$^{+1}$H-NMR (CDCl$_3$): 1.43 (9H, s), 1.93-1.98 (4H, m), 2.64 (1H, dd), 3.00 (1H, dd), 3.12 (2H, br t), 3.28 (2H, br t), 3.71 (3H, s), 4.27 (1H, s), 4.50 (1H, dt), 5.73 (1H, d), 6.95 (2H, s), 7.27-7.40 (8H, m).

Step 2

Synthesis of methyl 4-[4-(5H-dibenzo[a,d][7]annulen-5-yl)-1-piperazinyl]-2-[(2,2-dimethylpropanoyl)amino]-4-oxobutanoate:

The title compound was obtained from 522 mg (1.32 mmol) of the compound obtained in step 1 described above in the same manner as that in Step 3 in Referential Example 50.

Yield: 406 mg (0.829 mmol), 63% MS (ESI, m/z) 490 (M+H)$^{+1}$H-NMR (CDCl3): 1.19 (9H, s), 1.92-1.99 (4H, m), 2.62 (1H, dd), 3.02 (1H, dd), 3.13 (2H, br t), 3.28 (2H, br t), 3.71 (3H, s), 4.27 (1H, s), 4.80 (1H, dt), 6.95 (2H, s), 6.99 (1H, br d), 7.28-7.40 (8H, m).

Step 3

Synthesis of N-[3-[4-(5H-dibenzo[a,d][7]annulen-5-yl)-1-piperazinyl]-1-(hydroxymethyl)-3-oxopropyl]-2,2-dimethylpropanamide hydrochloride:

The title compound was obtained from 405 mg (0.827 mmol) of the compound obtained in step 2 described above by the same method as that in Step 4 in Referential Example 50 and then converting the product into its hydrochloride.

Yield: 307 mg (0.665 mmol), 81% MS (ESI, m/z) 462 (M+H)$^{+1}$H-NMR (CDCl$_3$): 1.16 (9H, s), 1.93-2.00 (4H, m), 2.61 (2H, qd), 3.23-3.40 (4H, m), 3.58-3.74 (2H, m), 3.93-4.03 (2H, m), 4.27 (1H, s), 6.88 (1H, dd), 6.95 (2H, s), 7.28-7.40 (8H, m). (free)

Referential Example 65

Synthesis of (R)-N-{2-[4-(5H-dibenzo[a, d] [7]annulen-5-ylidene)-1-piperidinyl]-2-oxoethyl}-2-pyrrolidinecarboxamide hydrochloride:

Step 1

Synthesis of t-butyl 2-[({2-[4-(5H-dibenzo[a,d][7]annulen-5-ylidene)-1-piperidinyl]-2-oxoethyl}amino)carbonyl]-1-pyrrolidinecarboxylate:

700 mg (1.91 mmol) of the compound of Referential Example 2, 493 mg (2.29 mmol) of (R)-1-(t-butoxycarbonyl)-2-pyrrolidinecarboxylic acid and 512 mg (2.67 mmol) of 1-ethyl-3-(3'-dimethylaminopropyl)carbodiimide hydrochloride were dissolved in 20 ml of dichloromethane. 0.77 ml (5.59 mmol) of triethylamine and 24 mg (0.2 mmol) of dimethylaminopyridine were added to the obtained solution under cooling with ice, and they were stirred at room temperature overnight. The solvent was evaporated under reduced pressure. Ethyl acetate was added to the residue, and they were washed with water. The organic layer was dried over anhydrous magnesium sulfate. The solvent was evaporated under reduced pressure, and the residue was purified by the silica gel chromatography (hexane:ethyl acetate=9:1 to 1:4) to obtain the title compound.

Yield: 856 mg (1.62 mmol), 85% MS (ESI, m/z) 528 (M+H)$^{+1}$H-NMR (CDCl$_3$): 1.45 (9H, br s), 1.57-1.92 (3H, m), 2.04-2.33 (6H, m), 2.97-3.09 (2H, m), 3.14-3.54 (3H, m), 3.89-4.36 (4H, m), 6.92 (2H, s), 7.15-7.18 (2H, m), 7.24-7.29 (3H, m), 7.32-7.37 (3H, m).

Step 2

Synthesis of (R)-N-{2-[4-(5H-dibenzo [a, d][7]annulen-5-ylidene)-1-piperidinyl]-2-oxoethyl}-2-pyrrolidinecarboxamide hydrochloride:

854 mg (1.62 mmol) of the compound obtained in step 1 described above was dissolved in 20 ml of 1,4-dioxane. 2 ml of 4 N hydrochloric acid/1,4-dioxane was added to the obtained solution under cooling with ice, and they were stirred at room temperature for 2.5 hours. The reaction mixture was cooled with ice, 5 ml of 4 N hydrochloric acid/1,4-dioxane was added thereto, and they were stirred at room temperature for 2 hours. 2.5 ml of 4 N hydrochloric acid/1,4-dioxane was added to the reaction mixture under cooling with ice. After stirring at room temperature for 1 hour, 7.5 ml of 4 N hydrochloric acid/1,4-dioxane was added to the reaction mixture, and they were stirred at room temperature for 2 hours. The solvent was concentrated under reduced pressure. Diethyl ether was added to the residue, and crystals thus formed were taken by the filtration to obtain the title compound.

Yield: 747 mg (1.61 mmol) 99% MS (ESI, m/z) 428 (M+H)$^{+1}$H-NMR (CDCl3): 2.05 (4H, m), 2.18-2.27 (4H, m), 2.48 (1H, m), 3.04 (2H, m), 3.30-3.52 (3H, m), 3.81-3.95 (2H, m), 4.29 (1H, brd), 4.72 (1H, brd), 6.91 (2H, d), 7.15-7.18 (2H, m), 7.23-7.28 (2H, m), 7.32-7.34 (4H, m), 8.60 (1H, d).

Referential Example 66

Synthesis of (S)-N-{2-[4-(5H-dibenzo[a,d] [7] annulen-5-ylidene)-1-piperidinyl]-2-oxoethyl}-2-pyrrolidinecarboxamide hydrochloride:

The title compound was obtained from (S)-1-(t-butoxycarbonyl)-2-pyrrolidinecarboxylic acid in the same manner as that in Referential Example 65.

MS (ESI, m/z) 428 (M+H)$^{+1}$H-NMR (CDCl$_3$): 1.78-2.32 (8H, m), 2.33-2.51 (1H, m), 2.88-3.15 (2H, m), 3.28-3.55 (3H, m), 3.78-3.98 (2H, m), 4.36 (1H, dt), 4.70 (1H, brd), 6.91 (2H, d), 7.13-7.19 (2H, m), 7.22-7.37 (6H, m), 8.76 (1H, d).

Referential Example 67

Synthesis of (S)-t-butyl 3-[4-(5H-dibenzo[a,d] [7]annulen-5-ylidene)-1-piperidinyl]-1-(hydroxymethyl)-3-oxopropylcarbamate:

The title compound was obtained from (S)-4-(benzyloxy)-2-[(t-butoxycarbonyl)amino]-4-oxobutanoic acid in the same manner as that in Referential Example 60.

MS (ESI, m/z) 475 (M+H)$^{+1}$H-NMR (CDCl$_3$): 1.42 (9H, d), 2.15-2.38 (4H, m), 2.60-2.83 (2H, m), 2.93-3.04 (1H, m), 3.06-3.18 (1H, m), 3.53-3.82 (4H, m), 3.83-4.02 (2H, m), 5.50 (1H, br s), 6.92 (2H, s), 7.14-7.20 (2H, m), 7.23-7.38 (6H, m).

Referential Example 68

Synthesis of (R)-t-butyl 3-[4-(5H-dibenzo[a,d][7]annulen-5-ylidene)-1-piperidinyl]-1-(hydroxymethyl)-3-oxopropylcarbamate:

The title compound was obtained from (R)-4-(benzyloxy)-2-[(t-butoxycarbonyl)amino]-4-oxobutanoic acid in the same manner as that in Referential Example 60.

MS (ESI, m/z) 475 (M+H)$^{+1}$H-NMR (CDCl$_3$): 1.42 (9H, d), 2.14-2.35 (4H, m), 2.62-2.80 (2H, m), 2.93-3.01 (1H, m), 3.09-3.16 (1H, m), 3.58-3.79 (4H, m), 3.86-3.99 (2H, m), 5.50 (1H, br s), 6.92 (2H, s), 7.14-7.19 (2H, m), 7.23-7.28 (2H, m), 7.31-7.37 (4H, m).

Referential Example 69

Synthesis of (R)-N-[3-[4-(10,11-dihydro-5H-dibenzo[a,d][7]annulen-5-ylidene)-1-piperidinyl]-1-(hydroxymethyl)-3-oxopropyl]-2,2-dimethylpropanamide:

745 mg (1.48 mmol) of methyl (R)-2-[(t-butoxycarbonyl)amino]-4-[4-(5H-dibenzo[a,d] [7]annulen-5-ylidene)-1-piperidinyl]-4-oxobutanoate was dissolved in 70 ml of ethanol. 1.49 g of palladium carbon (10% w/v) was added to the obtained solution, and they were stirred at room temperature in hydrogen gas atmosphere under 4.4 atm. for 3.5 hours. The catalyst was filtered out, and the filtrate was concentrated under reduced pressure. The intended product was obtained from the resultant residue in the same manner as that in steps 3 and 4 in Referential Example 50.

Yield: 567 mg (1.23 mmol), 83% MS (ESI, m/z) 461 (M+H)$^{+1}$H-NMR (CDCl$_3$): 1.19 (9H, d), 2.29-2.50 (4H, m), 2.65-2.90 (4H, m), 3.03-3.42 (4H, m), 3.68-3.80 (3H, m), 3.72-4.15 (3H, m), 6.95-6.99 (1H, m), 7.01-7.05 (2H, m), 7.08-7.19 (6H, m).

Referential Example 70

Synthesis of (S)-N-[3-[4-(10,11-dihydro-5H-dibenzo[a,d][7] annulen-5-ylidene)-1-piperidinyl]-1-(hydroxymethyl)-3-oxopropyl]-2,2-dimethylpropanamide:

The title compound was obtained in the same manner as that in Referential Example 69.

MS (ESI, m/z) 461 (M+H)$^{+1}$H-NMR (CDCl$_3$): 1.19 (9H, d), 2.28-2.51 (4H, m), 2.63-2.90 (4H, m), 3.02-3.44 (4H, m), 3.64-3.83 (3H, m), 3.95-4.17 (3H, m), 6.94-7.07 (3H, m), 7.08-7.20 (6H, m).

Referential Example 71

Synthesis of (S)-N-[4-[4-(5H-dibenzo[a,d] [7]annulen-5-ylidene)-1-piperidinyl]-1-(hydroxylmethyl)-4-oxobutyl]-2,2-dimethylpropanamide:

Step 1

Synthesis of (S)-4-[(t-butoxycarbonyl)amino]-5-methoxy-5-oxopentanoic Acid:

The title compound was obtained from (S)-5-(benzyloxy)-2-[(t-butoxycarbonyl)amino]-5-oxopentanoic acid in the same manner as that in Step 1 in Referential Example 50.

Yield: 7.44 g (28.5 mmol), quantitative MS (ESI, m/z) 430 (M–H)$^{-1}$H-NMR (CDCl3): 1.44 (9H, s), 1.90-2.01 (1H, m), 2.15-2.25 (1H, m), 2.38-2.55 (2H, m), 3.75 (3H, s), 4.33-4.40 (1H, m), 5.16 (1H, br d).

Step 2

Synthesis of methyl (S)-2-[(t-butoxycarbonyl)amino]-5-[4-(5H-dibenzo[a,d] [7]annulen-5-ylidene)-1-piperidinyl]-5-oxopentanoate:

The title compound was obtained from 5.20 g (17.5 mmol) of the compound obtained in step 1 described above in the same manner as that in step 2 in Referential Example 50.

Yield: 8.35 g (16.2 mmol), 93% MS (ESI, m/z) 517 (M+H)$^{+1}$H-NMR (CDCl$_3$): 1.42 (9H, s), 1.92-2.04 (1H, m), 2.11-2.43 (7H, m), 2.96-3.11 (2H, m), 3.51 (1H, dt), 3.72 (3H, d), 3.89-3.98 (1H, m), 4.27 (1H, br s), 5.29 (1H, br d), 6.92 (2H, s), 7.14-7.19 (2H, m), 7.23-7.28 (2H, m), 7.30-7.35 (4H, m).

Step 3

Synthesis of methyl (S)-5-[4-(5H-dibenzo[a,d] [7]annulen-5-ylidene)-1-piperidinyl]-2-[(2,2-dimethylpropanoyl)amino]-5-oxopentanoate:

The title compound was obtained from 850 mg (1.65 mmol) of the compound obtained in step 2 described above in the same manner as that in Step 3 in Referential Example 50.

Yield: 840 mg (1.68 mmol), quantitative. MS (ESI, m/z) 501 (M+H)$^{+1}$H-NMR (CDCl$_3$): 1.18 (9H, d), 2.07-2.49 (8H, m), 2.96-3.12 (2H, m), 3.46-3.55 (1H, m), 3.71 (3H, d), 3.88-3.98 (1H, m), 4.38-4.46 (1H, m), 6.92 (2H, s), 7.06 (1H, br t), 7.16-7.18 (2H, m), 7.23-7.28 (2H, m), 7.32-7.36 (4H, m).

Step 4

Synthesis of (S)-N-[4-[4-(5H-dibenzo[a,d] [7]annulen-5-ylidene)-1-piperidinyl]-1-(hydroxylmethyl)-4-oxobutyl]-2,2-dimethylpropanamide:

840 mg (1.68 mmol) of the compound obtained in step 3 described above was dissolved in 15 ml of tetrahydrofuran. 0.83 ml of 2 M lithium borohydride/tetrahydrofuran solution was added to the obtained solution at 0° C. in argon atmosphere, and they were stirred at room temperature for 3 hours. Saturated aqueous ammonium chloride solution was added to the reaction mixture under cooling with ice and they were stirred for 10 minutes. The solvent was evaporated under reduced pressure. Ethyl acetate was added to the residue. The resultant mixture was washed with saturated aqueous sodium hydrogencarbonate solution. The organic layer was dried over anhydrous magnesium sulfate, and the solvent was evaporated under reduced pressure. The residue was purified by the silica gel chromatography (dichloromethane: methanol=100:1 to 20:1) to obtain the title compound.

Yield: 717 mg (1.52 mmol), 92% MS (ESI, m/z) 473 (M+H)$^{+1}$H-NMR (CDCl$_3$): 1.16 (9H, d), 1.87-1.96 (2H, m), 2.13-2.50 (6H, m), 2.98-3.12 (2H, m), 3.50-3.57 (3H, m), 3.76-3.92 (2H, m), 3.97 (1H, dt), 6.83-6.89 (1H, m), 6.92 (2H, s), 7.16-7.18 (2H, m), 7.24-7.28 (2H, m), 7.32-7.36 (4H, m).

Referential Example 72

Synthesis of (R)-N-[4-[4-(5H-dibenzo [a, d] [7] annulen-5-ylidene)-1-piperidinyl]-1-(hydroxylmethyl)-4-oxobutyl]-2,2-dimethylpropanamide:

The title compound was obtained from (R)-5-(benzyloxy)-2-[(t-butoxycarbonyl)amino]-5-oxopentanoic acid in the same manner as that of Referential Example 71.

MS (ESI, m/z) 473 (M+H)+ $^1$H-NMR (CDCl$_3$): 1.16 (9H, d), 1.88-1.96 (2H, m), 2.14-2.50 (6H, m), 2.98-3.12 (2H, m), 3.50-3.57 (3H, m), 3.81 (2H, br s), 3.96 (1H, dt), 6.84-6.90 (1H, m), 6.92 (2H, s), 7.15-7.19 (2H, m), 7.23-7.29 (2H, m), 7.31-7.36 (4H, m).

Referential Example 73

Synthesis of (R)-ethyl 3-[4-(5H-dibenzo[a,d][7]annulen-5-ylidene)-1-piperidinyl]-1-(hydroxymethyl)-3-oxopropylcarbamate:

Step 1

Synthesis of methyl (R)-4-[4-[(5H-dibenzo[a,d][7]annulen-5-ylidene)-1-piperidinyl]-2-[(ethoxycarbonyl)amino]-4-oxobutanoate:

2.13 mg (4.23 mmol) of methyl (R)-2-[(t-butoxycarbonyl)amino]-4-[4-(5H-dibenzo[a,d][7]annulen-5-ylidene)-1-piperidinyl]-4-oxobutanoate was dissolved in 30 ml of ethyl acetate. 30 ml of 4 N hydrochloric acid/ethyl acetate was added to the obtained solution under cooling with ice for the duration of 10 minutes, and they were stirred at room temperature for 6 hours. The solvent was evaporated under reduced pressure, and the residue was dissolved in 43 ml of dichloromethane. 0.94 ml (6.36 mmol) of diethyl pyrocarbonate and 1.19 ml (8.54 mmol) of triethylamine were added to the obtained solution under cooling with ice. The resultant mixture was stirred at room temperature for 2 hours. Aqueous ammonium chloride solution was added to the reaction mixture under cooling with ice. After extracting with dichloromethane, the organic layer was dried over anhydrous sodium sulfate. The solvent was evaporated under reduced pressure, and the residue was purified by the silica gel chromatography (hexane:ethyl acetate=3:1 to 1:1) to obtain the title compound.

Yield: 1.83 g (3.85 mmol) (91%) MS (ESI, m/z) 475 (M+H)+ $^1$H-NMR (CDCl$_3$): 1.24 (3H, dt), 2.13-2.34 (4H, m), 2.75 (1H, td), 2.91-3.17 (3H, m), 3.45-3.54 (1H, m), 3.74 (3H, d), 3.89 (1H, dt), 4.06-4.13 (2H, m), 4.56-4 62 (1H, m), 5.92 (1H, br t), 6.92 (2H, s), 7.15-7.18 (2H, m), 7.23-7.28 (2H, m), 7.31-7.36 (4H, m).

Step 2

Synthesis of (R)-ethyl 3-[4-(5H-dibenzo[a,d][7]annulen-5-ylidene)-1-piperidinyl]-1-(hydroxymethyl)-3-oxopropylcarbamate:

The title compound was obtained from 1.82 g (3.84 mmol) of the compound obtained in step 1 described above in the same manner as that in Step 4 in Referential Example 71.

Yield: 1.54 g (3.46 mmol), 90% MS (ESI, m/z) 447 (M+H)+ $^1$H-NMR (CDCl$_3$): 1.19-1.28 (3H, m), 2.14-2.30 (4H, m), 2.70-2.75 (2H, m), 2.93-3.04 (1H, m), 3.07-3.16 (1H, m), 3.45 (1H, br s), 3.58-3.64 (1H, m), 3.69-3.79 (2H, m), 3.90-3.98 (2H, m), 4.04-4.13 (2H, m), 5.64 (1H, br s), 6.92 (2H, s), 7.14-7.19 (2H, m), 7.23-7.37 (6H, m).

Referential Example 74

Synthesis of (S)-t-butyl 4-[(5H-dibenzo[a,d][7]annulen-5-ylidene)-1-piperidinyl]-1-(hydroxymethyl)-4-oxobutylcarbamate:

The title compound was obtained from 890 mg (1.72 mmol) of the compound obtained in step 2 in Referential Example 71 in the same manner as that in Step 4 in Referential Example 71.

Yield: 776 mg (1.59 mmol), 92% MS (ESI, m/z) 489 (M+H)+ $^1$H-NMR (CDCl$_3$): 1.42 (9H, d), 1.73-1.86 (1H, m), 1.92-2.00 (1H, m), 2.13-2.47 (6H, m), 2.93-3.13 (2H, m), 3.29(1H, br s), 3.51-3.56 (4H, m), 3.89-4.00 (1H, m), 5.09 (1H, br s), 6.92 (2H, s), 7.15-7.19 (2H, m), 7.23-7.28 (2H, m), 7.31-7.37 (4H, m).

Referential Example 75

Synthesis of (R)-t-butyl 4-[(5H-dibenzo[a,d][7]annulen-5-ylidene)-1-piperidinyl]-1-(hydroxymethyl)-4-oxobutylcarbamate:

The title compound was obtained in the same manner as that in Referential Example 74.

MS (ESI, m/z) 489 (M+H)+ $^1$H-NMR (CDCl$_3$): 1.43 (9H, d), 1.73-1.89 (1H, m), 1.90-2.01 (1H, m), 2.14-2.48 (6H, m), 2.93-3.13 (2H, m), 3.27 (1H, br s), 3.49-3.59 (4H, m), 3.89-4.01 (1H, m), 5.09 (1H, br s), 6.92 (2H, s), 7.14-7.19 (2H, m), 7.23-7.28 (2H, m), 7.31-7.36 (4H, m).

Referential Example 76

Synthesis of tert-butyl (1R)-1-(hydroxymethyl)-3-oxo-3-[4-(9H-thioxanthen-9-ylidene)-1-piperidinyl]propylcarbamate:

Step 1

Synthesis of methyl (2R)-2-[(t-butoxycarbonyl)amino]-4-oxo-4-[4-(9H-thioxanthen-9-ylidene)-1-piperidinyl]butanoate:

1.00 g (5.22 mmol) of 1-ethyl-3-(3'-dimethylaminopropyl) carbodiimide hydrochloride, 0.73 ml (5.24 mmol) of triethylamine and 1.351 g (4.84 mmol) of 4-(9H-thioxanthen-9-ylidene)piperidine were added to 1.290 g (5.22 mmol) of (S)-3-[(t-butoxycarbonyl)amino]-4-methoxy-4-oxobutanoic acid in 20 ml of dichloromethane in an ice bath, and they were stirred at room temperature overnight. Saturated aqueous ammonium chloride solution was added to the reaction mixture. After extracting with dichloromethane, the organic layer was dried over anhydrous sodium sulfate, and the solvent was evaporated under reduced pressure. The residue was purified by the silica gel chromatography (hexane:ethyl acetate=7:3 to 1:1) to obtain the title compound.

Yield: 1.645 g (3.23 mmol), 67% MS (ESI, m/z) 509 (M+H)+ $^1$H-NMR (CDCl$_3$): 1.45 (9H, d), 2.48-3.24 (8H, m), 3.58-4.20 (5H, m), 4.52-4.66 (1H, m), 5.80 (1H, t), 7.17-7.32 (6H, m), 7.51 (2H, d).

Step 2

Synthesis of tert-butyl (1R)-1-(hydroxymethyl)-3-oxo-3-[4-(9H-thioxanthen-9-ylidene)-1-piperidinyl]propylcarbamate:

The title compound was obtained from 714 mg (1.40 mmol) of the compound obtained in Step 1 described above in the same manner as that in Step 4 in Referential Example 71.

Yield: 554 mg (1.15 mmol), 82% MS (ESI, m/z) 481 (M+H)+ $^1$H-NMR (CDCl$_3$): 1.44 (9H, d), 2.49-3.22 (8H, m), 3.48-3.98 (5H, m), 4.15-4.26 (1H, m), 5.52 (1H, m), 7.17-7.31 (6H, m), 7.51 (2H, d).

Referential Example 77

Synthesis of N-{(1R)-1-(hydroxymethyl)-3-oxo-3-[4-(9H-thioxanthen-9-ylidene)-1-piperidinyl]propyl}-2,2-dimethylpropanamide:

Step 1

Synthesis of methyl (2R)-2-[(2,2-dimethylpropanoyl)amino]-4-oxo-4-[4-(9H-thioxanthen-9-ylidene)-1-piperidinyl]butanoate:

The title compound was obtained from 821 mg (1.61 mmol) of the compound obtained in Step 1 in Referential Example 76 in the same manner as that in Step 3 in Referential Example 50.

MS (ESI, m/z) 493 (M+H)$^{+1}$H-NMR (CDCl$_3$): 1.22 (9H, d), 2.46-3.26 (8H, m), 3.58-4.20 (5H, m), 4.81-4.96 (1H, m), 7.04-7.10 (1H, m), 7.17-7.32 (6H, m), 7.51 (2H, d).

Step 2

Synthesis of N-{(1R)-1-(hydroxymethyl)-3-oxo-3-[4-(9H-thioxanthen-9-ylidene)-1-piperidinyl]propyl}-2,2-dimethylpropanamide:

The title compound was obtained from the whole amount of the compound obtained in Step 1 described above in the same manner as that in Step 4 in Referential Example 71.

Yield: 574 mg (1.24 mmol), 77% (2steps) MS (ESI, m/z) 465 M+H)$^{+1}$H-NMR (CDCl3): 1.20 (9H, d), 2.47-3.25 (8H, m), 3.62-4.27 (6H, m), 6.91-7.02 (1H, m), 7.17-7.31 (6H, m), 7.51 (2H, d).

Referential Example 78

Synthesis of (S)-N-[4-[4-(10,11)-dihydro-5H-dibenzo[a,d][7]annulen-5-ylidene]-1-piperidinyl]-1-(hydroxymethyl)-4-oxobutyl]-2,2-dimethylpropanamide:

1.91 g (4.04 mmol) of the compound obtained in Referential Example 71 was dissolved in 100 ml of ethanol. 2.5 g of palladium carbon (10% w/v) was added to the obtained solution, and they were stirred at room temperature in hydrogen gas atmosphere under a pressure of 5 atm. for 3.5 hours. The catalyst was filtered out, and the filtrate was concentrated under reduced pressure. The residue was purified by the silica gel chromatography (dichloromethane: methanol=60:1 to 20:1) to obtain the title compound.

Yield: 1.77 g (3.73 mmol), 92% MS (ESI, m/z) 475 (M+H)$^{+1}$H-NMR (CDCl3): 1.18 (9H, d), 1.90-1.99 (2H, m), 2.27-2.48 (6H, m), 2.78-2.90 (2H, m), 3.10-3.25 (2H, m), 3.32-3.42 (2H, m), 3.53-3.64 (3H, m), 3.74-3.88 (2H, m), 4.06 (1H, dt), 6.89 (1H, dd), 7.02-7.04 (2H, m), 7.09-7.17 (6H, m).

Referential Example 79

Synthesis of N-[(1S)-2-[4-(5H-dibenzo[a,d][7]annulen-5-ylidene)-1-piperidinyl]-1-(hydroxymethyl)-2-oxoethyl]-2,2-dimethylpropanamide:

Step 1

Synthesis of pivaloyl-L-serine:

5.25 g (50.0 mmol) of L-serine was dissolved in 1 N aqueous sodium hydroxide solution. 50 ml of 1 N aqueous sodium hydroxide solution and a solution of 5 ml (40.6 mmol) of pivaloyl chloride in 12 ml of diethyl ether were simultaneously added dropwise to the obtained solution in the ice bath for the duration of 25 minutes. After stirring for 2.5 hours, 70 ml of 1 N hydrochloric acid was added to the reaction mixture to make it acidic. After extracting with ethyl acetate, the organic layer was dried over anhydrous sodium sulfate, and the solvent was evaporated under reduced pressure to obtain the title compound.

Yield: 3.95 g (20.9 mmol), 52% $^1$H-NMR (DMSO):1.12 (9H, s), 3.61-3.75 (2H, m), 4.19-4.26 (1H, m).

Step 2

Synthesis of N-[(1S)-2-[4-(5H-dibenzo[a,d][7]annulen-5-ylidene)-1-piperidinyl]-1-(hydroxymethyl)-2-oxoethyl]-2,2-dimethylpropanamide:

880 mg (4.59 mmol) of 1-ethyl-3-(3'-dimethylaminopropyl)carbodiimide hydrochloride, 0.63 ml (4.52 mmol) of triethylamine and 860 mg (4.55 mmol) of pivaloyl-L-serine were added to 1.231 g (4.50 mmol) of 4-(5H-dibenzo[a,d][7]annulen-5-ylidene)piperidine in 20 ml of dichloromethane in the ice bath, and they were stirred at room temperature overnight. 1 N hydrochloric acid was added to the reaction mixture. After extracting with dichloromethane, the organic layer was dried over anhydrous sodium sulfate. The solvent was evaporated under reduced pressure. The residue was purified by the silica gel chromatography (hexane:ethyl acetate=7:3 to 1:2) to obtain the title compound.

Yield: 1.032 g (2.32 mmol), 52% MS (ESI, m/z) 445 (M+H)$^{+1}$H-NMR (CDCl$_3$): 1.22 (9H, d), 2.14-2.44 (4H, m), 2.90-3.27 (2H, m), 3.61-4.06 (5H, m), 4.80-4.89 (1H, m), 6.92 (2H, s), 7.01-7.38 (8H, m).

Referential Example 80

Synthesis of N-[(1R)-2-[4-(5H-dibenzo[a,d][7]annulen-5-ylidene)-1-piperidinyl]-1-(hydroxymethyl)-2-oxoethyl]-2,2-dimethylpropanamide:

The title compound was obtained from D-serine in the same manner as that in Referential Example 79.

MS (ESI, m/z) 445 (M+H)$^{+1}$H-NMR (CDCl$_3$): 1.22 (9H, d), 2.16-2.44 (4H, m), 2.90-3.26 (2H, m), 3.62-4.06 (5H, m), 4.79-4.89 (1H, m), 6.92 (2H, s), 7.01-7.38 (8H, m).

Referential Example 81

Synthesis of N-{(1S)-1-(hydroxymethyl)-4-oxo-4-[4-(9H-thioxanthen-9-ylidene)-1-piperidinyl]butyl}-2,2-dimethylpropanamide:

Step 1

Synthesis of methyl (2S)-2-[(t-butoxycarbonyl)amino]-5-oxo-5-[4-(9H-thioxanthen-9-ylidene)-1-piperidinyl]pentanoate:

The title compound was obtained from 511 mg (1.96 mmol) of the compound obtained in Step 1 in Referential Example 71 and 470 mg (1.68 mmol) of 4-(9H-thioxanthen-9-ylidene)piperidine in the same manner as that in Step 2 in Referential Example 50.

Yield: 742 mg (1.42 mmol), 85% MS (ESI, m/z) 523 (M+H)$^{+1}$H-NMR (CDCl$_3$): 1.44 (9H, d), 1.91-2.79 (8H, m), 2.88-3.18 (2H, m), 3.62-3.74 (1H, m), 3.75 (3H, d), 4.12-4.38 (2H, m), 5.26-5.37 (1H, m), 7.17-7.53 (8H, m).

Step 2

Synthesis of methyl (2S)-2-[(2,2-dimethylpropanoyl)amino]-5-oxo-5-[4-(9H-thioxanthen-9-ylidene)-1-piperidinyl]pentanoate:

The title compound was obtained from 736 mg (1.41 mmol) of the compound obtained in Step 1 described above in the same manner as that in Step 3 in Referential Example 50.

$^1$H-NMR (CDCl$_3$): 1.20 (9H, d), 2.04-2.80 (8H, m), 2.88-3.18 (2H, m), 3.60-3.78 (4H, m), 4.11-4.26 (1H, m), 4.41-4.52 (1H, m), 7.04 (1H, t), 7.17-7.33 (6H, m), 7.51 (2H, d).

Step 3

Synthesis of N-{(1S)-1-(hydroxymethyl)-4-oxo-4-[4-(9H-thioxanthen-9-ylidene)-1-piperidinyl]butyl}-2,2-dimethylpropanamide:

The title compound was obtained from the whole amount of the compound obtained in Step 2 described above in the same manner as that in Step 4 in Referential Example 71.

Yield: 564 mg (1.18 mmol), 84% (step 2) MS (ESI, m/z) 479 (M+H)$^{+1}$H-NMR (CDCl$_3$): 1.18 (9H, d), 1.86-2.02 (2H, m), 2.28-2.82 (6H, m), 2.92-3.18 (2H, m), 3.48-3.88 (5H, m), 4.14-4.26 (1H, m), 6.79-6.92 (1H, m), 7.17-7.31 (6H, m), 7.51 (2H, d).

Referential Example 82

Synthesis of (S)-tert-butyl 1-{[4-(5H-dibenzo[a,d][7]annulen-5-ylidene)-1-piperidinyl]carbonyl}-3-hydroxypropylcarbamate:

Step 1

Synthesis of benzyl (S)-3-[(tert-butoxycarbonyl)amino]-4-[4-(5H-dibenzo[a,d] [7]annulen-5-ylidene)-1-piperidinyl]-4-oxobutanoate:

10 ml of methylene chloride, 306 mg (1.60 mmol) of 1-ethyl-3-(3'-dimethylaminopropyl)carbodiimide hydrochloride, 421 mg (1.54 mmol) of 4-(5H-dibenzo[a,d][7]annulen-5-ylidene)-1-piperidine, 212 mg (1.57 mmol) of 1-hydroxybenzotriazole and 0.23 ml (1.65 mmol) of triethylamine were added to 498 mg (1.54 mmol) of (S)-4-(benzyloxy)-2-[(t-butoxycarbonyl)amino]-4-oxobutanoic acid, and they were stirred at room temperature overnight. Saturated aqueous ammonium chloride solution was added to the reaction mixture. After extracting with methylene chloride, the organic layer was dried over anhydrous sodium sulfate, and the solvent was evaporated under reduced pressure. The residue was purified by the silica gel chromatography (hexane:ethyl acetate=7:3) to obtain the title compound.

Yield: 839 mg (1.45 mmol), 94% $^1$H-NMR (CDCl3): 1.50 (9H, d), 2.08-2.38 (4H, m), 2.54-3.28 (4H, m), 3.62-4.04 (2H, m), 4.92-5.03 (1H, m), 5.10 (2H, d), 7.13-7.39 (8H, m)

Step 2

Synthesis of (S)-tert-butyl 1-{[4-(5H-dibenzo[a,d][7]annulen-5-ylidene)-1-piperidinyl]carbonyl}-3-hydroxypropylcarbamate:

797 mg (1.38 mmol) of benzyl (S)-3-[(tert-butoxycarbonyl)amino]-4-[4-(5H-dibenzo[a, d][7]annulen-5-ylidene)-1-piperidinyl]-4-oxobutanoate was dissolved in 15 ml of tetrahydrofuran. 1.45 ml of 2 M lithium borohydride/tetrahydrofuran solution was added to the obtained solution in argon atmosphere at 0° C., and they were stirred at room temperature overnight. Saturated aqueous ammonium chloride solution was added to the reaction mixture under cooling with ice. After extracting with ethyl acetate, the organic layer was dried over anhydrous sodium sulfate and then the solvent was evaporated under reduced pressure. The residue was purified by the silica gel chromatography (hexane:ethyl acetate=3:1 to 1:1) to obtain the title compound.

Yield: 180 mg (1.45 mmol), 28% MS (ESI, m/z) 475 (M+H)$^{+1}$H-NMR (CDCl$_3$): 1.44 (9H, d), 1.20-1.99 (2H, m), 2.94-3.22 (2H, m), 3.54-4.03 (4H, m), 4.67-4.78 (1H, m), 5.77 (1H, d), 6.92 (2H, d), 7.18-7.38 (8H, m)

Referential Example 83

Synthesis of (S)-N-[4-[4-(5H-dibenzo[a,d] [7] annulen-5-ylidene)-1-piperidinyl]-1-(hydroxymethyl)-4-oxobutyl]acetamide:

Step 1

Synthesis of (S)-2-amino-5-[4-(5H-dibenzo[a,d][7]annulen-5-ylidene)-1-piperidinyl]-5-oxo-1-pentanol Hydrochloride:

(S)-t-butyl 4-[(5H-dibenzo[a,d] [7]annulen-5-ylidene)-1-piperidinyl]-1 -(hydroxymethyl)-4-oxobutylcarbamate was dissolved in 5 ml of ethyl acetate. 10 ml of 4 N hydrochloric acid/ethyl acetate was added to the solution in the ice bath, and they were stirred for 6.5 hours. The reaction solution was concentrated under reduced pressure to obtain the title compound.

Yield: 607 mg (1.43 mmol), 100%

Step 2

Synthesis of (S)-N-[4-[4-(5H-dibenzo[a,d] [7]annulen-5-ylidene)-1-piperidinyl]-1-(hydroxymethyl)-4-oxobutyl]acetamide:

2 ml of 1 N aqueous sodium hydroxide solution, 3 nil of diethyl ether and 2 ml of ethyl acetate were added to 151 mg (0.36 mmol) of (S)-2-amino-5-[4-(5H-dibenzo[a,d] [7]annulen-5-ylidene)-1-piperidinyl]-5-oxo-1-pentanol hydrochloride. 0.04 ml (0.56 mmol) of acetyl chloride was added dropwise to the obtained solution under vigorous stirring, and they were stirred at room temperature for 2 hours. Water was added to the reaction mixture. After extracting with ethyl acetate, the organic layer was dried over anhydrous sodium sulfate and then concentrated under reduced pressure. The residue was purified by the silica gel chromatography (chloroform:methanol=200:1 to 50:1) to obtain the title compound.

Yield: 114 mg (0.27 mmol), 75% MS (ESI, m/z) 431 (M+H)$^{+1}$H-NMR (CDCl$_3$): 1.70-1.97 (2H, m), 1.96 (3H, s), 2.12-2.31 (4H, m), 2.34-2.43 (2H, m), 2.95-3.13 (2H, m), 3.48-3.59 (3H, m), 3.74-4.01 (3H, m), 6.67 (1H, t), 6.92 (2H, d), 7.15-7.37 (8H, m)

Referential Example 84

Synthesis of (S)-N-[4-[4-(5H-dibenzo[a,d] [7]annulen-5-ylidene)-1-piperidinyl]-1-(hydroxymethyl)-4-oxobutyl]-2-methylpropanamide:

The title compound was obtained by using isobutyryl chloride in the same manner as that in Step 2 in Referential Example 83.

Yield: 108 mg (0.23 mmol), 72% MS (ESI, m/z) 459 (M+H)$^{+1}$H-NMR (CDCl$_3$): 1.07-1.20 (6H, m), 1.93 (2H, qua), 2.12-2.48 (7H, m), 2.94-3.13 (2H, m), 3.48-3.62 (3H, m), 3.76-4.02 (2H, m), 6.65-6.76 (1H, m), 6.92 (2H, m), 7.14-7.38 (8H, m)

Referential Example 85

Synthesis of (S)-N-[4-[4-(5H-dibenzo[a,d] [7] annulen-5-ylidene)-1-piperidinyl]-1-(hydroxymethyl)-4-oxobutyl]cyclohexanecarboxamide:

The title compound was obtained by using cyclohexanoyl chloride in the same manner as that in Step 2 in Referential Example 83.

Yield: 87 mg (0.17 mmol), 68%. MS (ESI, m/z) 499 (M+H)$^{+1}$H-NMR (CDCl$_3$): 1.12-1.51 (6H, m), 1.58-2.48 (13H, m), 2.95-3.12 (2H, m), 3.46-3.60 (3H, m), 3.75-4.02 (3H, m), 6.55-6.65 (1H, m), 6.92 (2H, m), 7.14-7.38 (8H, m)

Referential Example 86

Synthesis of (S)-N-[4-[4-(5H-dibenzo[a,d] [7] annulen-5-ylidene)-1-piperidinyl]-1-(hydroxymethyl)-4-oxobutyl]-2-benzamide:

The title compound was obtained by using benzoyl chloride in the same manner as that in Step 2 in Referential Example 83.

Yield: 95 mg (0.19 mmol), 75%. MS (ESI, m/z) 493 (M+H)$^+$ $^1$H-NMR (CDCl3): 1.94-2.32 (6H, m), 2.35-2.58 (2H, m), 2.90-3.11 (2H, m), 3.47-3.59 (1H, m), 3.88-4.13 (2H, m), 6.90 (2H, d), 7.06-7.67 (12H, m), 7.78-7.89 (2H, m)

The structural formulae of the compounds obtained in Referential Examples 1 to 86 are shown in Tables 3 to 13.

TABLE 3

| Ref. Example | Structural formula |
| --- | --- |
| 1 | |
| 2 | (ClH) |
| 3 | |
| 4 | Chiral |
| 5 | Chiral |

TABLE 3-continued

| Ref. Example | Structural formula |
| --- | --- |
| 6 | Chiral |
| 8 | |
| 9 | |

TABLE 4

| Ref. Example | Structural formula |
| --- | --- |
| 10 | ClH |
| 11 | |

TABLE 4-continued
| Ref. Example | Structural formula |
|---|---|
| 12 | 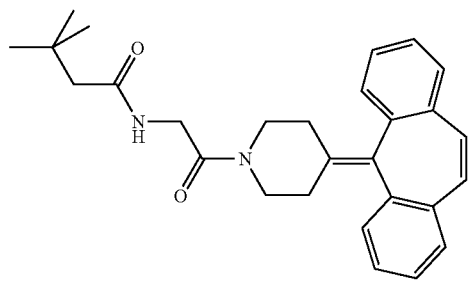 |
| 13 | 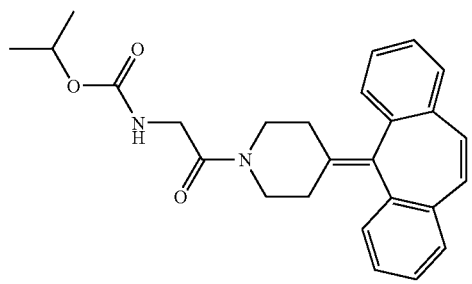 |
| 14 | 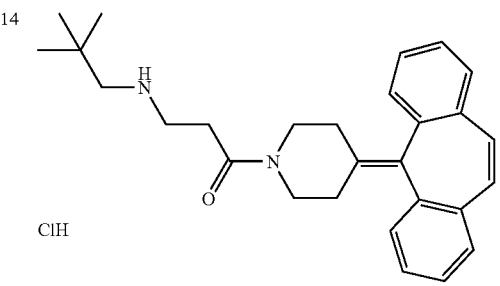  ClH |
| 15 | Chiral 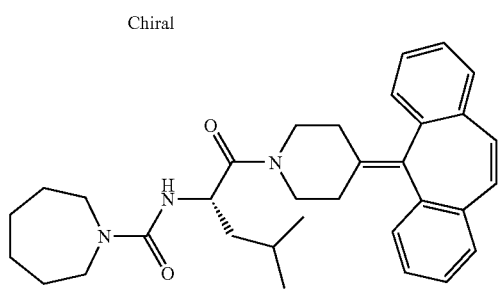 |
TABLE 4-continued
| Ref. Example | Structural formula |
|---|---|
| 16 | 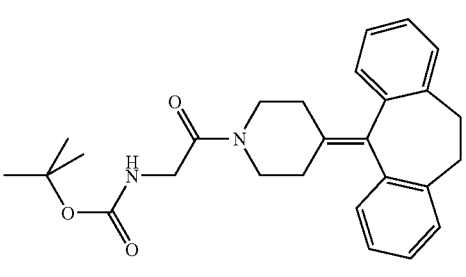 |
| 17 | 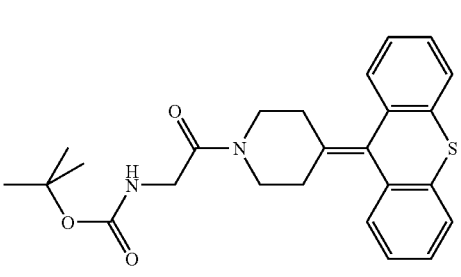 |
TABLE 5
| Ref. Example | Structural formula |
|---|---|
| 18 | 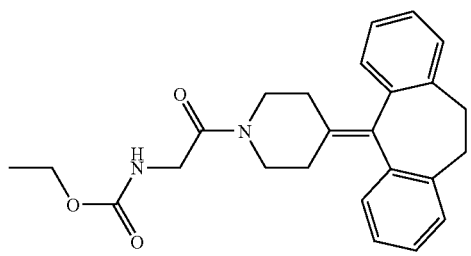 |
| 19 | 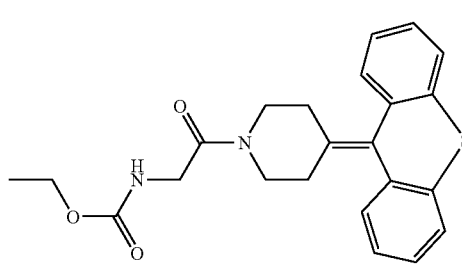 |

TABLE 5-continued
| Ref. Example | Structural formula |
|---|---|
| 20 | 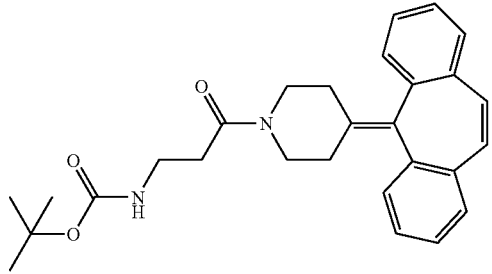 |
| 21 | 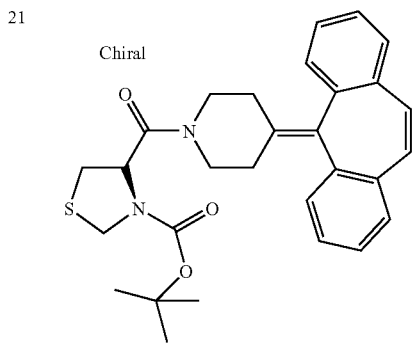 Chiral |
| 22 | 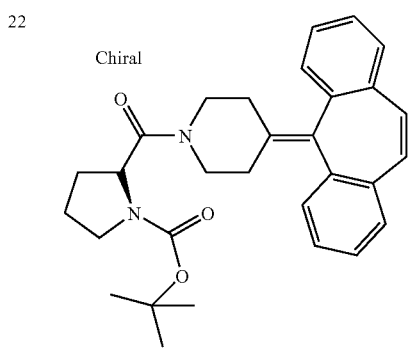 Chiral |
TABLE 5-continued
| Ref. Example | Structural formula |
|---|---|
| 23 | 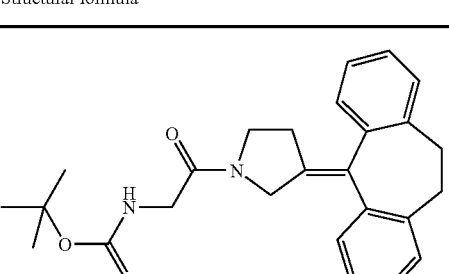 |
| 24 | 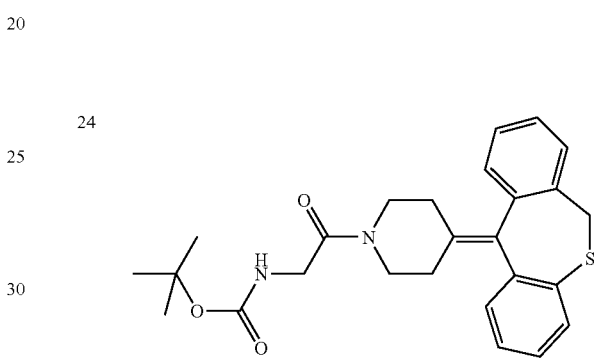 |
| 25 | 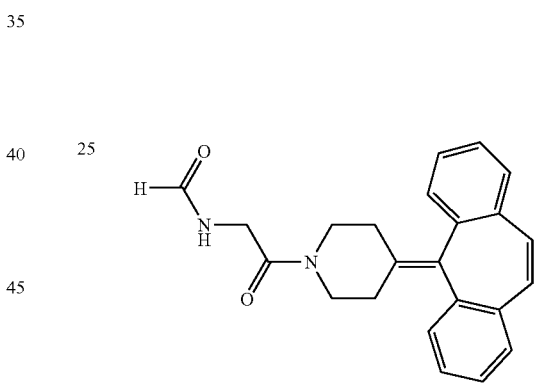 |
TABLE 6
| Ref. Example | Structural formula |
|---|---|
| 26 | 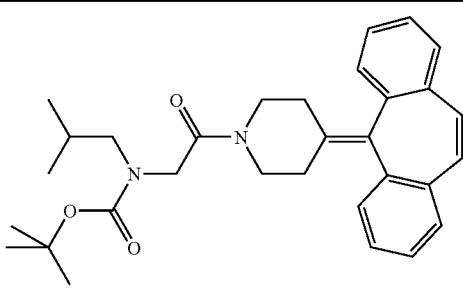 |

TABLE 6-continued
| Ref. Example | Structural formula |
|---|---|
| 27 | 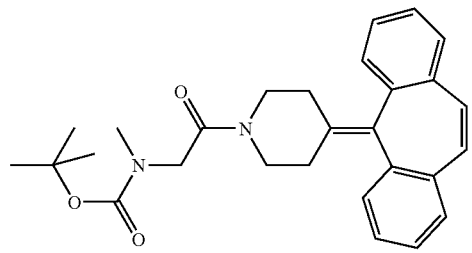 |
| 28 | 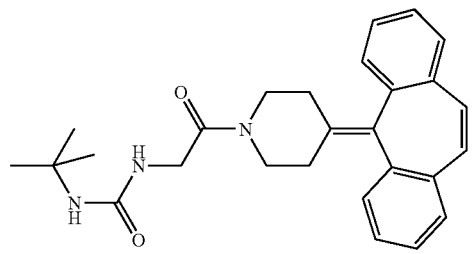 |
| 29 | 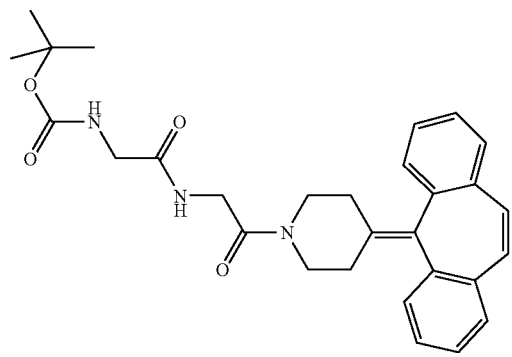 |
| 30 | 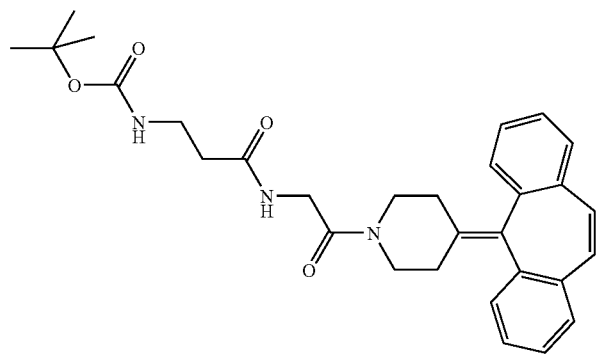 |
| 31 | 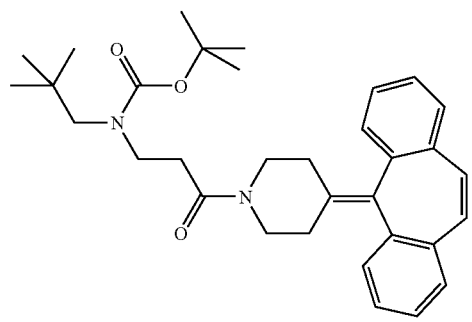 |

TABLE 6-continued
| Ref. Example | Structural formula |
|---|---|
| 32 | 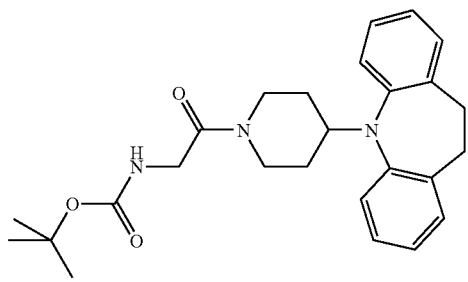 |
| 33 | 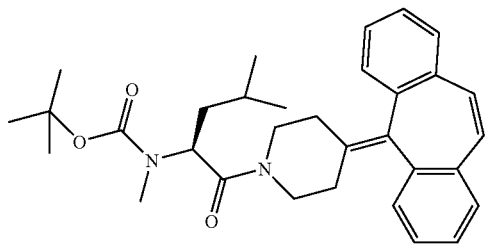 |
TABLE 7
| Ref. Example | Structural formula |
|---|---|
| 34 | ClH 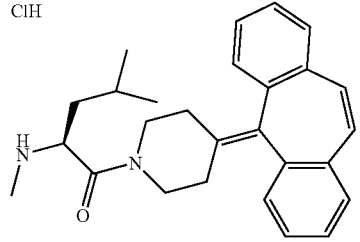 |
| 35 | 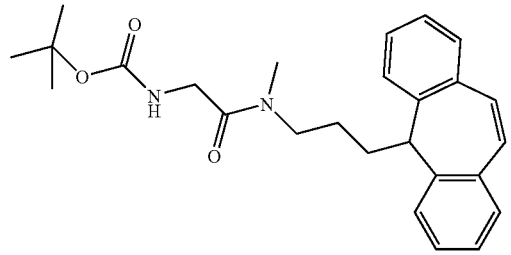 |
| 36 | 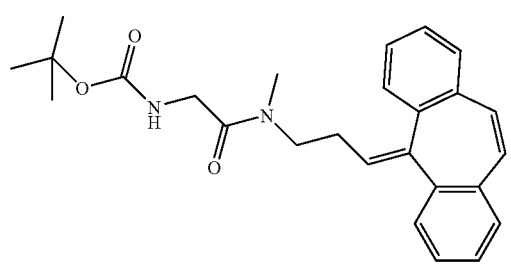 |
| 37 | 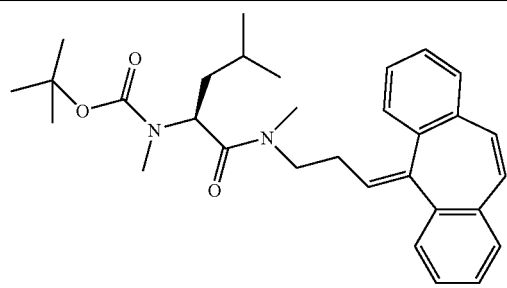 |
| 38 | 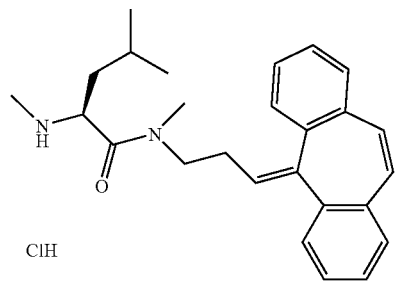 ClH |
| 39 | 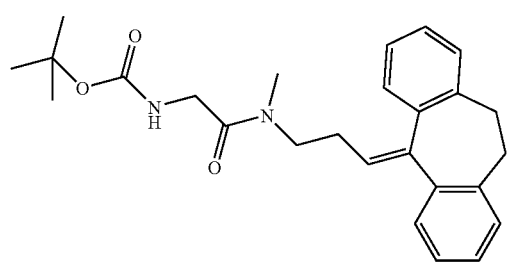 |

TABLE 7-continued
| Ref. Example | Structural formula |
|---|---|
| 40 | 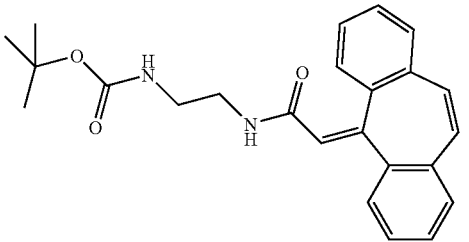 |
| 41 | 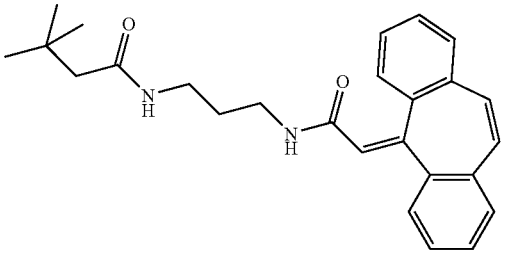 |
TABLE 8
| Ref. Example | Structural formula |
|---|---|
| 42 | 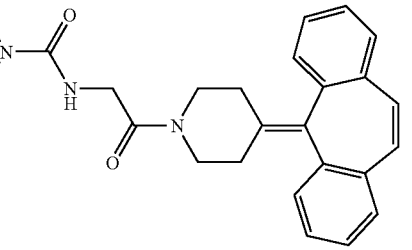 |
| 43 | 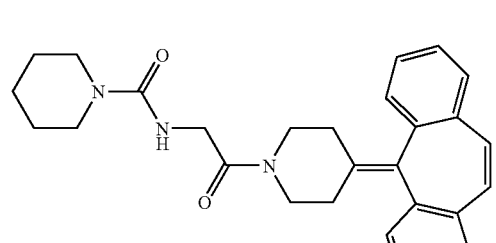 |
| 44 | 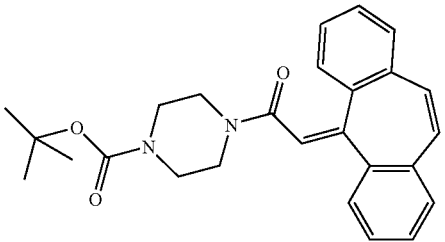 |
| 45 | 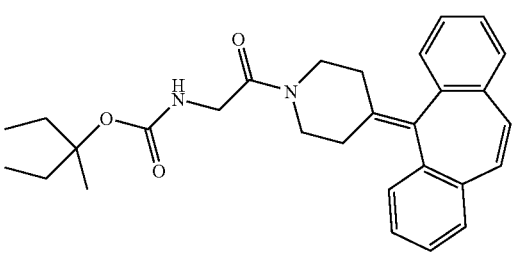 |
| 46 | 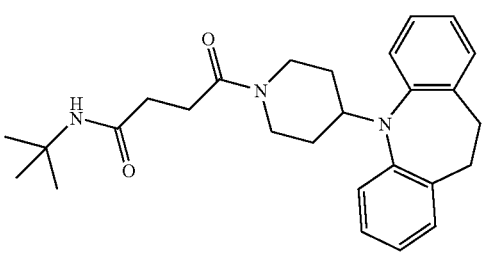 |
| 47 | 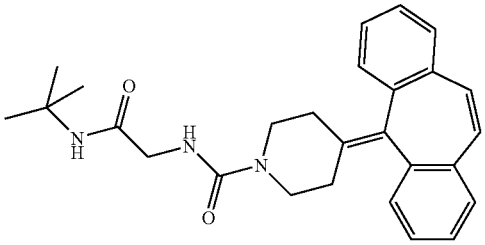 |
| 48 | 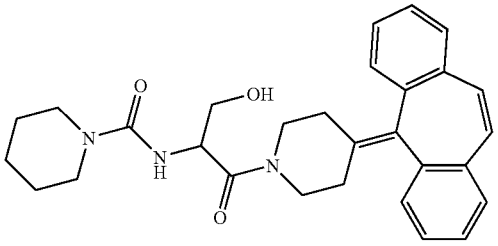 |
| 49 | 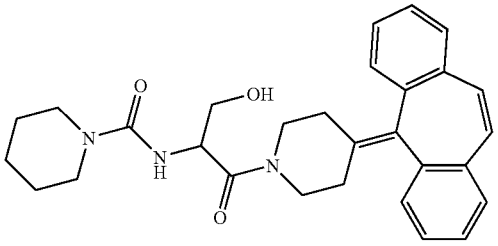 |

TABLE 9
| Ref. Example | Structural formula |
|---|---|
| 50 | 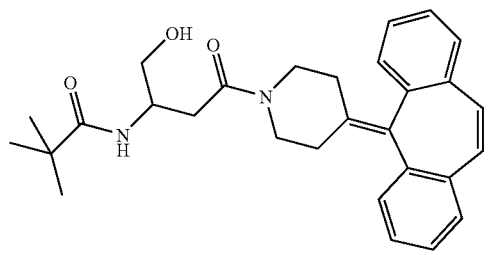 |
| 51 | 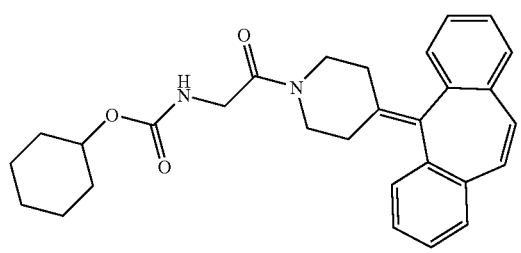 |
| 52 | 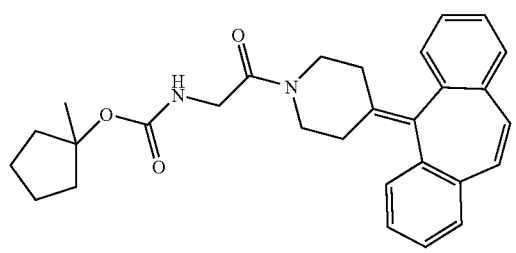 |
| 53 | 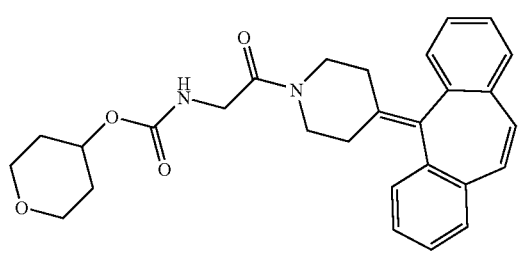 |
| 54 | 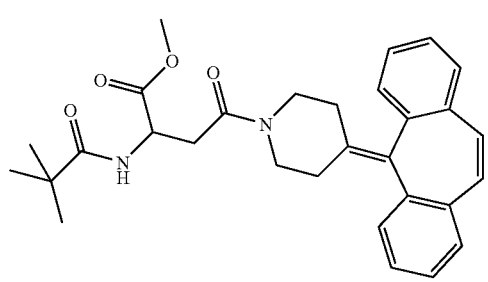 |
TABLE 9-continued
| Ref. Example | Structural formula |
|---|---|
| 55 | 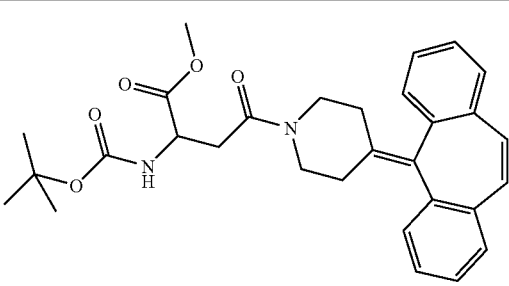 |
| 56 | 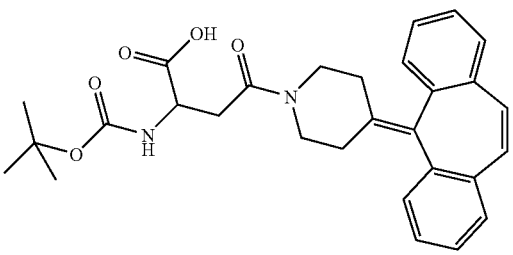 |
| 57 | 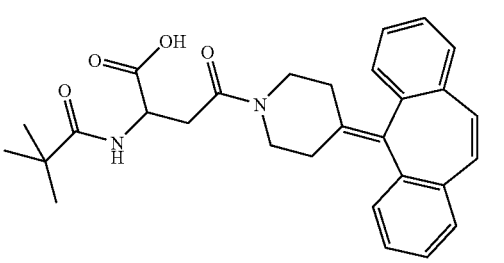 |
TABLE 10
| Ref. Example | Structural formula |
|---|---|
| 58 | 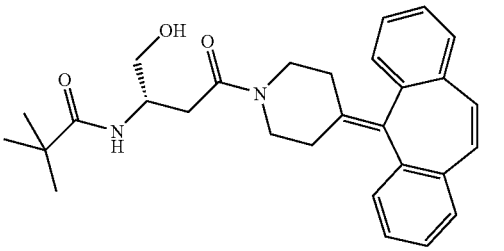 (S) |

TABLE 10-continued
| Ref. Example | Structural formula |
|---|---|
| 59 | 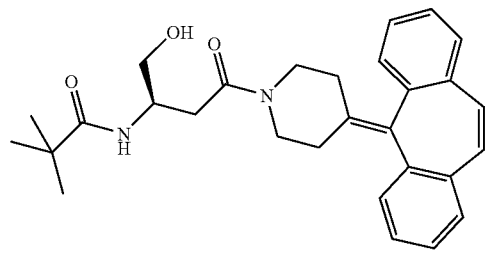 (R) |
| 60 | 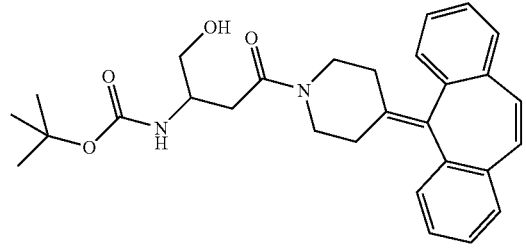 |
| 61 | 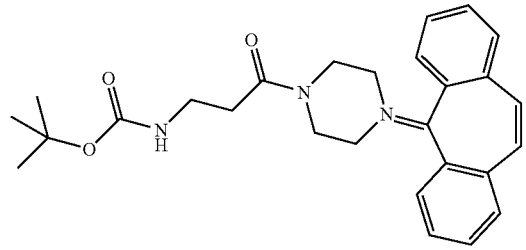 |
| 62 | 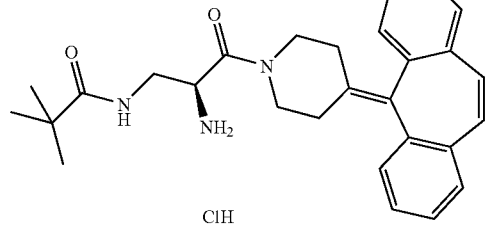 ClH (S) |
| 63 | 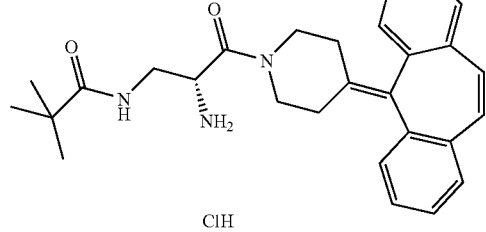 ClH (R) |
TABLE 10-continued
| Ref. Example | Structural formula |
|---|---|
| 64 | 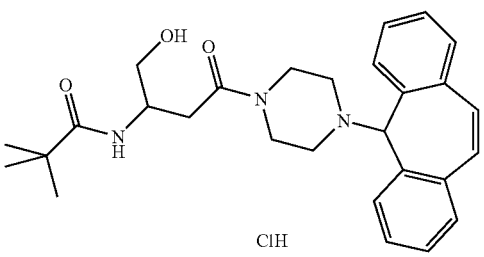 ClH |
| 65 | 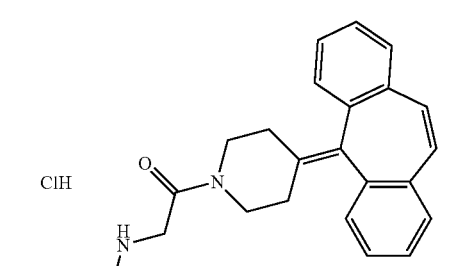 ClH (R) |
TABLE 11
| Ref. Example | Structural formula |
|---|---|
| 66 | 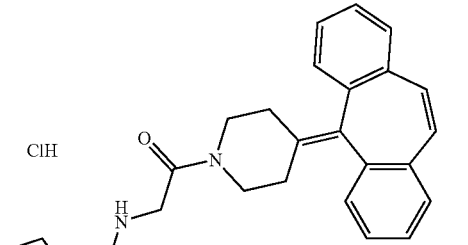 ClH (S) |
| 67 | 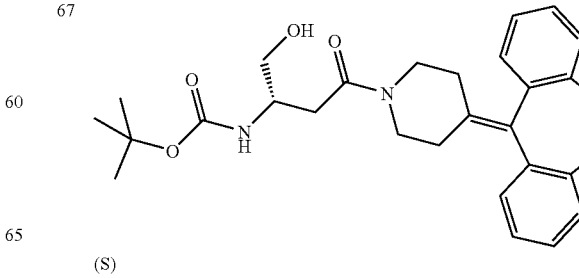 (S) |

TABLE 11-continued

| Ref. Example | Structural formula |
|---|---|
| 68 | (R) |
| 69 | (R) |
| 70 | (S) |
| 71 | (S) |
| 72 | (R) |
| 73 | (R) |

TABLE 12

| Ref. Example | Structural formula |
|---|---|
| 74 | (S) |

TABLE 12-continued
| Ref. Example | Structural formula |
|---|---|
| 75 | 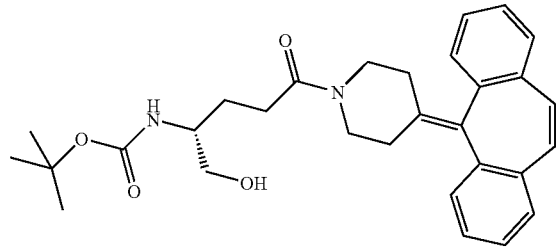<br>(R) |
| 76 | 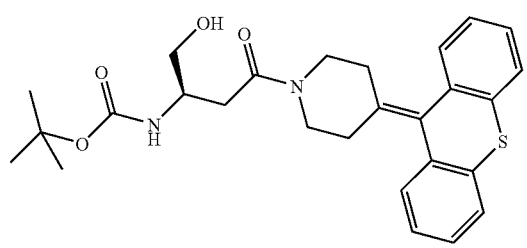<br>(R) |
| 77 | 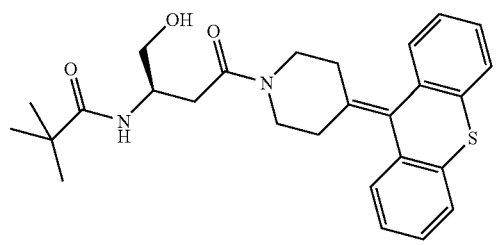<br>(R) |
| 78 | 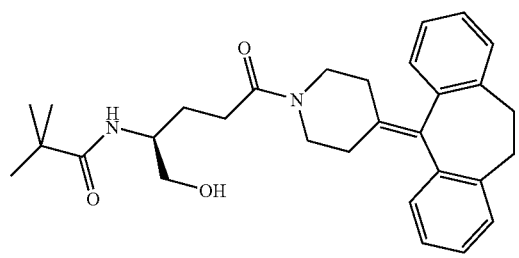<br>(S) |
| 79 | 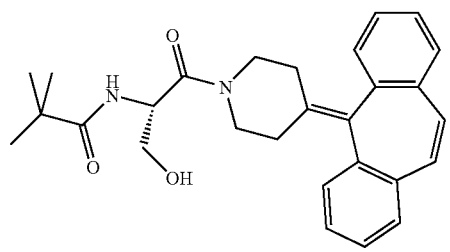<br>(S) |

TABLE 12-continued
| Ref. Example | Structural formula |
| --- | --- |
| 80 | 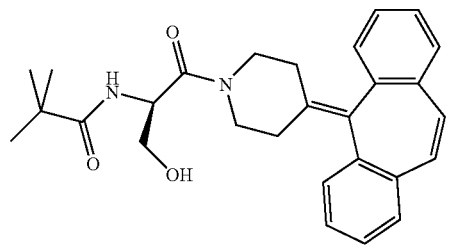<br>(R) |
| 81 | 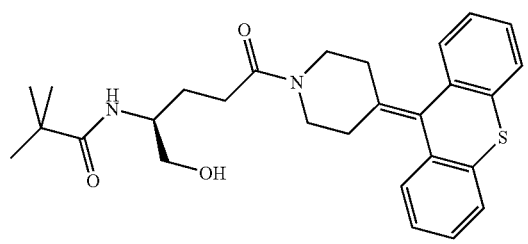<br>(S) |
TABLE 13
| Ref. Example | Structural formula |
| --- | --- |
| 82 | 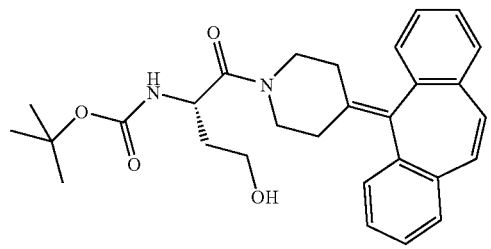<br>(S) |
| 83 | 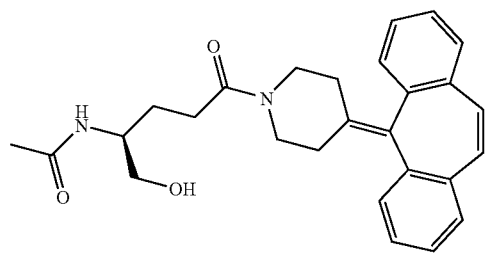<br>(S) |
| 84 | 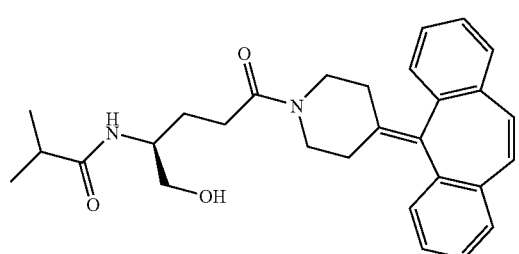<br>(S) |

TABLE 13-continued

| Ref. Example | Structural formula |
|---|---|
| 85 | 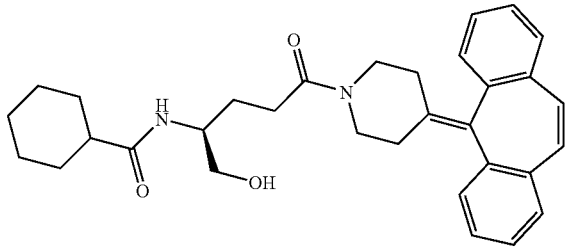 (S) |
| 86 | 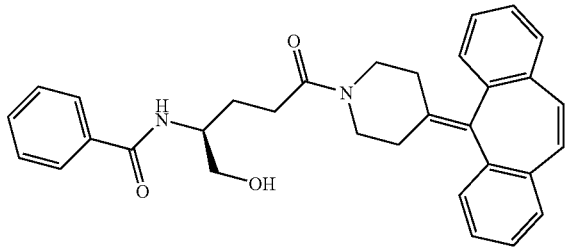 (S) |

Referential Test Example 1

Antagonistic Activity on N-Type Calcium Channel
(Fluorescence Dye Method)

Human neuroblastoma cells IMR-32 were obtained from ATCC (American Type Culture Collection). The medium used was a Phenol Red-free Eagle minimum essential medium containing earle's salts supplement (GIBCO) supplemented with 2 mM of L-glutamine (GIBCO), 1 mM of sodium pyruvate (pH 6.5) (GIBCO), antibiotic/antimycotic mixture (GIBCO) and 10% fetal calf serum (Cell Culture Technologies). 3 ml of $1 \times 10^5$ cells/ml IMR-32 cells were spread on the glass bottom of a dish (Iwaki Glsss Co., Ltd.) having a diameter of 35 mm which had been treated with poly-L-lysin (SIGMA) and collagen (COLLAGEN VITROGEN 100; Collagen Co.). After the culture for 1 day, 1 mM (final concentration) of dibutyl cAMP and 2.5 µM (final concentration) of 5-bromodeoxyuridine (SIGMA) were added. After the culture for additional 10 to 14 days, the cells were subjected to the activity determination.

The medium for IMR-32 cells thus prepared was replaced with 1 ml of Phenol Red-free and earle's salts supplemented Eagle minimum essential medium (GIBCO) containing 2.5 µM fura-2/AM (Dojin Kagaku, Co.), and the incubation was conducted at 37° C. for 30 minutes. Then the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channel was determined and analyzed using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 µM of Nifedipine was given to the cells by reflux by a Y-tube method for 2 minutes. Then a stimulating agent containing 60 mM of potassium chloride was rapidly given by the Y-tube method. The calcium concentration change in the cells in this step was shown as the N-type calcium channel activity. Then stimulating agents containing 60 mM of potassium chloride and 0.1, 1 or 10 µM of the test compound were successively and rapidly given to the cells by the Y-tube method to determine the change in the intracellular calcium concentration. The antagonistic activity on N-type calcium channel was calculated from the inhibition rate (%) at a concentration of 10 µM.

Rerential Test Example 2

Antagonistic Activity on L-Type Calcium Channel

The antagonistic activity of the new diarylalkene derivatives and diarylalkyl derivatives of the present invention to inhibit L-type calcium channel was determined by the following method in which the relaxation response against the KCl-induced contraction of isolated rat thoracic aorta was employed.

1) Method of Preparation of Rat Thoracic Aorta:

The slips of thoracic aorta isolated from a Wistar rat were used. The aorta was cut to obtain ring-shaped samples having a width of about 3 mm. The endothelial cells of the samples were mechanically removed. The samples were suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied thereto. The tension of the blood vessel was amplified with a transducer and a tension amplifier (EF-601G; Nihon Koden Corporation) and recorded with a multi-pen recorder (Rikadenki Kogyo Co., Ltd.). The experiments were conducted at 37° C.

2) Measurement of Relaxation Response Against KCl-Induced contraction:

After the tension had been stabilized, the nutrient solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. Thirty minutes after, the solution in the sample tank was replaced with the normal Tyrode's solution. The solution in the sample tank was again replaced with the High K$^+$ Tyrode's solution and the contraction reaction was observed. After attaining the maximum contraction reaction, the test compound was cumulatively added at intervals of 90 minutes to attain concentrations of $10^{-9}$, $10^{-8}$, $10^{-7}$ and $10^{-6}$ M. The inhibitory rate of the test compound against the maximum contraction response was employed as the index of the antagonistic activity on L-type calcium channels.

Table 14 shows the results of the measurement of the antagonistic activities on N-type calcium channels (inhibition rate at 10 μM: %) and L-type calcium channel ($pIC_{50}$). The value of $pIC_{50}$ indicates the antagonistic activity of the test compound, i.e. the negative logarithm of the concentration of the test compound necessitated for the 50% inhibition.

TABLE 14

| Referential Example | Antagonistic activity on N-type calcium channels at 10 μM Inhibition rate (%) | Antagonistic activity on L-type calcium channels $pIC_{50}$ |
|---|---|---|
| 1 | 67 | 6.0 |
| 9 | 83 | 6.3 |
| 11 | 77 | 6.4 |
| 16 | 75 | 5.9 |
| 24 | 78 | 6.0 |
| 41 | 76 | 5.9 |
| 68 | 82 | 6.4 |
| 71 | 74 | 5.9 |
| 72 | 81 | 6.1 |
| 73 | 75 | 5.7 |
| 76 | 85 | 6.1 |
| 78 | 84 | 5.6 |

EXAMPLES

The following Examples will further illustrate the present invention, which by no means limit the invention.

Example 1

Effect of Gabapentin in Rat Pain Models

Analgesic activities were determined in the formalin test. Four test groups [a control group (given a saline solution) and groups given 30, 100 and 300 mg/kg of gabapentin] each composed of 6 to 7 male Sprague-Dawley rats (SD rats, 9 weeks old) were used for the experiment. Gabapentin was dissolved in a saline solution.

4 ml/kg of a saline solution or gabapentin was orally administered to the rats. Three hours after, the rats were tranquilized with halothane, and 2.5% formalin solution (100 μl) was injected subcutaneously to dorsal surface of the left hindpaw. Immediately thereafter, the rats were awaken from the anesthesia. The action of the rats was observed for 60 minutes. The number of times of retracting action, i.e., flinching action of the hindpaw in which formalin had been injected, was counted for 1 minute at an interval of one minute until 5 minutes after the formalin injection, and for 1 minute at an interval of 5 minutes from 10 to 60 minutes after the injection. As reported in a literature (J. Pharmacol. Exp. Ther. 263: 136-146, 1992), the pain reaction by the stimulation with formalin appeared in two phases. The total number of times of the flinching action observed 10 to 60 minutes after the formalin injection (the second phase) was taken as the index of the pain action.

<Results>

FIG. 1 is a graph showing the average measurement±standard error in each experiment group. The inhibiting ratios of flinches in the groups given 30, 100 and 300 mg/kg of gabapentin were 11, 42 and 47%, respectively, based on the average number of the flinches in the control group. It was found that oral administration of 30 and 100 mg/kg of gabapentin produced a dose-dependent decrease in the number of the flinches compared with the control group. However, it was also found that analgesic effect of gabapentin tended to be saturated when administered in the amount of 100 mg/kg or more.

Example 2

Analgesic Activities of the Compound A, Gabapentin and "Combination of the Compound A and Gabapentin" in Rat Pain Models Analgesic activities were determined in the formalin test. Four test groups [a control group, a group given the compound A (the compound of Referential Example 11: 3 mg/kg), a group given 100 mg/kg of gabapentin and a group given a combination of 3 mg/kg of the compound A and 100 mg/kg of gabapentin] each composed of 6 to 7 male Sprague-Dawley rats (SD rats, 9 weeks old) were used for the experiment. The administration volume to each group was as follows. In the control group, 5 ml/kg of 0.5% tragacanth solution and 4 ml/kg of a saline solution were given orally to the rats. In the group given the compound A, 5 ml/kg of the compound A suspended in 0.5% tragacanth solution and 4 ml/kg of a saline solution were given orally to them. In the group given gabapentin, 5 ml/kg of 0.5% tragacanth solution and 4 ml/kg of gabapentin dissolved in a saline solution were given orally to them. In the group given a combination of the compound A and gabapentin, 5 ml/kg of the compound A suspended in 0.5% tragacanth solution and 4 ml/kg of gabapentin dissolved in a saline solution were given orally to them.

After oral administration, the action of the rats was observed for 60 minutes and the number of times of flinching action was counted in accordance with Example 1.

<Results>

Figure 2:
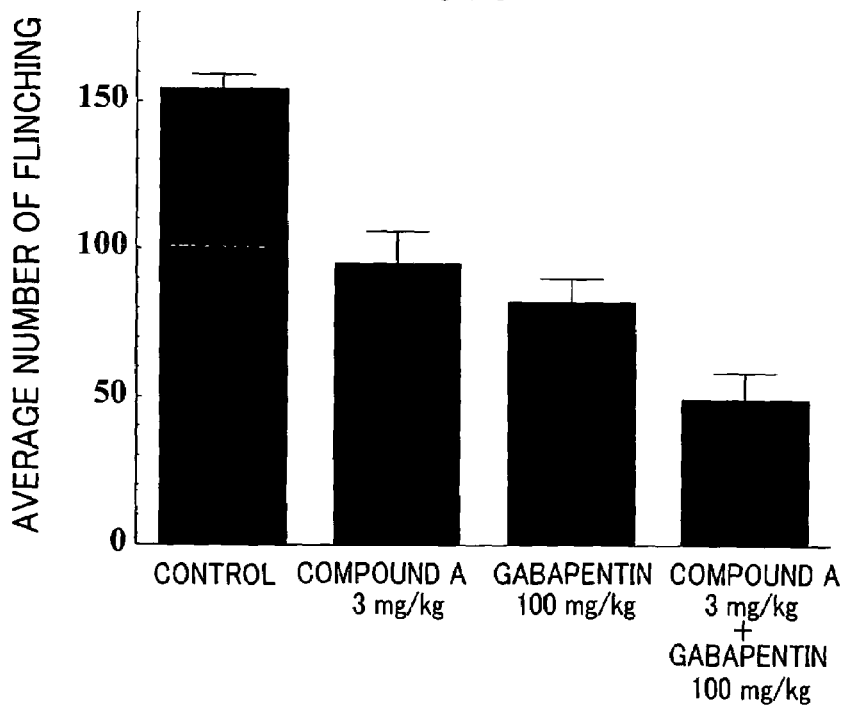
FIG. 2 shows the analgesic effects of each of compound A, gabapentin and "combination of compound A and gabapentin" in the formalin test.

FIG. 2 is a graph showing the average measurement±standard error in each experiment group. The inhibiting ratios of flinches in the group given the compound A (3 mg/kg), the group given gabapentin (100 mg/kg) and the group given the combination of the compound A and gabapentin (the compound A: 3 mg/kg and gabapentin: 100 mg/kg) were 38, 47 and 68% respectively, based on the average number of the flinches in the control group. According to Example 1, it was found that analgesic effect of gabapentin tended to be saturated when it was orally administered in the amount of 100 mg/kg or more. Therefore, the inhibiting ratio of flinches in the group given 300 mg/kg of gabapentin was not much different from that in the group given 100 mg/kg of gabapentin. On the other hand, when 3 mg/kg of the compound A was combined with 100 mg/kg of gabapentin, it was found that the analgesic effect significantly surpassed that on the group given 100 mg/kg of gabapentin and that a remarkable analgesic effect was shown compared with that on the group given 300 mg/kg of gabapentin.

Example 3

Analgesic Activities of the Compound B, Gabapentin and "Combination of the Compound B and Gabapentin" in Rat Pain Models Analgesic activities were determined in the formalin test. Four test groups [a control group, a group given the compound B (the compound of Referential Example 71: 3 mg/kg), a group given 100 mg/kg of gabapentin and a group given a combination of 3 mg/kg of the compound B and 100 mg/kg of gabapentin] each composed of 6 male Sprague-Dawley rats (SD rats, 9 weeks old) were used for the experiment. The administration volume to each group was as follows. In the control group, 3 ml/kg of polyethylene glycol 400 (PEG) and 4 ml/kg of a saline solution were given orally to the rats. In the group given the compound B, 3 ml/kg of the compound B dissolved in PEG and 4 ml/kg of a saline solution were given orally to them. In the group given gabapentin, 3 ml/kg of PEG and 4 ml/kg of gabapentin dissolved in a saline solution were given orally to them. In the group given the combination of compound B and gabapentin, 3 ml/kg of the compound B dissolved in PEG and 4 ml/kg of gabapentin dissolved in a saline solution were given orally to them.

After oral administration, the action of the rats was observed for 60 minutes and the number of times of flinching action was counted in accordance with Example 1.

<Results>

FIG. 3 is a graph showing the average measurement±standard error in each experiment group. The inhibiting ratios of flinches in the group given the compound B (3 mg/kg), the group given gabapentin (100 mg/kg) and the group given the combination of the compound B and gabapentin (the compound B: 3 mg/kg and gabapentin: 100 mg/kg) were 16, 59 and 78% respectively, based on the average number of the flinches in the control group. When 3 mg/kg of the compound B was combined with 100 mg/kg of gabapentin, it was found that the analgesic effect surpassed that on the group given 100 mg/kg of gabapentin and that a remarkable analgesic effect was shown compared with that on the group given 300 mg/kg of gabapentin of Example 1.

Example 4

Effect of Pregabalin in Rat Pain Models

Analgesic activities were determined in the formalin test. Four test groups [a control group (given a saline solution) and groups given 10, 30 and 100 mg/kg of pregabalin] each composed of 6 male Sprague-Dawley rats (SD rats, 9 weeks old) were used for the experiment. Pregabalin was dissolved in a saline solution. 4 ml/kg of a saline solution or pregabalin was orally administered to the rats.

After oral administration, the action of the rats was observed for 60 minutes and the number of times of flinching action was counted in accordance with Example 1.

<Results>

FIG. 4 is a graph showing the average measurement±standard error in each experiment group. The inhibiting ratios of flinches in the groups given 10, 30 and 100 mg/kg of pregabalin were 31, 61 and 61%, respectively, based on the average number of the flinches in the control group. It was found that oral administration of 10 and 30 mg/kg of pregabalin produced a dose-dependent decrease in the number of the flinches compared with the control group. However, it was also found that analgesic effect of pregabalin tended to be saturated when administered in the amount of 30 mg/kg or more.

Example 5

Analgesic Activities of the Compound B, Pregabalin and "Combination of the Compound B and Pregabalin" in Rat Pain Models Analgesic activities were determined in the formalin test. Four test groups [a control group, a group given the compound B (the compound of Referential Example 71: 3 mg/kg), a group given 30 mg/kg of pregabalin and a group given a combination of 3 mg/kg of the compound B and 30 mg/kg of pregabalin] each composed of 5 to 6 male Sprague-Dawley rats (SD rats, 9 weeks old) were used for the experiment. The administration volume to each group was as follows. In the control group, 3 ml/kg of polyethylene glycol 400 (PEG) and 4 ml/kg of a saline solution were given orally to the rats. In the group given the compound B, 3 ml/kg of the compound B dissolved in PEG and 4 ml/kg of a saline solution were given orally to them. In the group given pregabalin, 3 ml/kg of PEG and 4 ml/kg of pregabalin dissolved in a saline solution were given orally to them. In the group given the combination of the compound B and pregabalin, 3 ml/kg of the compound B dissolved in PEG and 4 ml/kg of pregabalin dissolved in a saline solution were given orally to them.

After oral administration, the action of the rats was observed for 60 minutes and the number of times of flinching action was counted in accordance with Example 1.

<Results>

Figure 5:
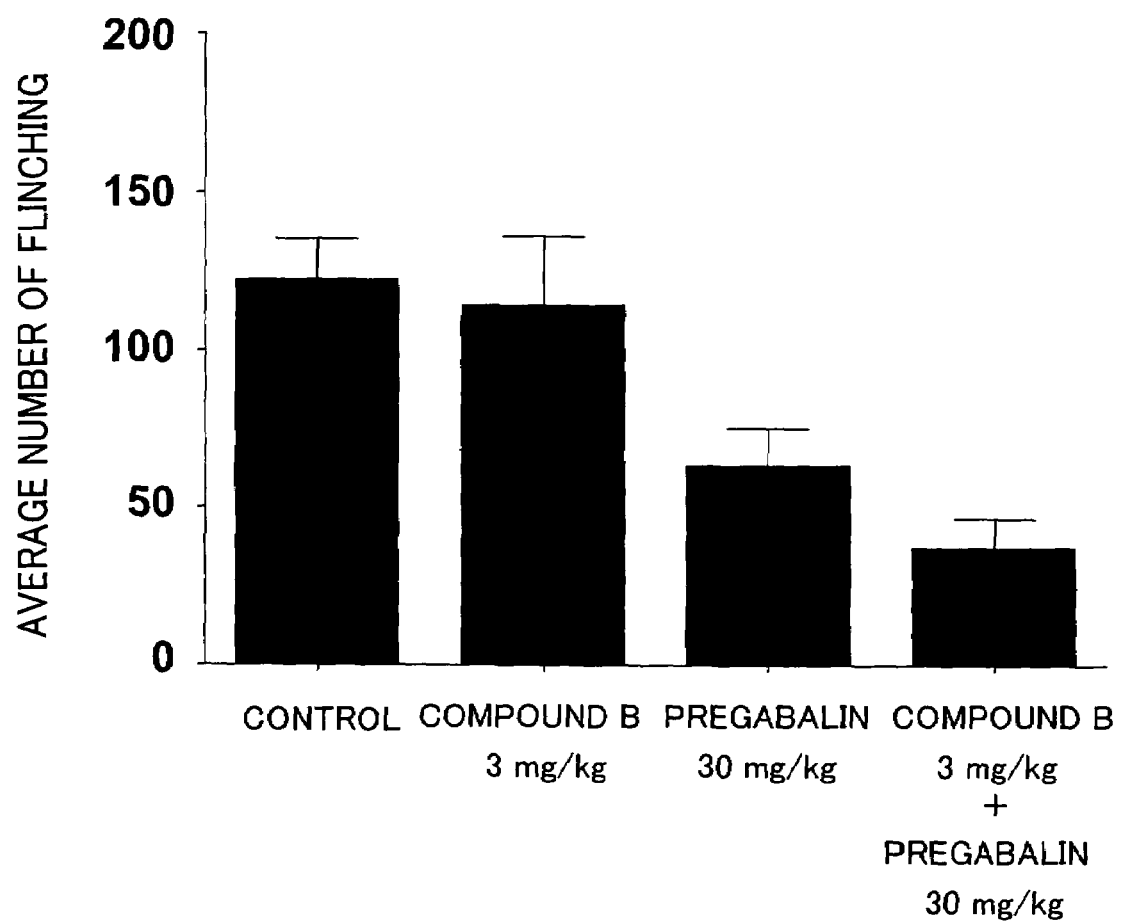
FIG. 5 shows the analgesic effects of each of compound B, pregabalin and "combination of compound B and pregabalin" in the formalin test.

FIG. 5 is a graph showing the average measurement±standard error in each experiment group. The inhibiting ratios of flinches in the group given the compound B (3 mg/kg), the group given pregabalin (30 mg/kg) and the group given the combination of the compound B and pregabalin (the compound B: 3 mg/kg and pregabalin: 30 mg/kg) were 7%, 48% and 70% respectively, based on the average number of the flinches in the control group. When 3 mg/kg of the compound B was combined with 30 mg/kg of pregabalin, it was found that the analgesic effect surpassed that on the group given 30 mg/kg of pregabalin and that a remarkable analgesic effect was shown compared with that on the group given 100 mg/kg of pregabalin of Example 4.

In preventing or treating pain, medicine having excellent quality has been desired for than ever before, such as those having excellent treating effect and no side-effects. According to the present invention, the combination use of (a) gabapentin or pregabalin, or pharmaceutically acceptable salts thereof and (b) N-type calcium channel antagonists or pharmaceutically acceptable salts thereof as active ingredients can show a stronger analgesic effect than that of a single use thereof and, therefore, they are useful for treating pain.

In clinical use, gabapentin induces side-effects such as somnolence and dizziness. In the preclinical test, a significant decrease in motor function of the body was observed by a whole body administration of 300 mg/kg of gabapentin or more.

In clinical use, pregabalin induces side-effects such as somnolence and dizziness. In the preclinical test, a significant decrease in motor function of the body was observed by a whole body administration of 100 mg/kg of pregabalin or more.

Therefore, the combination use of the medicines has potential benefits, compared with use of a single medicine in high doses, in terms of less amount of medicine needed for obtaining the treatment effect and resultant lower side-effects.

The invention claimed is:

1. A pharmaceutical composition comprising (a) gabapentin, a pharmaceutically acceptable salt of gabapentin, pregabalin, or a pharmaceutically acceptable salt of pregabalin; and (b) an N-type calcium channel antagonist or a pharmaceutically acceptable salt thereof, wherein said N-type calcium channel antagonist or pharmaceutically acceptable salt thereof is a compound of formula (1), or a pharmaceutically acceptable salt thereof:

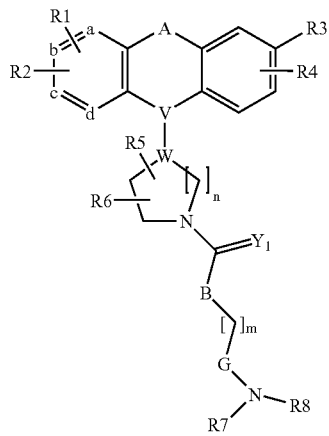

(1)

wherein A represents —CH=CH—, —CH$_2$—CH$_2$—, —CH$_2$—S—, —S—CH$_2$—, —O—, —CH$_2$—O—, —O—CH$_2$—, —N(R$^{17}$)—CH$_2$—, —CH$_2$—N(R$^{17}$)—, —CH=CH—CH$_2$—, —CH$_2$—CH=CH—, —CH$_2$—CH$_2$—CH$_2$—, —N(R$^{17}$)—(CO)—, —(CO)—N(R$^{17}$)—, —(CO)—, —(SO)— or —C(R$^{18}$R$^{19}$)— wherein R$^{17}$ represents H, a lower alkyl or an aryl, and R$^{18}$ and R$^{19}$ are each independently selected from the group consisting of H, a lower alkyl, an aryl and —C(O)OR$^{15}$ wherein R$^{15}$ represents a lower alkyl or an aryl;

a, b, c and d are each independently selected from the group consisting of CR1 and CR2;

or one of a, b, c and d is N;

R1, R2, and R4 each independently represent H, a halogen, —CF$_3$, —OR$^{14}$, —COR$^{14}$, —SR$^{14}$, —S(O)$_t$R$^{15}$, —N(R$^{14}$)$_2$, —NO$_2$, —OC(O)R$^{14}$, —CO$_2$R$^{14}$, —OCO$_2$R$^{14}$, —CN, —NR$^{14}$COOR$^{15}$, —SR$^{15}$C(O)OR$^{15}$ or —SR$^{15}$N(R$^{16}$)$_2$ wherein R$^{14}$ represents H, a lower alkyl, an aryl or an aryl-lower alkyl group, R$^{15}$ represents a lower alkyl or an aryl group, R$^{16}$ is independently selected from the group consisting of H and —C(O)OR$^{15}$, and t represents 1 or 2;

R3 represents H;

V-W represents C=C, CH—CH, CH—N or N—CH;

n represents 0 to 3;

R5 and R6 each independently represent H, a halogen, —CF$_3$, a lower alkyl or an aryl;

or R$^5$ and R$^6$ together form =O or =S;

Y$_1$ represents O or S;

B represents NR$^{17a}$, —NR$^{17a}$(CH$_2$)$_v$CHR$^{21}$—, —(CH$_2$)$_v$CHR$^{21}$— wherein v represents 0 to 3, R$^{17a}$ represents H, a lower alkyl or an aryl, R$^{21}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, —(CH$_2$)$_w$—COOR$^{29}$, —(CH$_2$)$_w$—NR$^{29}$R$^{30}$ wherein R$^{29}$ and R$^{30}$ each independently represent hydrogen atom or a lower alkyl group, and w represents 0 to 4, —(CH$_2$)$_3$NHC(NH$_2$)=NH, benzyl, 4-hydroxybenzyl, 3-indoylmethyl or 5-imidazoylmethyl;

G represents —(CO)—, —(SO)—, —(SO$_2$)— or a covalent bond;

m represents 0 to 6;

Y$_2$ represents C or S;

p and q are each independently selected from the group consisting of 1, 2 and 3;

R7 and R8 each represent H, a lower alkyl, an aryl, —(CO)R$^{18a}$, —(CS)R$^{18a}$, —(CO)NR$^{18a}$R$^{19a}$, —(CS)NR$^{18a}$R$^{19a}$ wherein R$^{18a}$ represents H, a lower alkyl, an aryl or a cycloalkyl group which may have a hetero atom in the ring, R$^{19a}$ represents H, a lower alkyl or an aryl; or R$^{18a}$ and R$^{19a}$ together form a cycloalkyl which may have a halogen, —CF$_3$, a lower alkyl or an aryl as a substituent, —(CO)OR$^{20}$—(CS)OR$^{20}$ wherein R$^{20}$ represents an alkyl group having 1 to 12 carbon atoms, an aryl group or a cycloalkyl group which may have a hetero atom in the ring, or a group of the following formula (5):

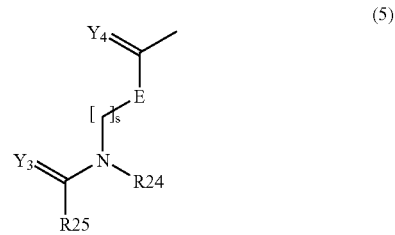

(5)

wherein Y$_4$ and Y$_3$ each represent O or S; s represents 0 to 6;

E represents NR$^{22}$ or CHR$^{23}$ wherein R$^{22}$ represents H, a lower alkyl or aryl; and R$^{23}$ represents H, a lower alkyl, an aryl, a hydroxyl-lower alkyl, —CH$_2$SH, —CH$_2$CH$_2$SCH$_3$, —CH$_2$(CO)NH$_2$, —CH$_2$CH$_2$(CO)NH$_2$, —CH$_2$COOH, —CH$_2$CH$_2$COOH, —(CH$_2$)$_4$NH$_2$, —(CH$_2$)$_3$NHC(NH$_2$)=NH, benzyl, 4-hydroxybenzyl, 3-indoylmethyl or 5-imidazoylmethyl;

R24 represents H, a lower alkyl or an aryl;

R25 represents H, a lower alkyl, an aryl, —OR$^{18a}$, —(CO)R$^{18a}$, —(CS)R$^{18a}$, —(CO)NR$^{18a}$R$^{19a}$, —(CS)NR$^{18a}$R$^{19a}$, —(CO)OR$^{20}$ or —(CS)OR$^{20}$ wherein R$^{18a}$, R$^{19a}$ and R$^{20}$ are as defined above, R9 represents H, a lower alkyl, an aryl, —(CO)R$^{18a}$, —(CS)R$^{18a}$, —(CO)NR$^{18a}$R$^{19a}$, —(CS)NR$^{18a}$R$^{19a}$, —(CO)OR$^{20}$ or —(CS)OR$^{20}$ wherein R$^{18a}$, R$^{19a}$ and R$^{20}$ are as defined above;

R10 represents H, a lower alkyl or an aryl;

R11 represents H, a lower alkyl or an aryl;

R12 represents H, a lower alkyl, an aryl, —(CO)R$^{18a}$, —(CS)R$^{18a}$, —(CO)NR$^{18a}$R$^{19a}$, —(CS)NR$^{18a}$R$^{19a}$, —(CO)OR$^{20}$ or —(CS)OR$^{20}$ wherein R$^{18a}$, R$^{19a}$ and R$^{20}$ are as defined above, or a substituent represented by the following formula (6):

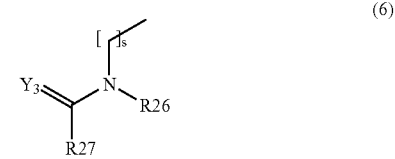

(6)

wherein s represents 1 to 6;

Y$_3$ represents O or S,

R26 represents H, a lower alkyl or an aryl;

R27 represents H, a lower alkyl, an aryl, —OR$^{18a}$, —(CO)R$^{18a}$, —(CS)R$^{18a}$, —(CO)NR$^{18a}$R$^{19a}$, —(CS)NR$^{18a}$R$^{19a}$, —(CO)OR$^{20}$ or —(CS)OR$^{20}$ wherein R$^{18a}$, R$^{19a}$ and R$^{20}$ are as defined above;

or R11 and R12 form a substituent represented by the following formula (7) together with the nitrogen atom:

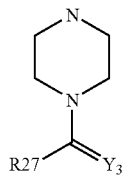
(7)

wherein Y$_3$ represents O or S, and R27 is as defined above.

2. A pharmaceutical composition according to claim 1, wherein said N-type calcium channel antagonist is:

(1-A) a compound of the following formula:

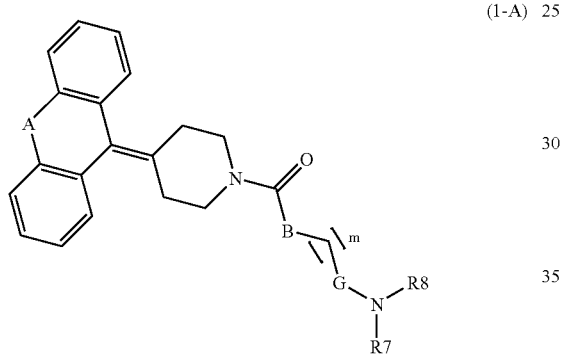
(1-A)

wherein A represents —CH═CH—, or —CH$_2$—CH$_2$—;

B represents —(CH$_2$)$_v$—CHR$^{21}$— wherein v represents 0 to 3, R$^{21}$ represents H, a lower alkyl, an aryl, a hydroxyl-lower alkyl, —(CH$_2$)$_w$—COOR$^{29}$ or —(CH$_2$)$_w$—NR$^{29}$R$^{30}$ wherein R$^{29}$ and R$^{30}$ each independently represent hydrogen atom or a lower alkyl group and w represents 0 to 4;

G represents —(CO)— or a covalent bond;

m represents 0 to 6; and

R7 and R8 each independently represent H, a lower alkyl, an aryl, —(CO)R$^{18a}$ wherein R$^{18a}$ represents H, a lower alkyl, an aryl or a cycloalkyl group which may contain a hetero atom in the ring, or —(CO)OR$^{20}$ wherein R$^{20}$ represents an alkyl group having 1 to 12 carbon atoms, an aryl or a cycloalkyl group which may have a hetero atom in the ring or a pharmaceutically acceptable salt thereof.

3. A pharmaceutical composition according to claim 1, which comprises gabapentin or a pharmaceutically acceptable salt thereof.

4. A pharmaceutical composition according to claim 1, which comprises pregabalin or a pharmaceutically acceptable salt thereof.

5. A pharmaceutical composition according to claim 1, wherein said N-type calcium channel antagonist is selected from the group consisting of a compound of formula (1-B) and a pharmaceutically acceptable salt thereof:

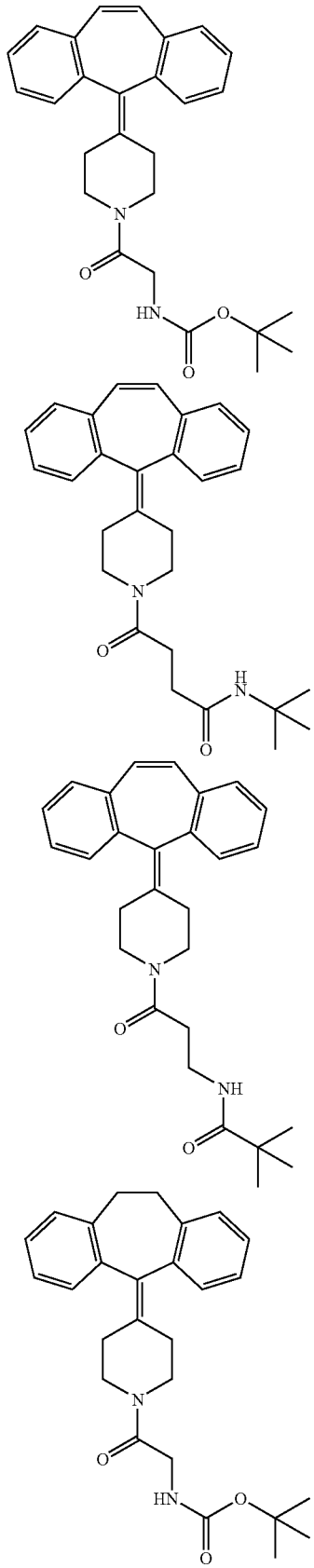
(1-B)

-continued

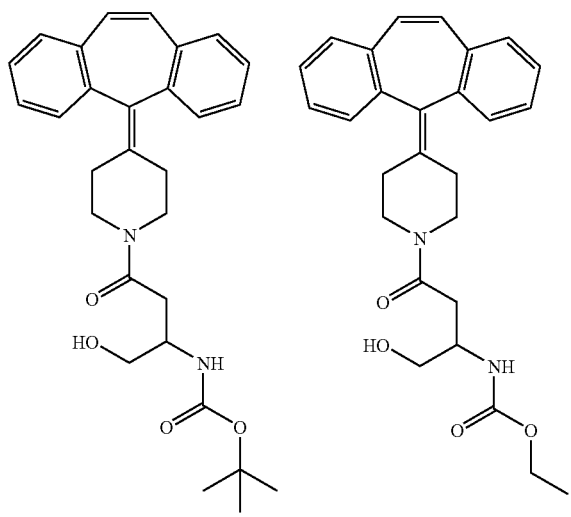

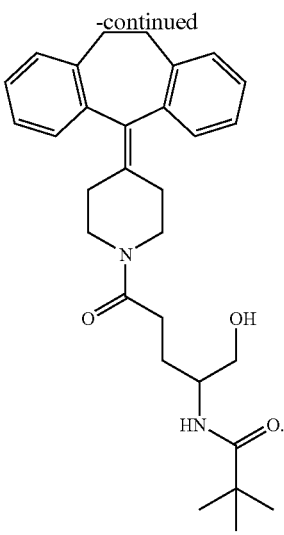

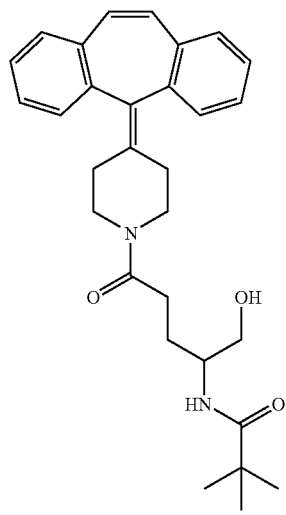

6. A pharmaceutical composition according to claim 1, which
comprises N-{3-[4-(5H-dibenzo[a, d] [7] annulen-5-ylidene)-1-piperidinyl]-3-oxopropyl}-2, 2-dimethyl-propanamide or a pharmaceutically acceptable salt thereof.

7. A pharmaceutical composition according to claim 6, which comprises gabapentin or a pharmaceutically acceptable salt thereof.

8. A pharmaceutical composition according to claim 6, which comprises pregabalin or a pharmaceutically acceptable salt thereof.

9. A pharmaceutical composition according to claim 1, which comprises (S)—N-[4-[4-(5H-dibenzo[a,d] [7]annulen-5-ylidene)-1-piperidinyl]-1-(hydroxylmethyl) -4-oxobutyl]-2.2-dimethylpropanamide or a pharmaceutically acceptable salt thereof.

10. A pharmaceutical composition according to claim 9, which comprises gabapentin or a pharmaceutically acceptable salt thereof.

11. A pharmaceutical composition according to claim 9, which comprises pregabalin or a pharmaceutically acceptable salt thereof.

* * * * *